United States Patent
Ha et al.

(10) Patent No.: US 10,991,887 B2
(45) Date of Patent: Apr. 27, 2021

(54) AMINE COMPOUND AND ORGANIC LIGHT-EMITTING DEVICE COMPRISING SAME

(71) Applicant: LG Chem, Ltd., Seoul (KR)

(72) Inventors: Jae Seung Ha, Daejeon (KR); Sung Kil Hong, Daejeon (KR); Sang Duk Suh, Daejeon (KR)

(73) Assignee: LG Chem, Ltd.

( * ) Notice: Subject to any disclaimer, the term of this patent is extended or adjusted under 35 U.S.C. 154(b) by 401 days.

(21) Appl. No.: 15/764,400

(22) PCT Filed: Oct. 6, 2016

(86) PCT No.: PCT/KR2016/011167
§ 371 (c)(1),
(2) Date: Mar. 29, 2018

(87) PCT Pub. No.: WO2017/061779
PCT Pub. Date: Apr. 13, 2017

(65) Prior Publication Data
US 2018/0277762 A1    Sep. 27, 2018

(30) Foreign Application Priority Data

Oct. 6, 2015 (KR) .................. 10-2015-0140440
Sep. 29, 2016 (KR) .................. 10-2016-0125684

(51) Int. Cl.
| | | |
|---|---|---|
| *H01L 51/00* | (2006.01) | |
| *C09K 11/06* | (2006.01) | |
| *C07C 211/61* | (2006.01) | |
| *C07D 417/12* | (2006.01) | |
| *C07D 279/26* | (2006.01) | |
| *C07D 219/14* | (2006.01) | |
| *C07D 307/91* | (2006.01) | |
| *C07D 409/12* | (2006.01) | |
| *C07D 265/38* | (2006.01) | |
| *C07D 333/76* | (2006.01) | |
| *H01L 51/50* | (2006.01) | |
| *H01L 51/56* | (2006.01) | |

(52) U.S. Cl.
CPC .......... *H01L 51/006* (2013.01); *C07C 211/61* (2013.01); *C07D 219/14* (2013.01); *C07D 265/38* (2013.01); *C07D 279/26* (2013.01); *C07D 307/91* (2013.01); *C07D 333/76* (2013.01); *C07D 409/12* (2013.01); *C07D 417/12* (2013.01); *C09K 11/06* (2013.01); *H01L 51/0059* (2013.01); *H01L 51/0061* (2013.01); *C07C 2603/18* (2017.05); *C07C 2603/26* (2017.05); *C07C 2603/42* (2017.05); *C07C 2603/94* (2017.05); *C07C 2603/97* (2017.05); *C09K 2211/1007* (2013.01); *C09K 2211/1011* (2013.01); *C09K 2211/1014* (2013.01); *H01L 51/001* (2013.01); *H01L 51/0056* (2013.01); *H01L 51/0058* (2013.01); *H01L 51/0073* (2013.01); *H01L 51/0074* (2013.01); *H01L 51/5012* (2013.01); *H01L 51/5056* (2013.01); *H01L 51/5088* (2013.01); *H01L 51/56* (2013.01); *H01L 2251/558* (2013.01)

(58) Field of Classification Search
CPC .............. H01L 51/006; H01L 51/0059; H01L 51/0061; H01L 51/0073; H01L 51/0074; H01L 51/001; H01L 51/0056; H01L 51/0058; H01L 51/5012; H01L 51/56; H01L 51/5056; H01L 51/5088; H01L 2251/558; C07D 417/12; C07D 279/26; C07D 219/14; C07D 307/91; C07D 409/12; C07D 265/38; C07D 333/76; C07C 211/61; C07C 2603/26; C07C 2603/42; C07C 2603/94; C07C 2603/97; C07C 2603/18; C09K 11/06; C09K 2211/1007; C09K 2211/1011; C09K 2211/014
See application file for complete search history.

(56) References Cited

U.S. PATENT DOCUMENTS

| | | | |
|---|---|---|---|
| 6,747,287 B1 | 6/2004 | Toguchi et al. | |
| 2007/0262703 A1 | 11/2007 | Tsai et al. | |
| 2015/0065730 A1 | 3/2015 | Montenegro et al. | |
| 2016/0181524 A1* | 6/2016 | Lee .................. | C09K 11/06 257/40 |
| 2018/0019405 A1 | 1/2018 | Montenegro et al. | |
| 2018/0212149 A1* | 7/2018 | Pfister .................. | C07D 307/91 |

FOREIGN PATENT DOCUMENTS

| | | |
|---|---|---|
| CN | 103589419 A | 2/2014 |
| EP | 3221292 A1 | 9/2017 |
| JP | 2003124472 A | 4/2003 |
| JP | 2004083483 A | 3/2004 |
| JP | 2010027681 A | 2/2010 |
| JP | 2015513530 A | 5/2015 |
| KR | 20000051826 A | 8/2000 |
| KR | 20150010016 A | 1/2015 |
| TW | 201339123 A | 10/2013 |
| WO | 2013120577 A1 | 8/2013 |
| WO | 2015009076 A1 | 1/2015 |
| WO | 2015012618 A1 | 1/2015 |
| WO | 2016078738 A1 | 5/2016 |

OTHER PUBLICATIONS

Search report from International Application No. PCT/KR2016/011167, dated Jan. 18, 2017.
Extended European Search Report and Written Opinion for EP Application No. 16853895.7, dated Sep. 21, 2018.

\* cited by examiner

*Primary Examiner* — Robert S Jones, Jr.
(74) *Attorney, Agent, or Firm* — Lerner, David, Littenberg, Krumholz & Mentlik, LLP

(57) ABSTRACT

The present specification provides an amine compound and an organic light emitting device including the same.

14 Claims, 1 Drawing Sheet

[Figure 1]
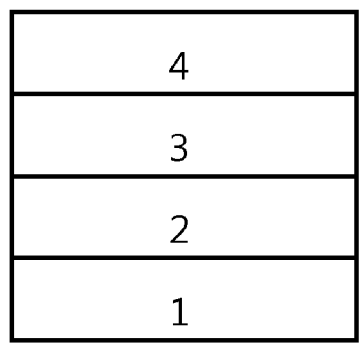
[Figure 2]
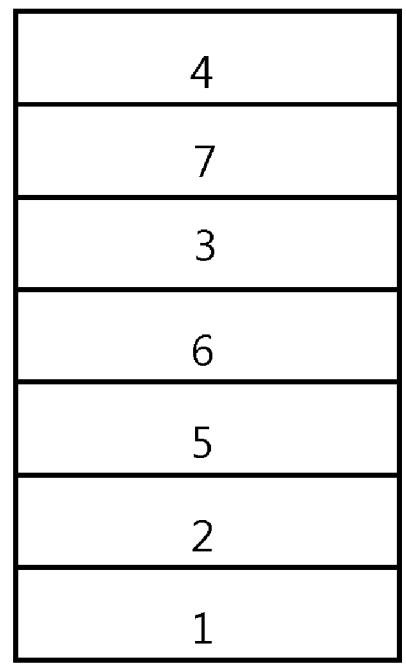

AMINE COMPOUND AND ORGANIC LIGHT-EMITTING DEVICE COMPRISING SAME

CROSS-REFERENCE TO RELATED APPLICATION

The present specification is a national phase entry under 35 U.S.C. § 371 of International Application No. PCT/KR2016/011167 filed on Oct. 6, 2016, which claims priority from Korean Patent Application Nos. 10-2015-0140440 and 10-2016-0125684 filed on Oct. 6, 2015, and Sep. 29, 2016, respectively, all of which are incorporated herein by reference.

TECHNICAL FIELD

Background Art

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DETAILED DESCRIPTION OF THE INVENTION

Technical Problem

The present specification describes an amine compound and an organic light emitting device including the same.

Technical Solution

An exemplary embodiment of the present specification provides a compound represented by the following Chemical Formula 1:

[Chemical Formula 1]

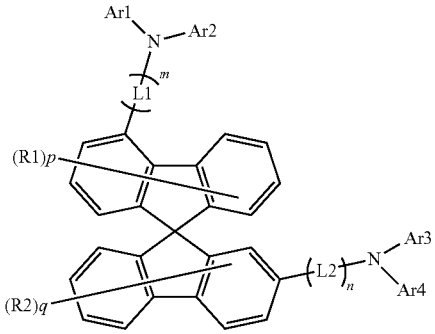

In Chemical Formula 1,

Ar1 to Ar4 are the same as or different from each other, and are each independently a substituted or unsubstituted aryl group or a substituted or unsubstituted heterocyclic group, or Ar1 and Ar2 are linked to each other by E1, or Ar3 and Ar4 are linked to each other by E2, E1 and E2 are the same as or different from each other, and are each independently a direct bond, CRR', NR, O, or S, L1 and L2 are the same as or different from each other, and are each independently a direct bond, or a substituted or unsubstituted arylene or a substituted or unsubstituted heteroarylene, n and m are the same as or different from each other, and are each an integer of 0 to 3, and when n and m are each 2 or more, substituents in the parenthesis are the same as or different from each other, and R1, R2, R, and R' are the same as or different from each other, and are each independently hydrogen; deuterium; a halogen group; a nitrile group; a substituted or unsubstituted alkyl group; a substituted or unsubstituted cycloalkyl group; a substituted or unsubstituted alkoxy group; a substituted or unsubstituted aryloxy group; a substituted or unsubstituted aralkyl group; a substituted or unsubstituted aralkenyl group; a substituted or unsubstituted alkylaryl group; a substituted or unsubstituted aryl group; or a substituted or unsubstituted heterocyclic group, p and q are the same as or different from each other, and are each an integer of 0 to 7, and when p and q are each 2 or more, substituents in the parenthesis are the same as or different from each other.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

Advantageous Effects

The compound described in the present specification may be used as a material for an organic material layer of an organic light emitting device. The compound according to at least one exemplary embodiment may improve the efficiency, achieve low driving voltage and/or improve lifetime characteristics in the organic light emitting device. In particular, the compound described in the present specification may be used as a material for hole injection, hole transport, hole injection and hole transport, light emission, electron transport, or electron injection. In addition, the compound described in the present specification may be preferably used as a material for a light emitting layer, and electron transport or electron injection. Furthermore, more preferably, when the compound described in the present specification is used as a material for hole injection, hole transport, and hole adjusting layers, low voltage, high efficiency and/or long lifetime characteristics are exhibited.

DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transport layer 6, a light emitting layer 3, an electron transport layer 7, and a negative electrode 4.

EXPLANATION OF REFERENCE NUMERALS AND SYMBOLS

1: Substrate
2: Positive electrode
3: Light emitting layer
4: Negative electrode
5: Hole injection layer
6: Hole transport layer
7: Electron transport layer

BEST MODE

Hereinafter, the present specification will be described in more detail.

An exemplary embodiment of the present specification provides the compound represented by Chemical Formula 1. Examples of the substituents will be described below, but are not limited thereto.

In the present specification, the term "substituted or unsubstituted" means being unsubstituted or substituted with one or more substituents selected from the group consisting of deuterium; a halogen group; a nitrile group; an alkoxy group; an aryloxy group; an alkyl group; a cycloalkyl group; an alkenyl group; an aryl group; an aralkyl group; an aralkenyl group; an alkylaryl group; and a heterocyclic group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to yet another exemplary embodiment, the number of carbon atoms of the cycloalkyl group is 3 to 20. According to still yet another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group is not particularly limited, but has preferably 1 to 40 carbon atoms. According to an exemplary embodiment, the number of carbon atoms of the alkoxy group is 1 to 10. According to another exemplary embodiment, the number of carbon atoms of the alkoxy group is 1 to 6. Specific examples of the alkoxy group include a methoxy group, an ethoxy group, a propoxy group, an isobutyloxy group, a sec-butyloxy group, a pentyloxy group, an iso-amyloxy group, a hexyloxy group, and the like, but are not limited thereto.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, a triphenylene group, and the like, but are not limited thereto.

In the present specification, a fluorenyl group may be substituted, and two substituents may combine with each other to form a spiro structure.

When the fluorenyl group is substituted, examples of the fluorenyl group include

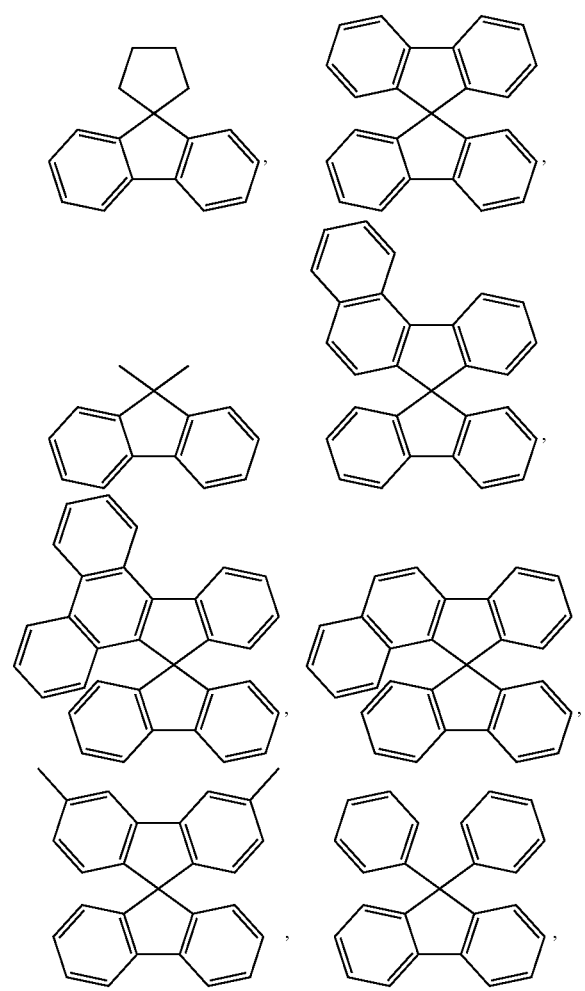

and the like.

However, the fluorenyl group is not limited thereto.

In the present specification, a heterocyclic group is a heterocyclic group including one or more of N, O, S, Si, and Se as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenoxazinyl group, a phenothiazinyl group, a dibenzofuranyl group, and the like, but are not limited thereto. The heterocyclic group includes an aliphatic heterocyclic group and an aromatic heterocyclic group.

In the present specification, the above-described description on the heterocyclic group may be applied to a heteroaryl group except for an aromatic group.

In the present specification, the above-described description on the aryl group may be applied to an aryl group in an aryloxy group, an aralkyl group, and an alkylaryl group.

In the present specification, the above-described description on the alkyl group may be applied to an alkyl group in an aralkyl group and an alkylaryl group.

In the present specification, the above-described description on the heterocyclic group may be applied to a heteroaryl group.

In the present specification, the above-described description on the aryl group may be applied to an arylene except for a divalent arylene group.

In the present specification, the above-described description on the heterocyclic group may be applied to a heteroarylene except for a divalent heteroarylene group.

According to an exemplary embodiment of the present specification, Chemical Formula 1 may be represented by the following Chemical Formula 2.

[Chemical Formula 2]

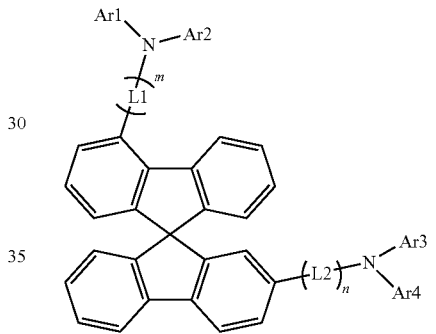

In Chemical Formula 2, the definition of the substituent is the same as that described in Chemical Formula 1.

According to an exemplary embodiment of the present specification, Ar1 to Ar4 are the same as or different from each other, and are each independently a substituted or unsubstituted aryl group having 6 to 60 carbon atoms, or a heterocyclic group having 2 to 60 carbon atoms.

According to an exemplary embodiment of the present specification, Ar1 to Ar4 are the same as or different from each other, and are each independently a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted phenanthryl group, a substituted or unsubstituted triphenylene group, a substituted or unsubstituted fluorenyl group, a substituted or unsubstituted spirobifluorenyl group, a substituted or unsubstituted dibenzothiophene group, a substituted or unsubstituted dibenzofuran group, or a substituted or unsubstituted carbazole group.

According to an exemplary embodiment of the present specification, Ar1 to Ar4 are the same as or different from each other, and are each independently a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted phenanthryl group, a substituted or unsubstituted triphenylene group, a substituted or unsubstituted fluorenyl group, a substituted or unsubstituted spirobifluorenyl group, a substituted or unsubstituted dibenzothiophene group, a substituted or unsubstituted dibenzofuran group, or a substituted or unsubstituted carbazole group.

According to an exemplary embodiment of the present specification, Ar1 to Ar4 are the same as or different from each other, and are each independently a phenyl group, a biphenyl group, a terphenyl group, a quarterphenyl group, a naphthyl group, a phenanthryl group, a triphenylene group, a fluorenyl group which is unsubstituted or substituted with an alkyl group or an aryl group, a spirobifluorenyl group, a dibenzothiophene group, a dibenzofuran group, or a carbazole group which is unsubstituted or substituted with an aryl group.

According to an exemplary embodiment of the present specification, Ar1 to Ar4 are the same as or different from each other, and are each independently a phenyl group, a biphenyl group, a terphenyl group, a quarterphenyl group, a naphthyl group, a phenanthryl group, a triphenylene group, a fluorenyl group which is unsubstituted or substituted with a methyl group or a phenyl group, a spirobifluorenyl group, a dibenzothiophene group, a dibenzofuran group, or a carbazole group which is unsubstituted or substituted with a phenyl group.

According to an exemplary embodiment of the present specification, Ar1 to Ar4 are the same as or different from each other, and may be each independently selected from the following structural formulae.

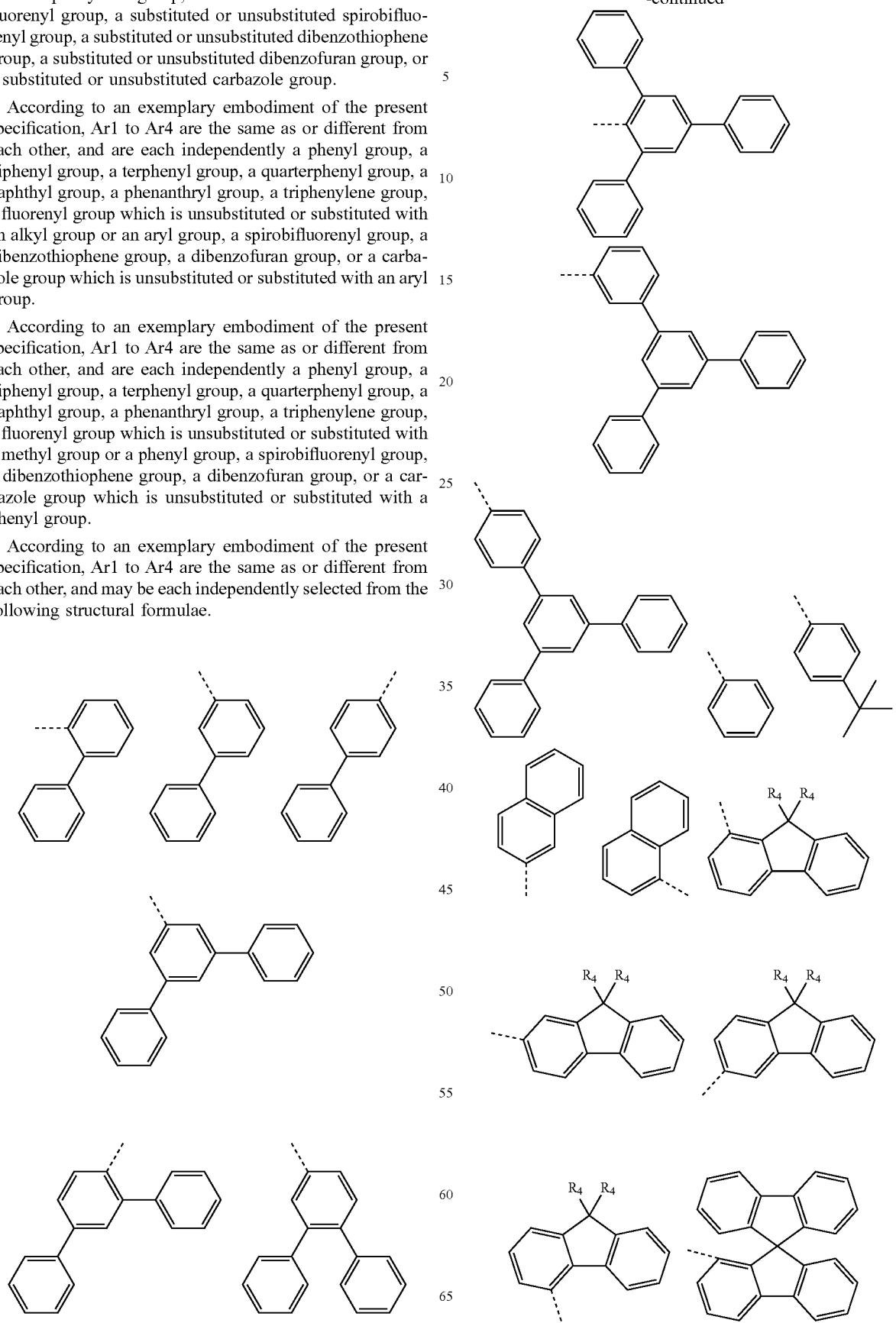

-continued

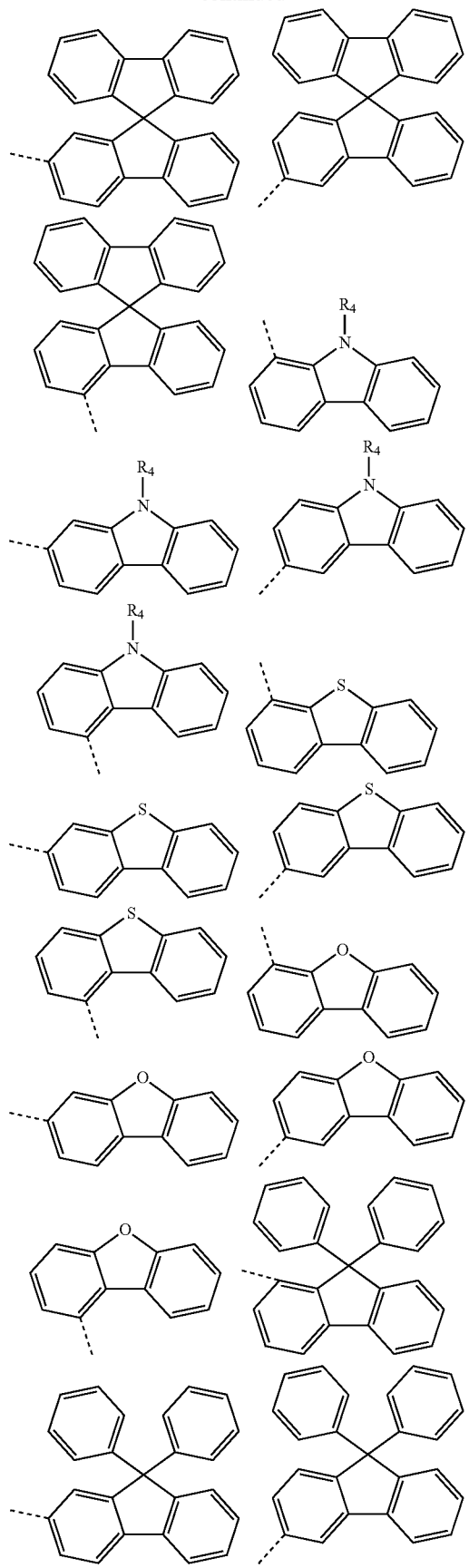
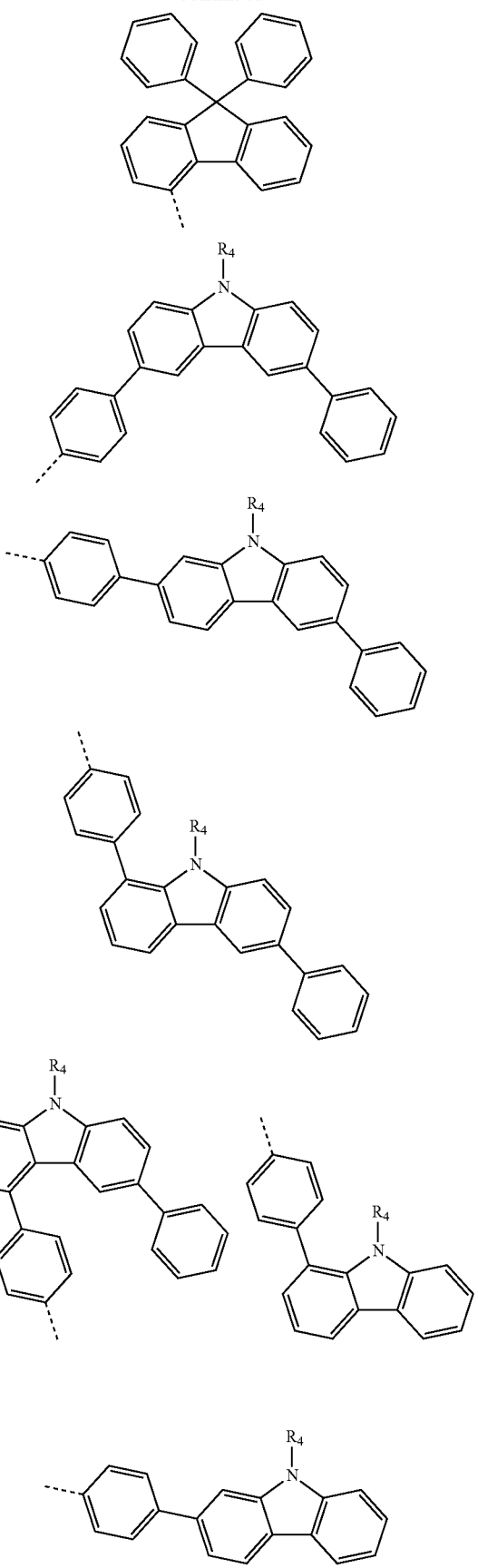

-continued
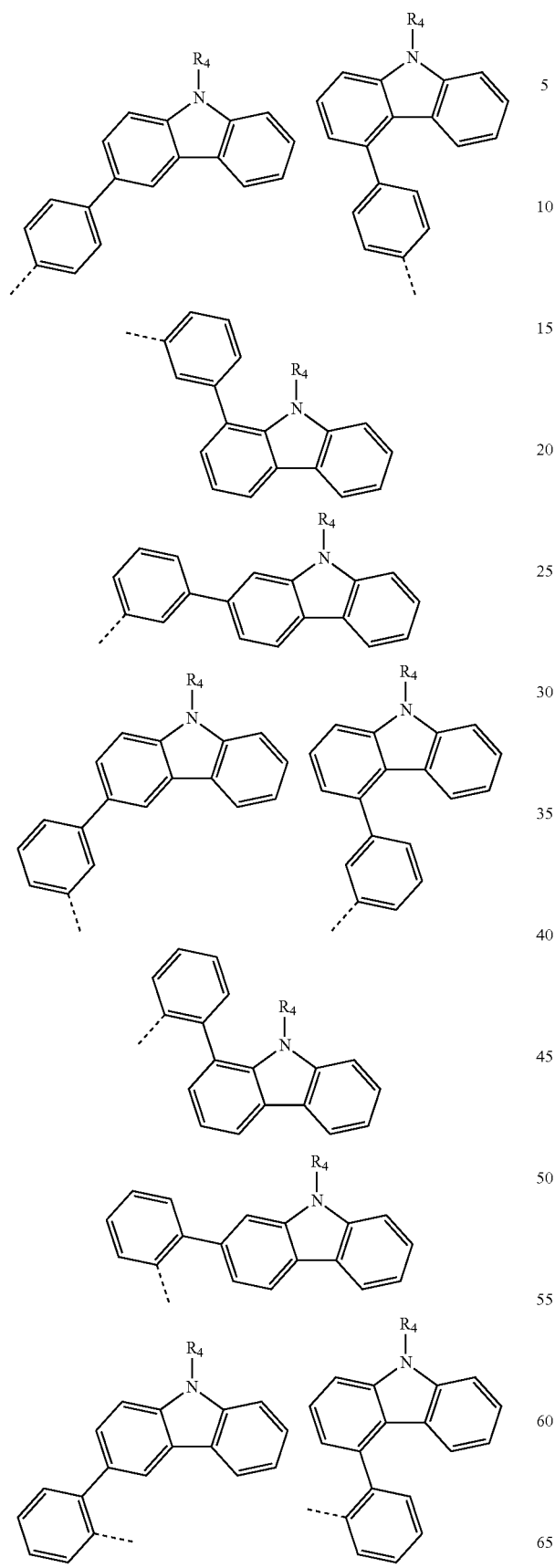
-continued
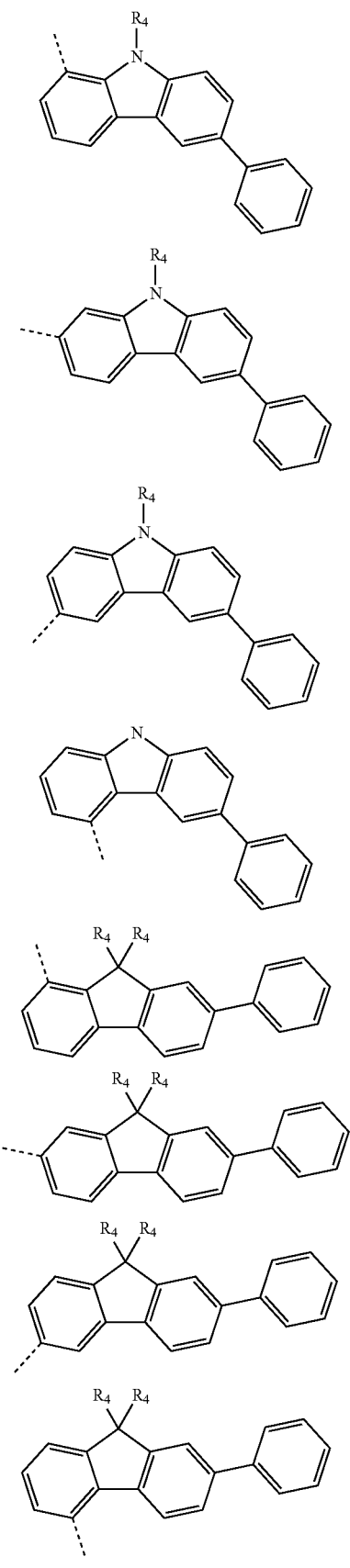

-continued
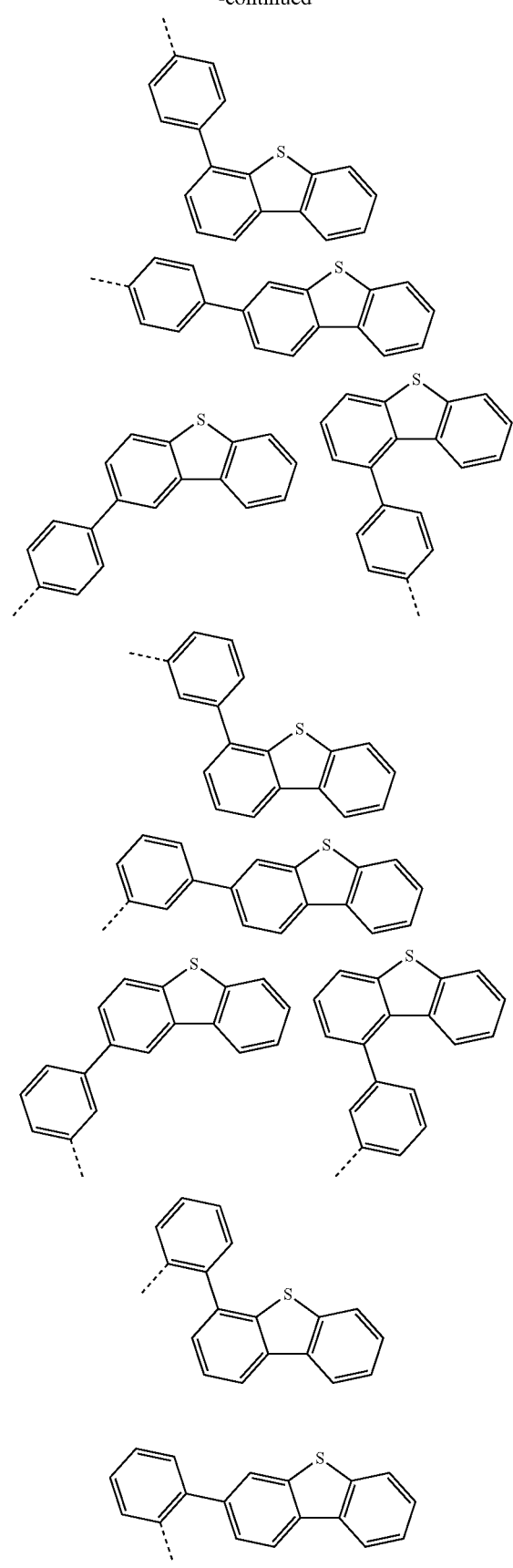
-continued
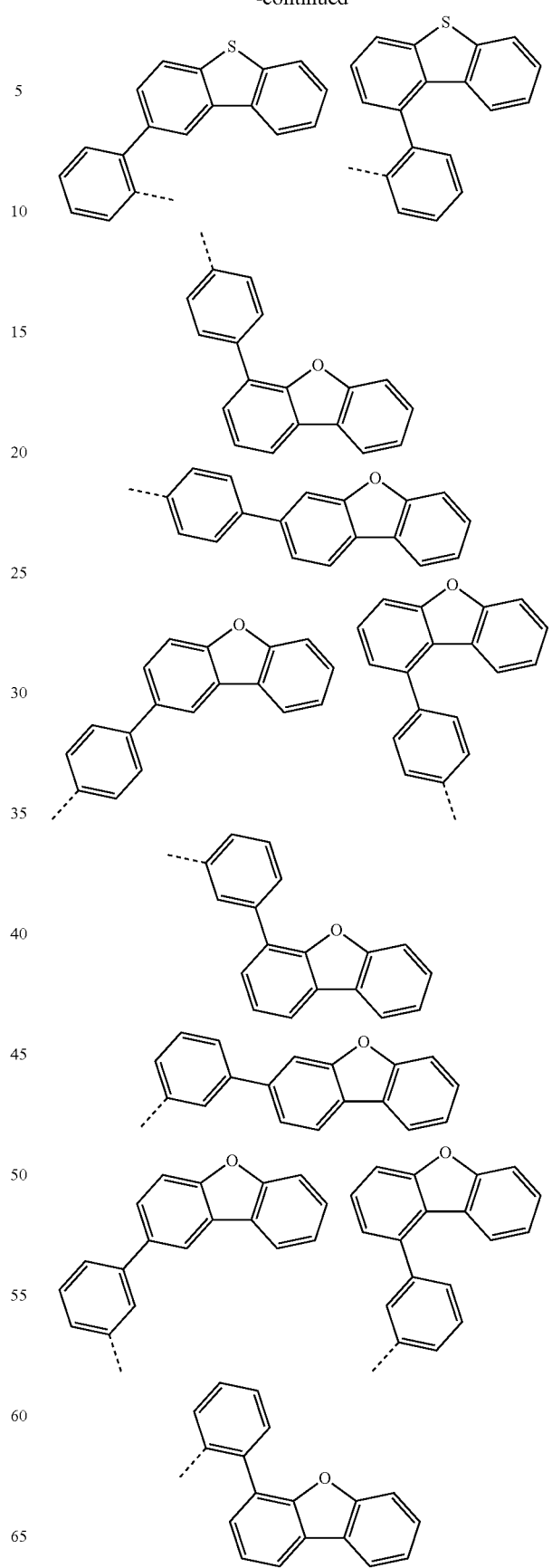

-continued

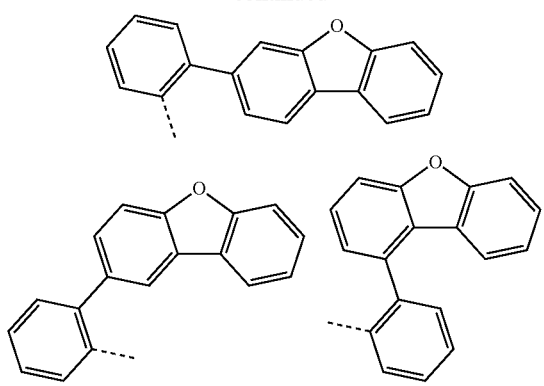

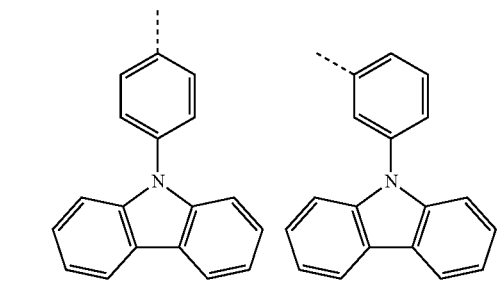

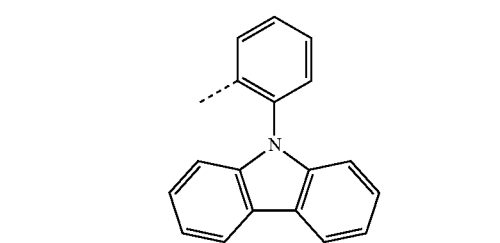

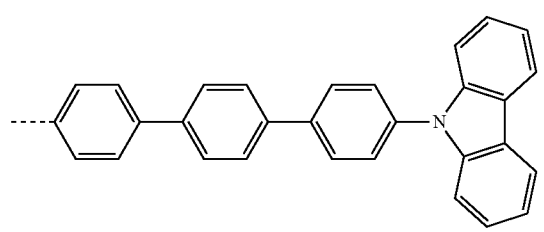

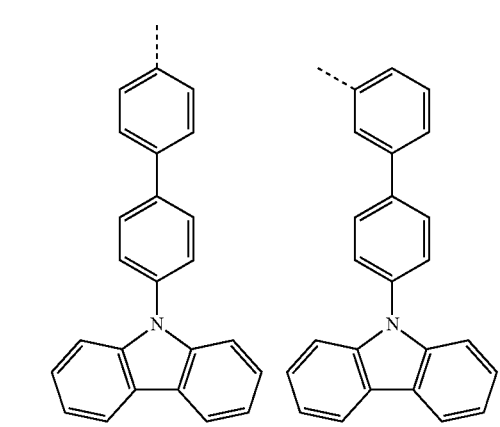

-continued

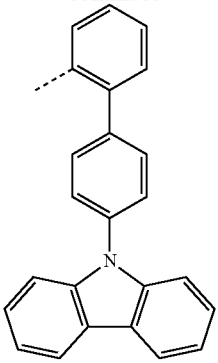

In the structural formulae, $R_4$'s are the same as or different from each other, and are an alkyl group or an aryl group.

In the structural formulae, $R_4$'s are the same as or different from each other, and are a methyl group or a phenyl group.

According to an exemplary embodiment of the present specification, Ar1 and Ar2 or Ar3 and Ar4 may be bonded to each other through CRR', NR, S, or O.

According to an exemplary embodiment of the present specification, Ar1 and Ar2 or Ar3 and Ar4 may be bonded to each other through CRR', NR, S, or O to form a structure as described below.

-continued

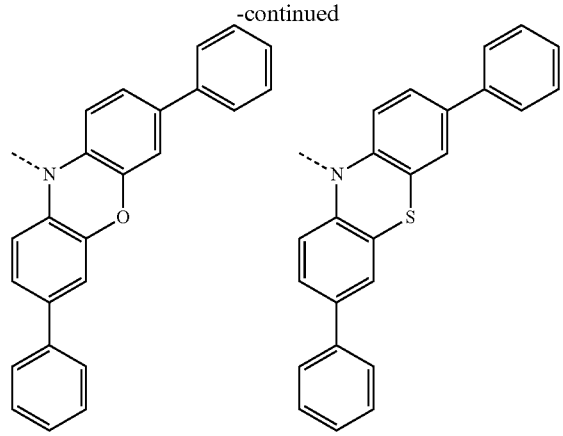

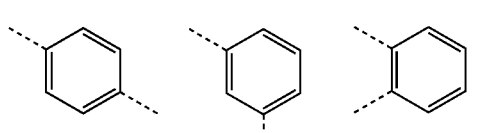

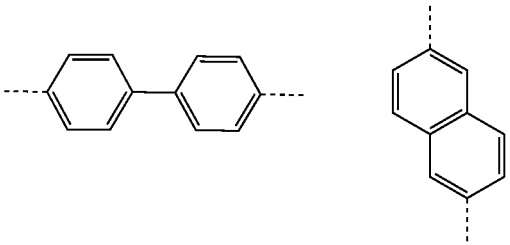

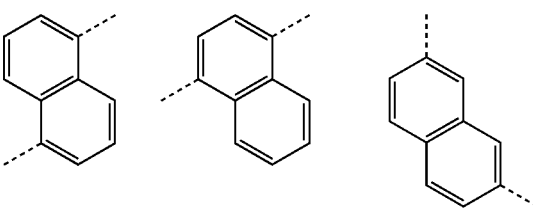

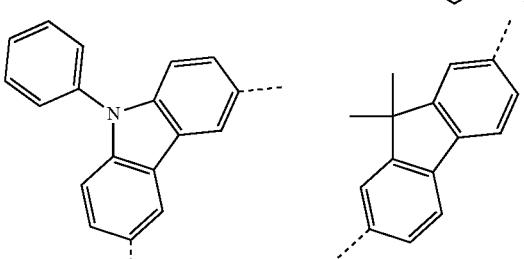

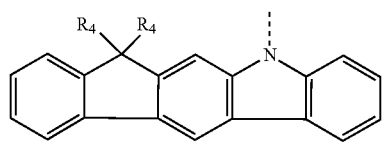

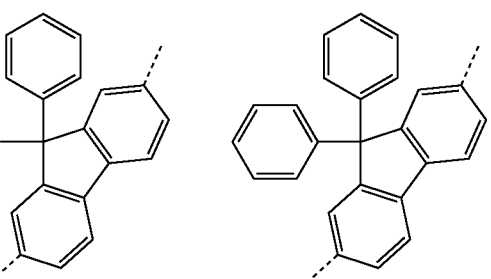

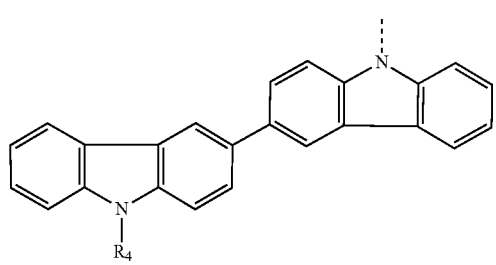

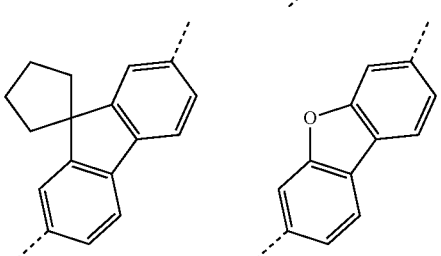

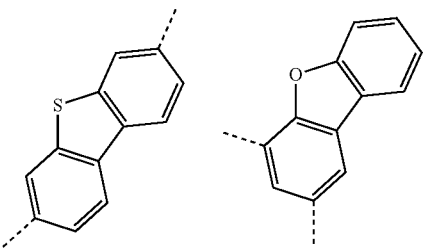

In the structural formulae, $R_4$'s are the same as or different from each other, and are an alkyl group or an aryl group.

According to an exemplary embodiment of the present specification, L1 and L2 are the same as or different from each other, and are each independently a direct bond, or a substituted or unsubstituted arylene having 6 to 60 carbon atoms; or a substituted or unsubstituted heteroarylene having 2 to 60 carbon atoms.

According to an exemplary embodiment of the present specification, L1 and L2 are the same as or different from each other, and are a direct bond, or may be selected from the following structural formulae.

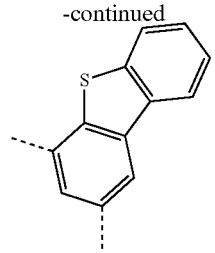
According to an exemplary embodiment of the present specification, L1 and L2 are the same as or different from each other, and are a direct bond, or phenylene.
According to an exemplary embodiment of the present invention, the compound of Chemical Formula 1 may be any one selected from the following compounds.
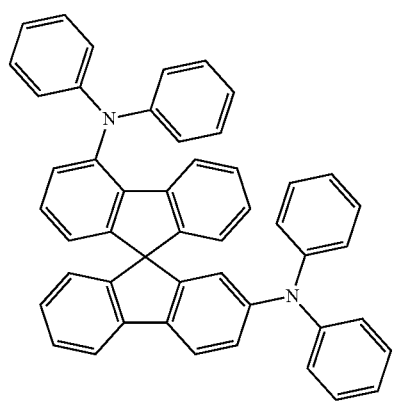
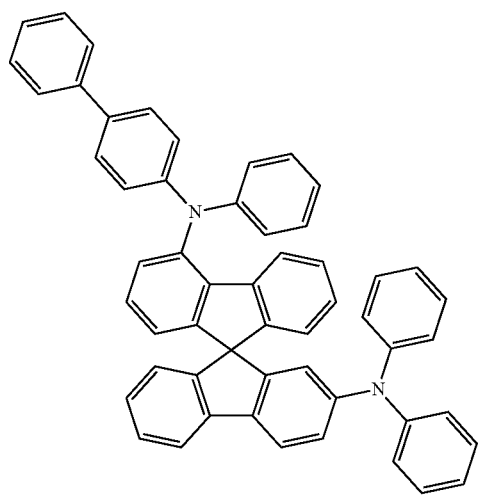
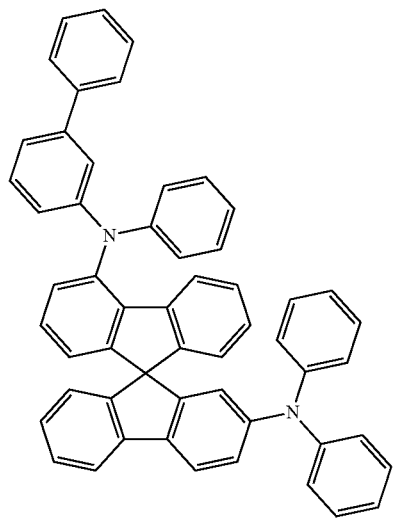
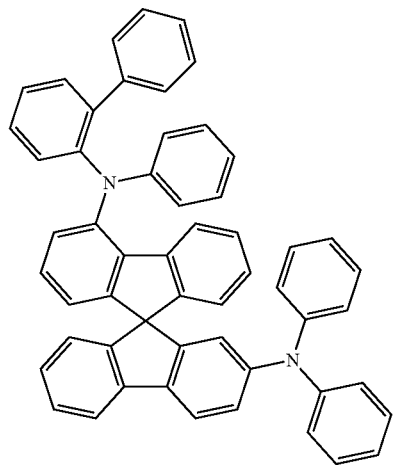
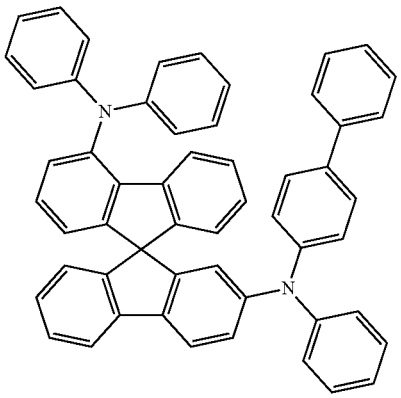

-continued
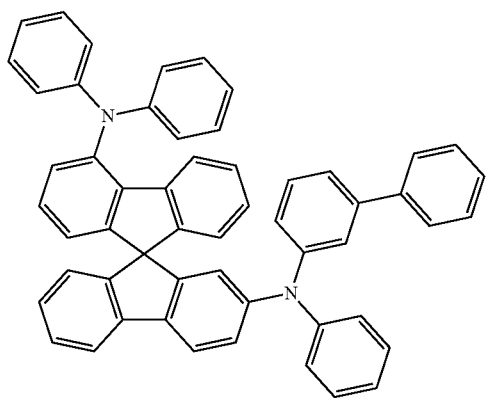
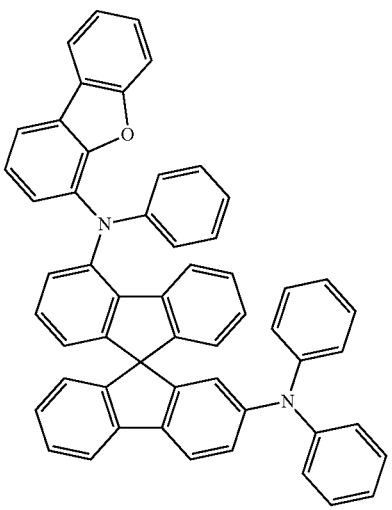
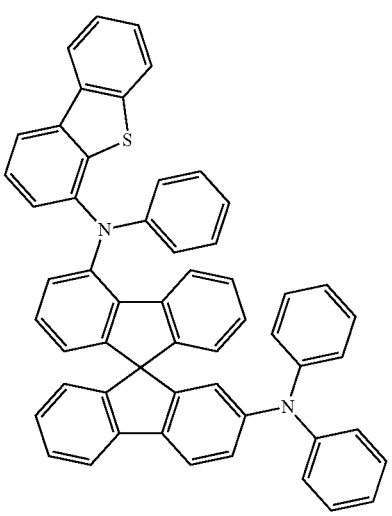
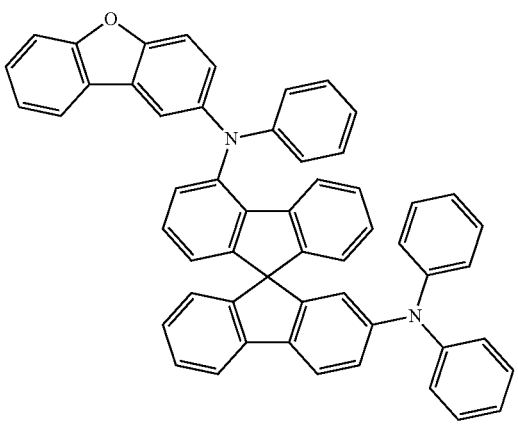

-continued
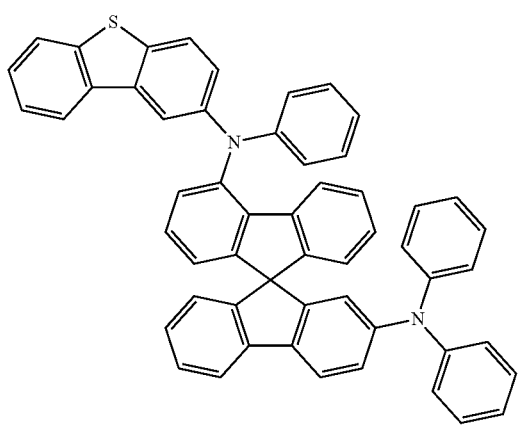
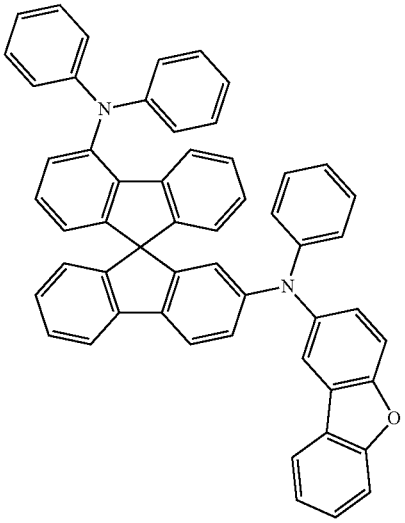
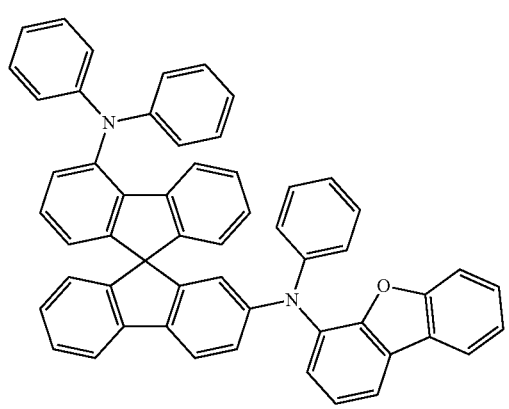
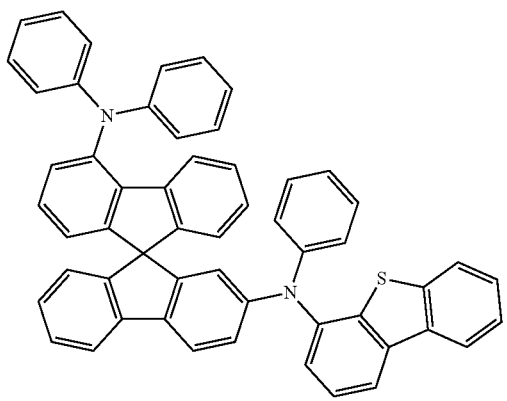
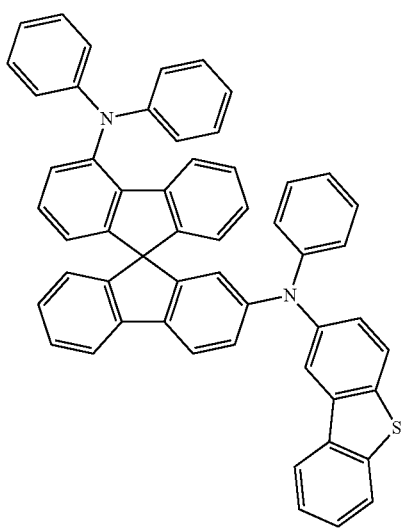
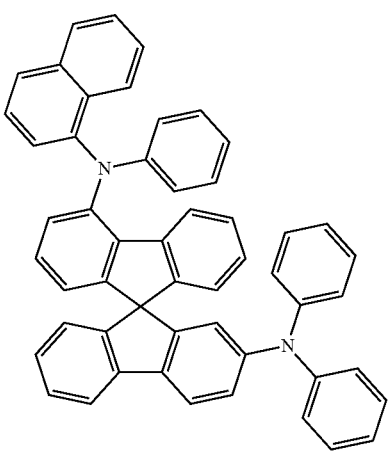

-continued
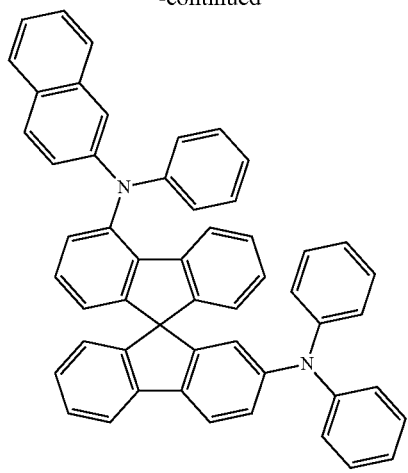
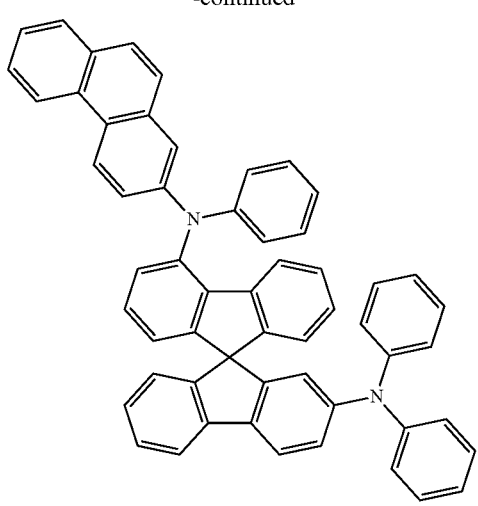
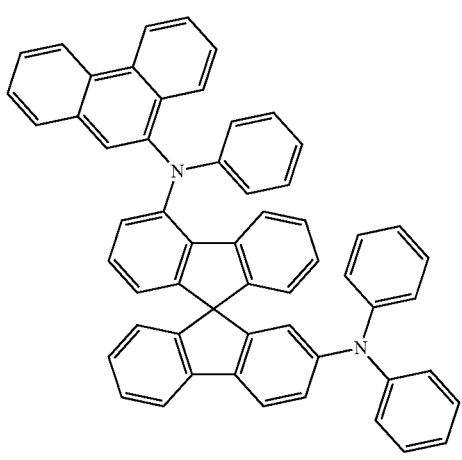
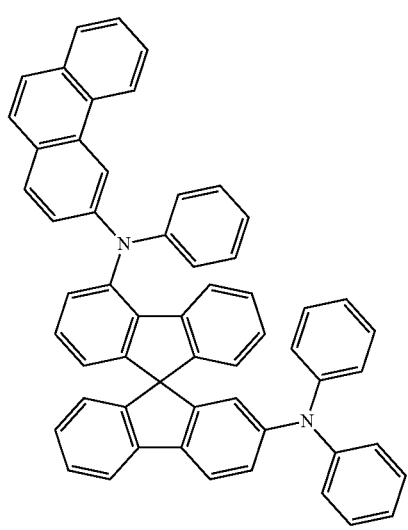
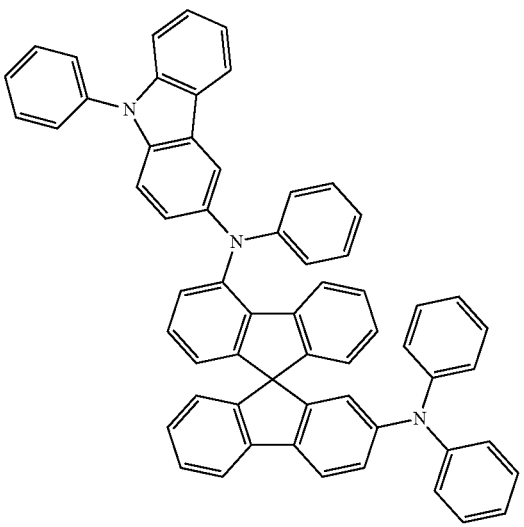

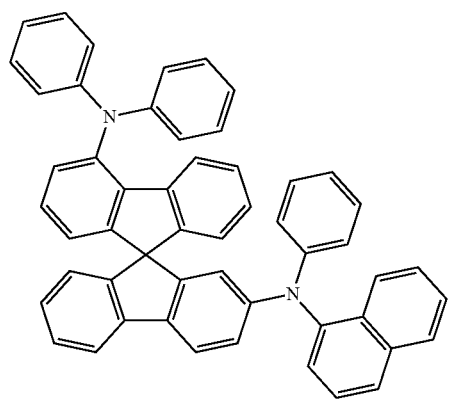
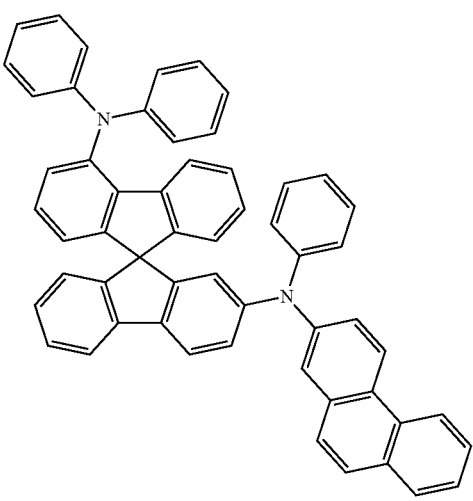
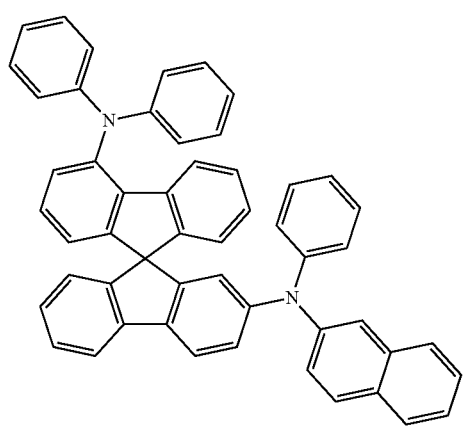
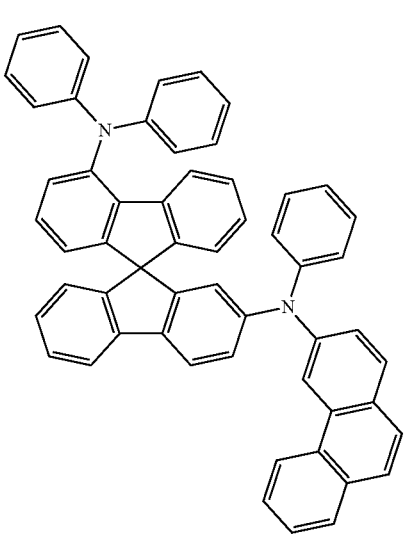
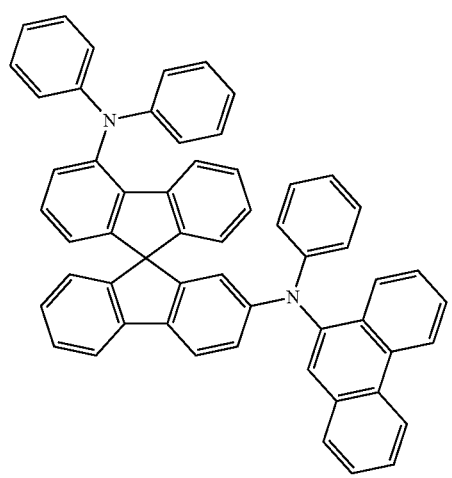
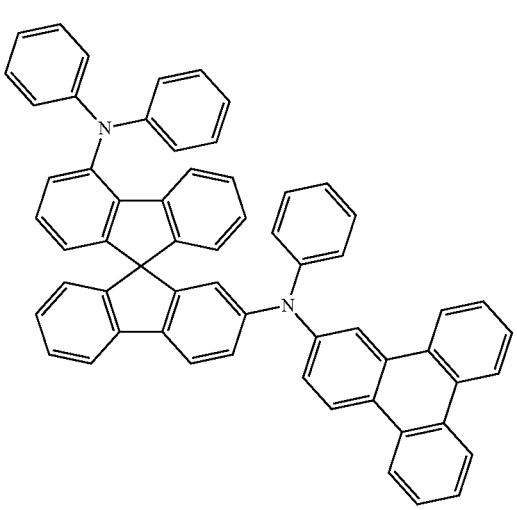

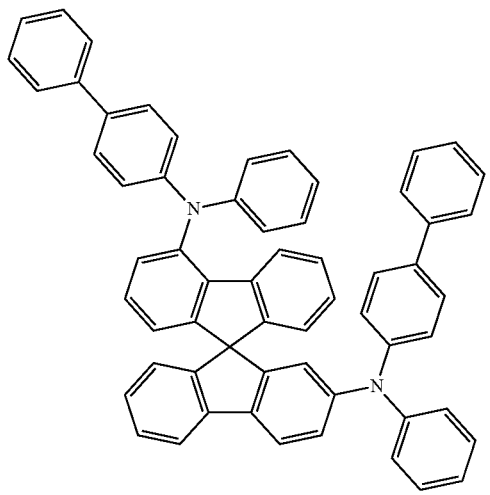
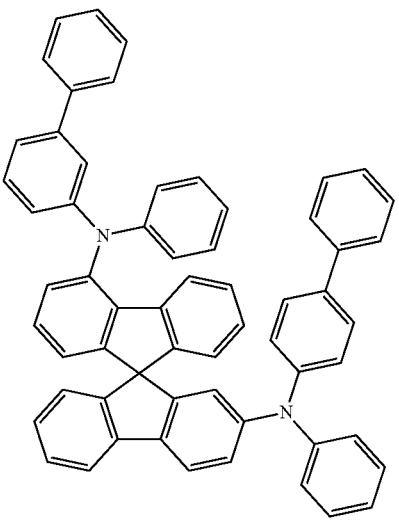
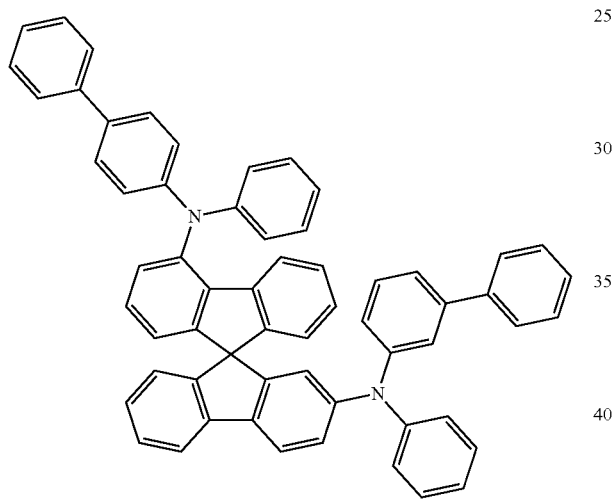
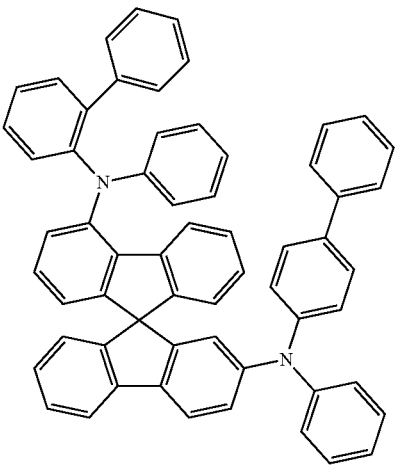
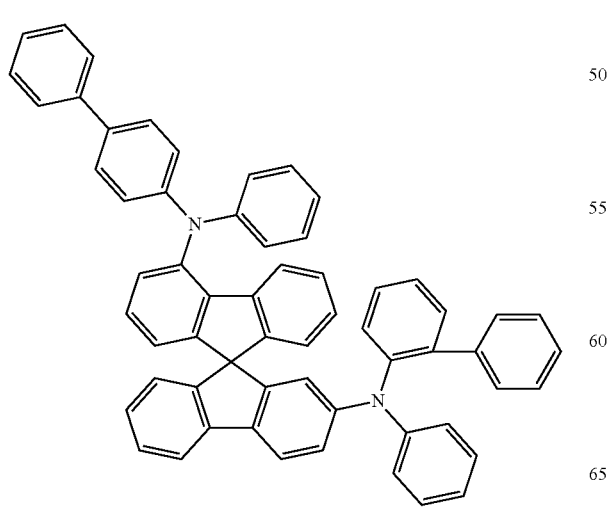
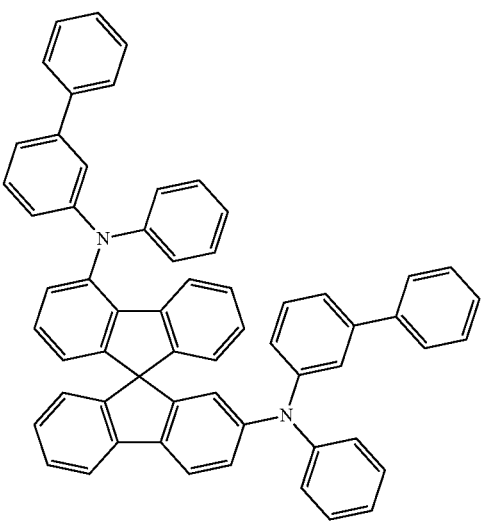

31
-continued
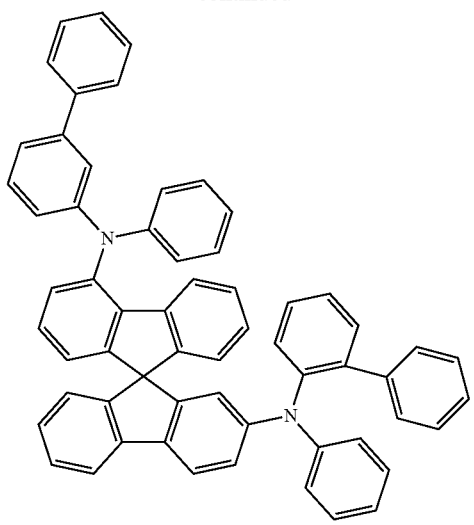
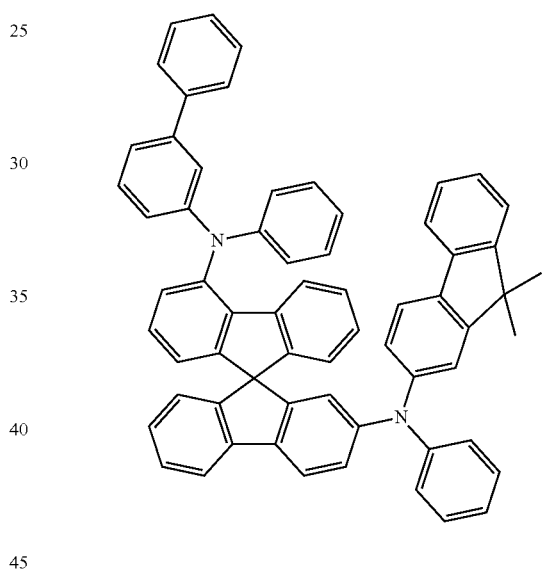
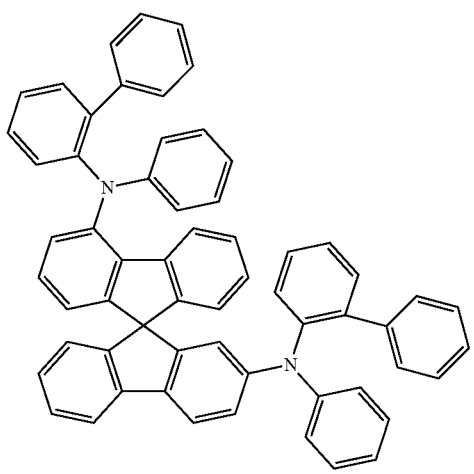
32
-continued
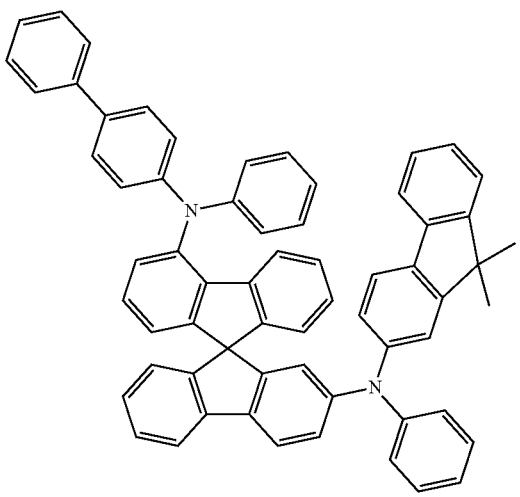
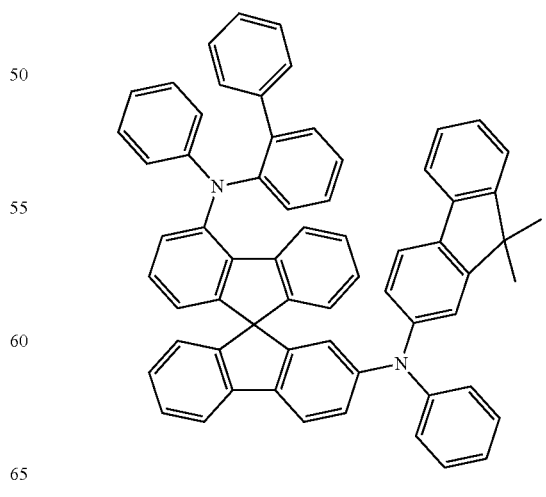

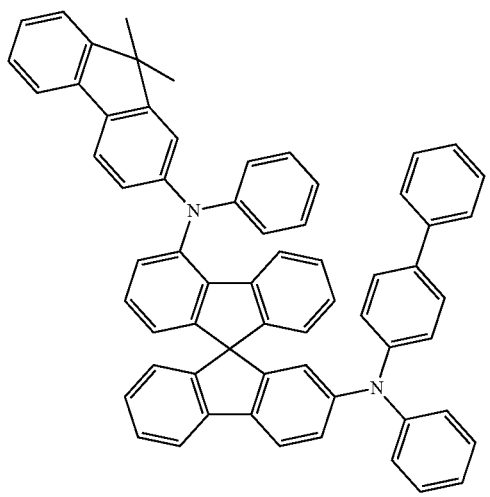
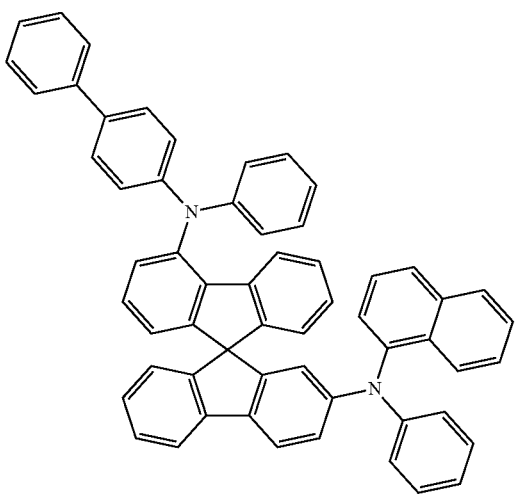
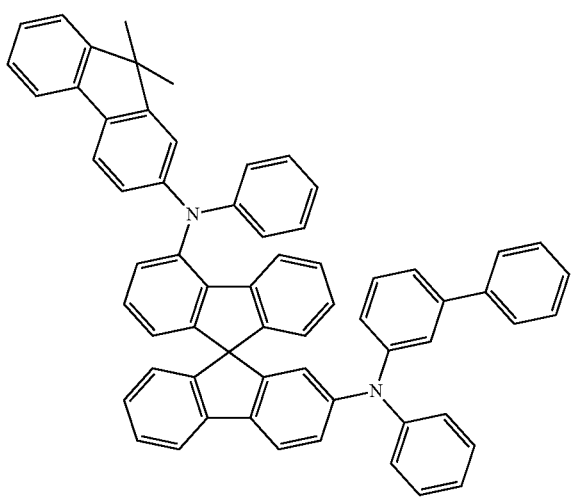
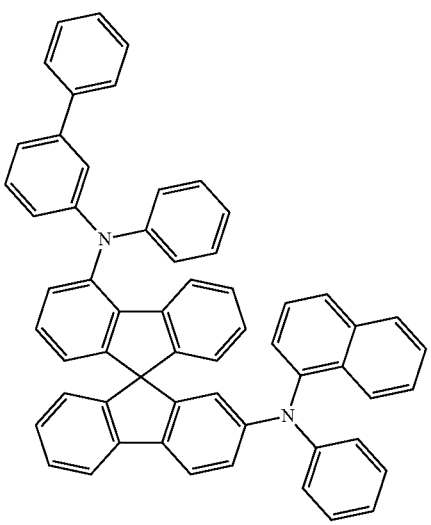
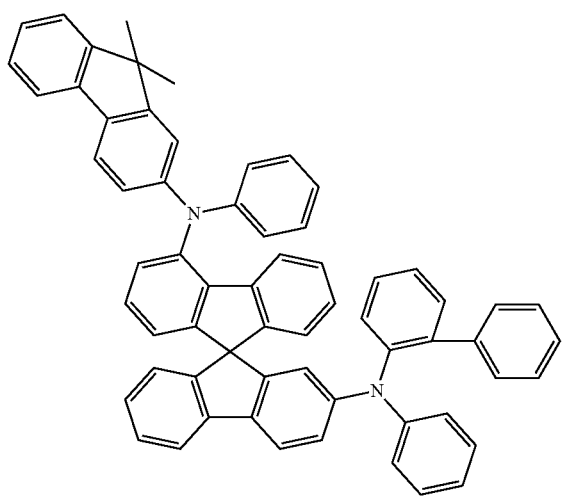
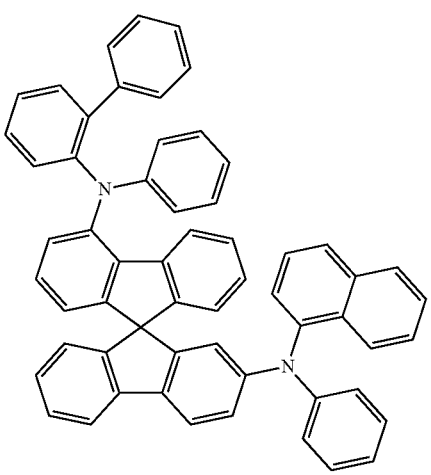

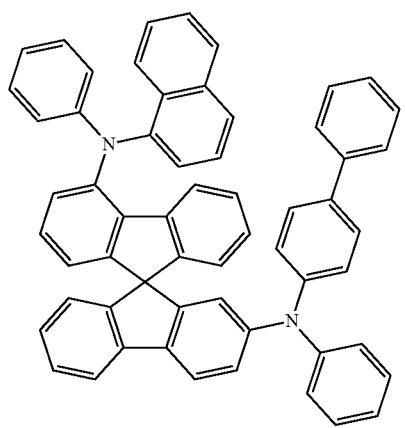
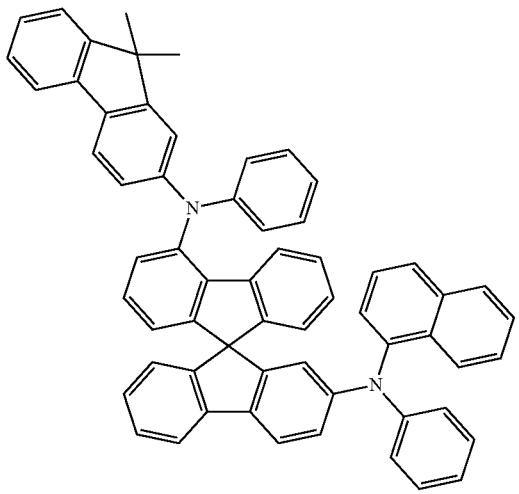
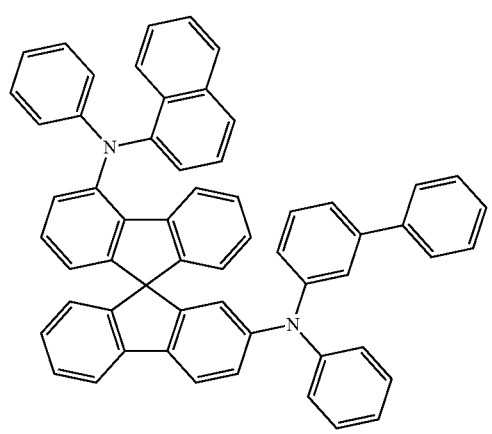
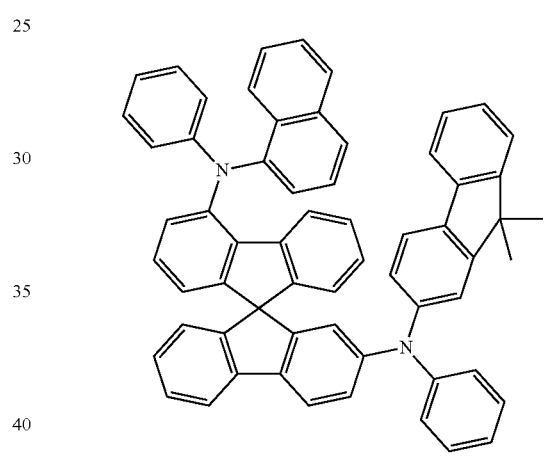
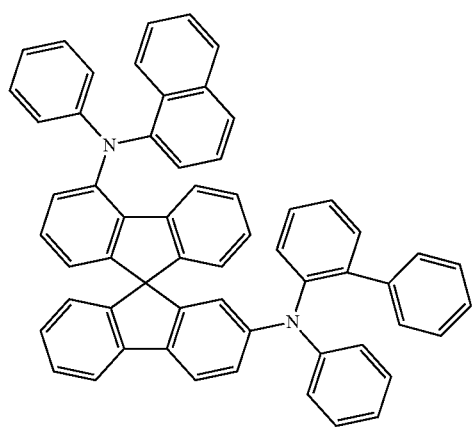
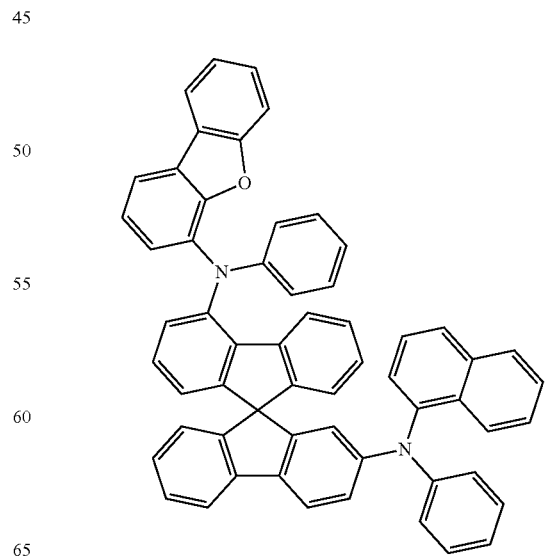

37
-continued
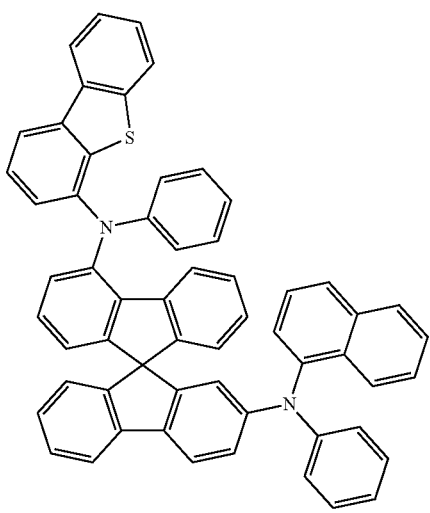
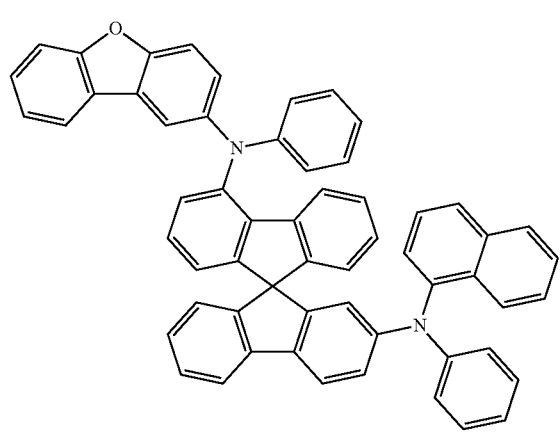
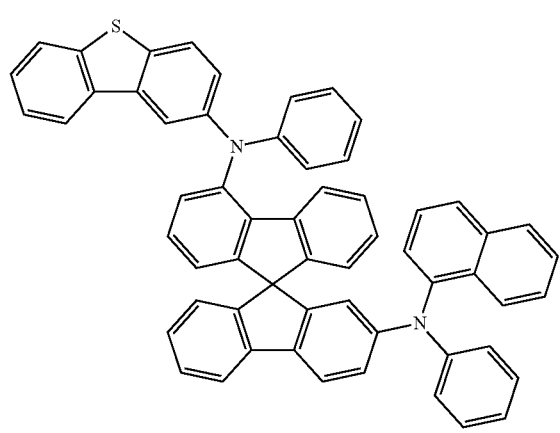
38
-continued
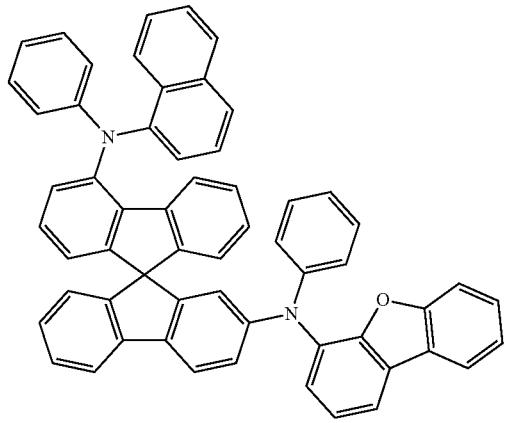
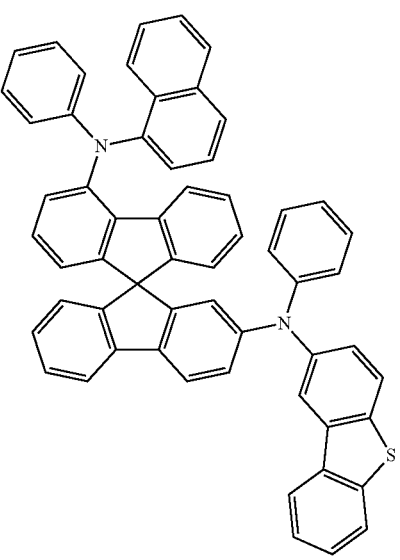
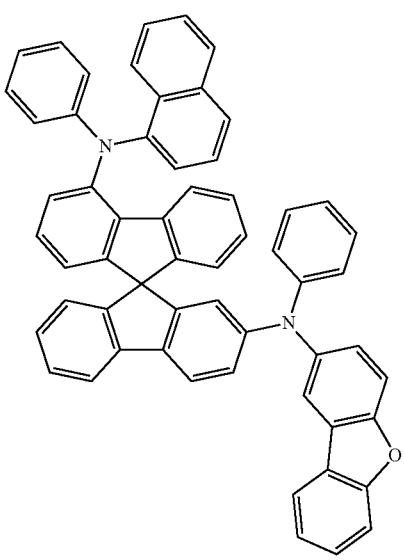

39
-continued
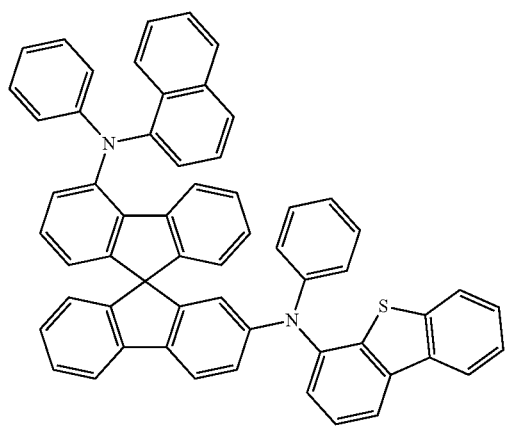
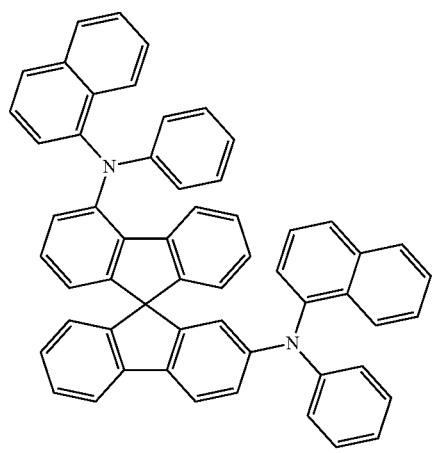
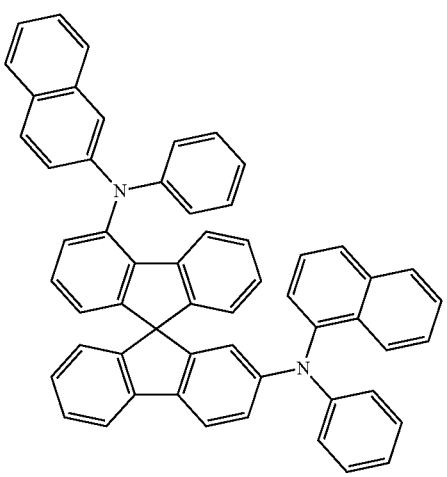
40
-continued
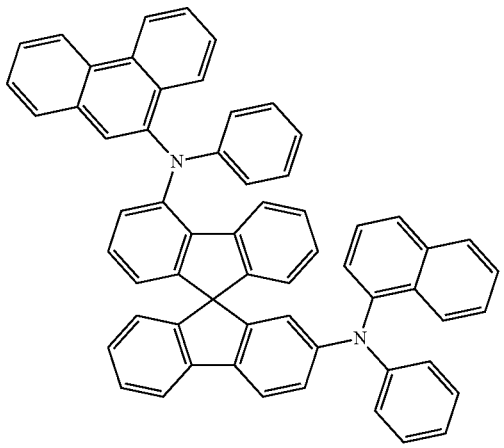
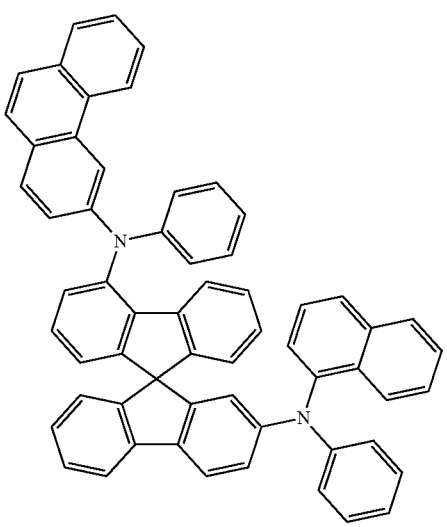
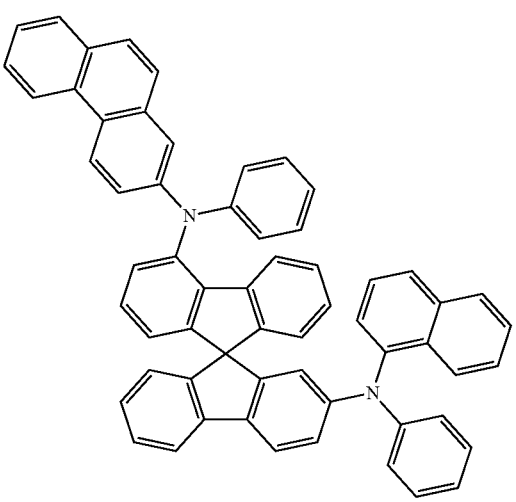

-continued
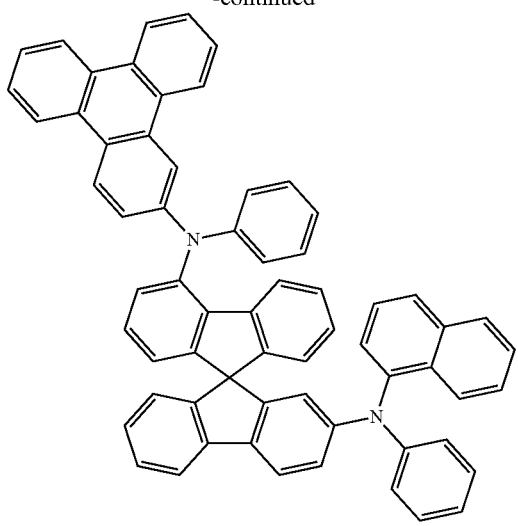
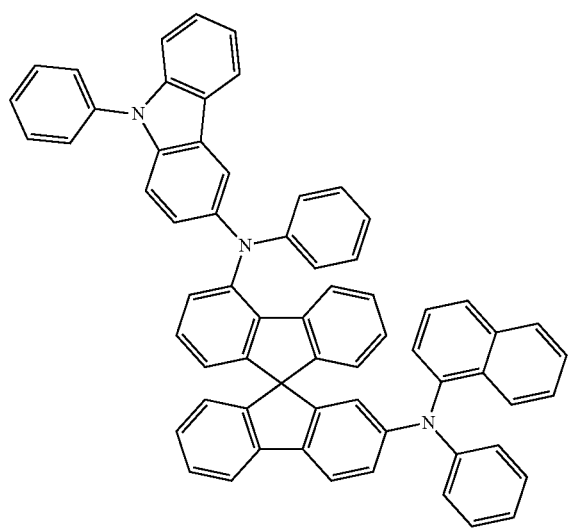
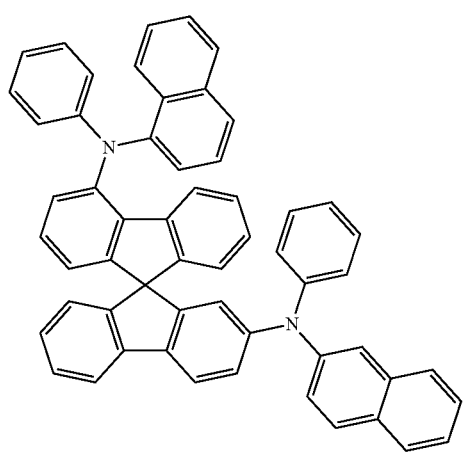
-continued
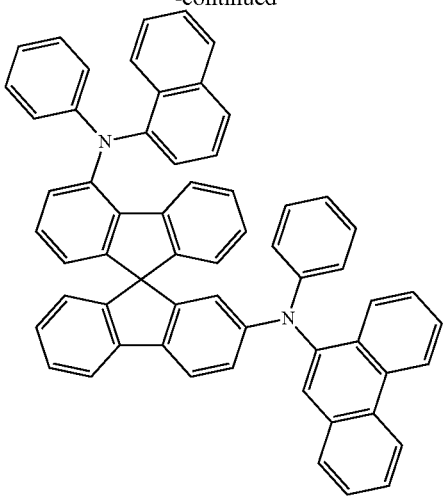
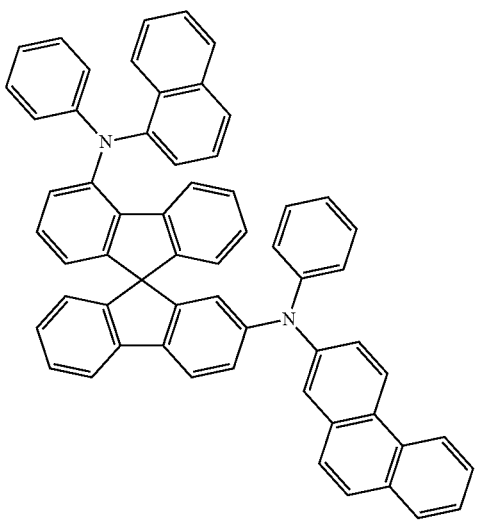
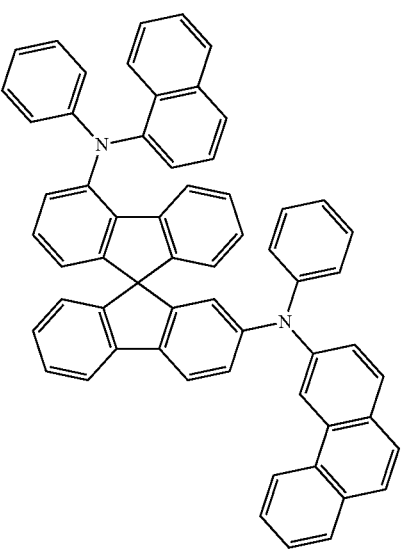

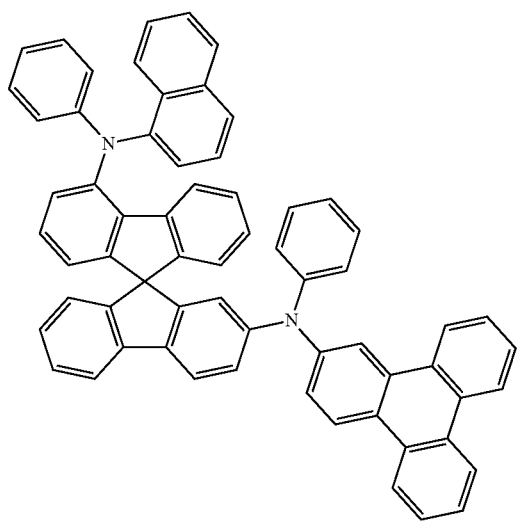
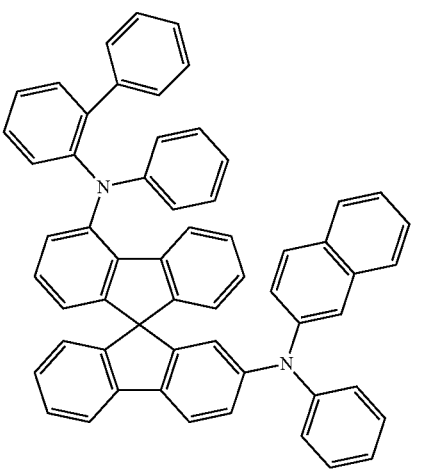
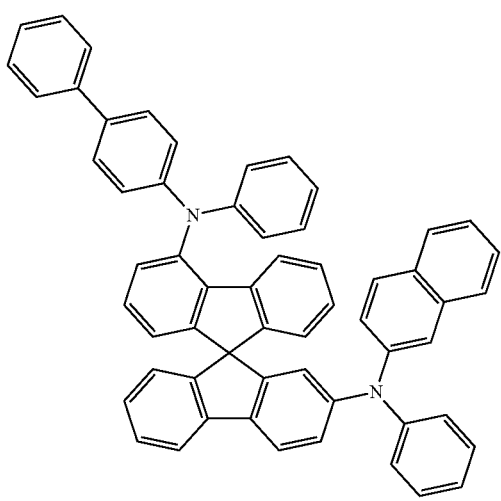
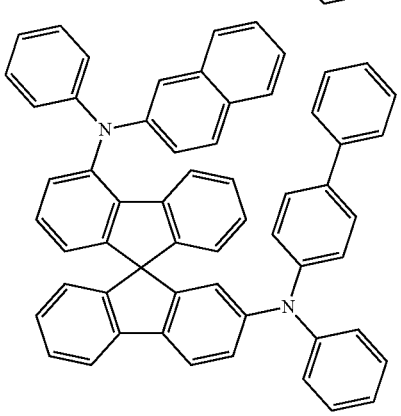
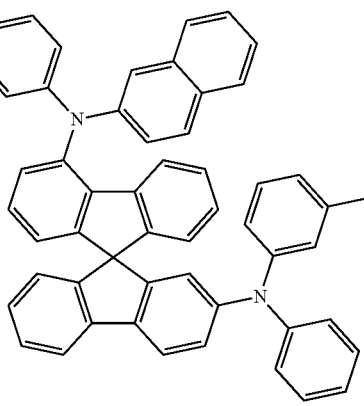
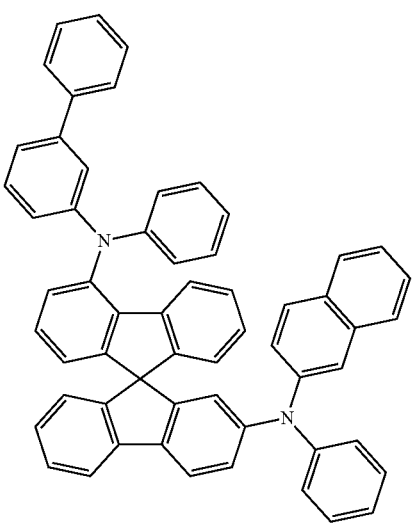
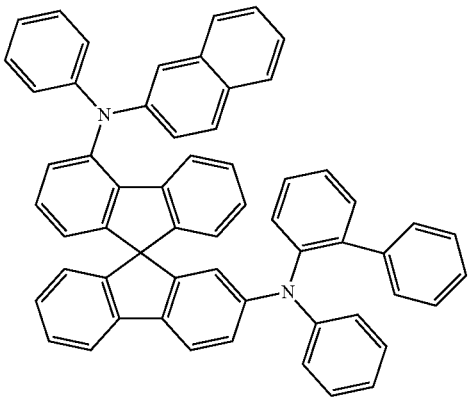

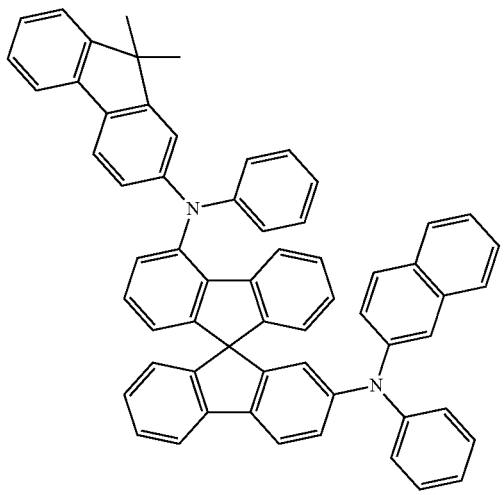
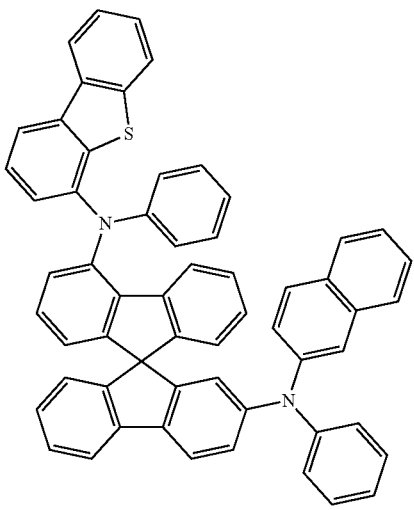
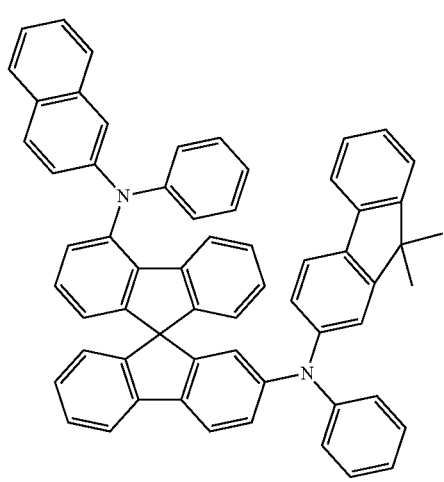
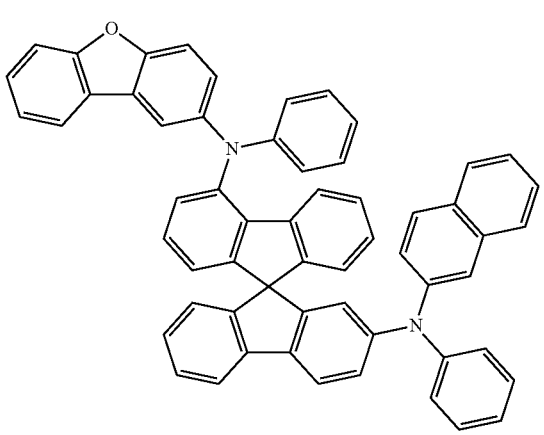
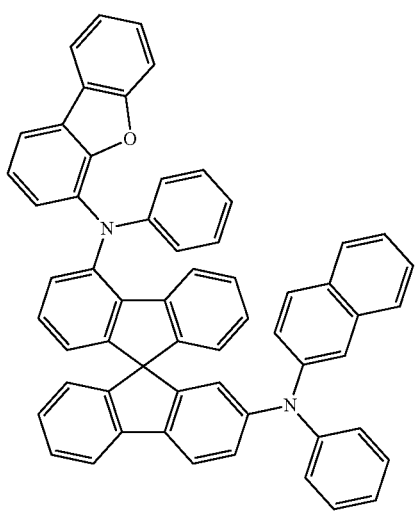
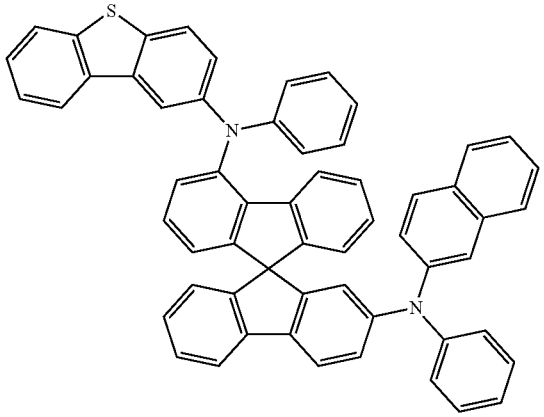

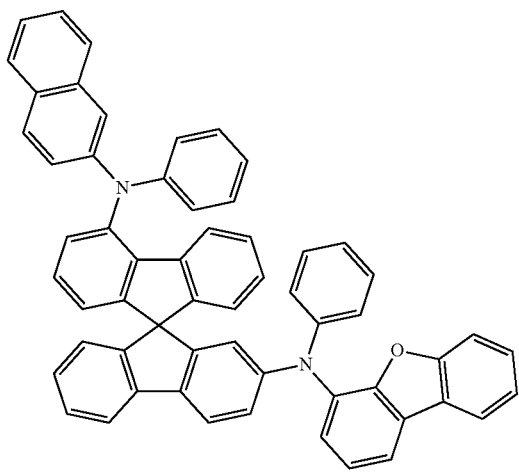
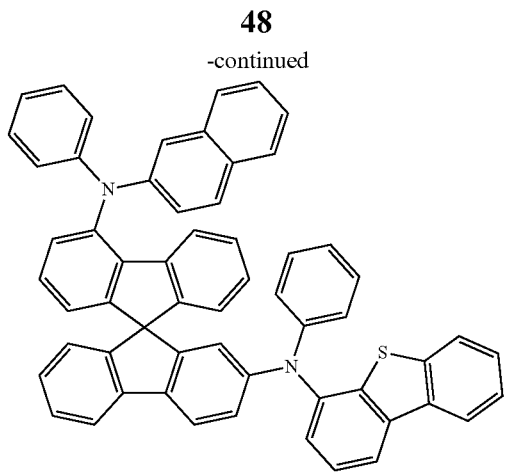
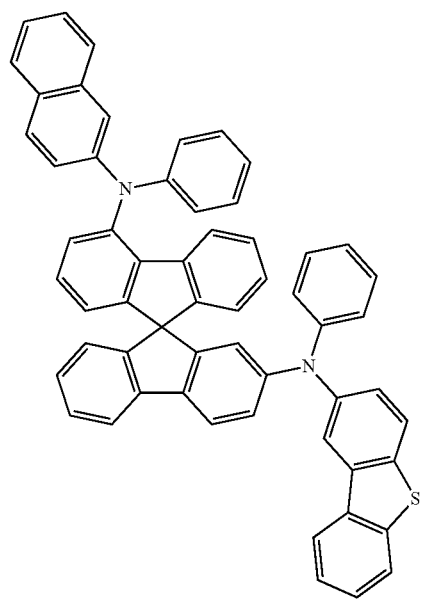
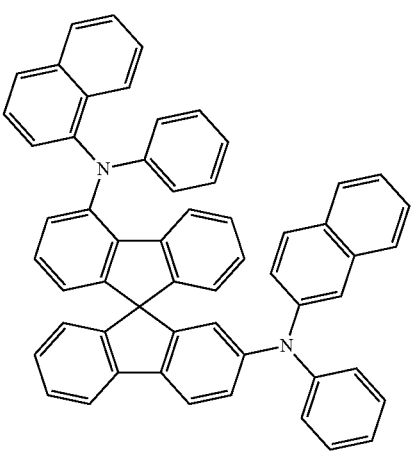
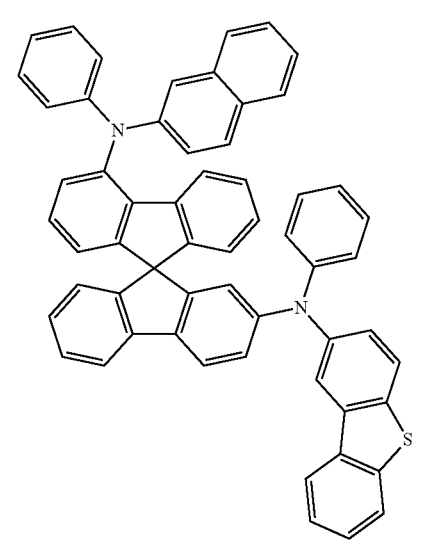
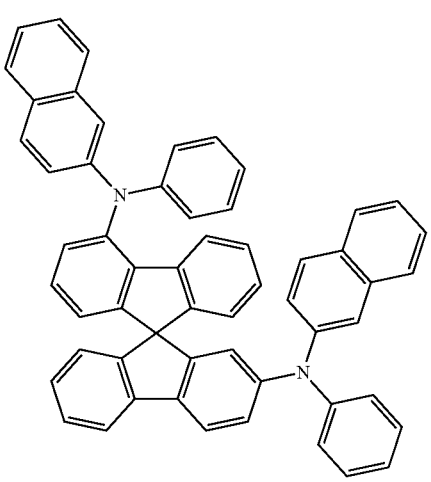

49
-continued
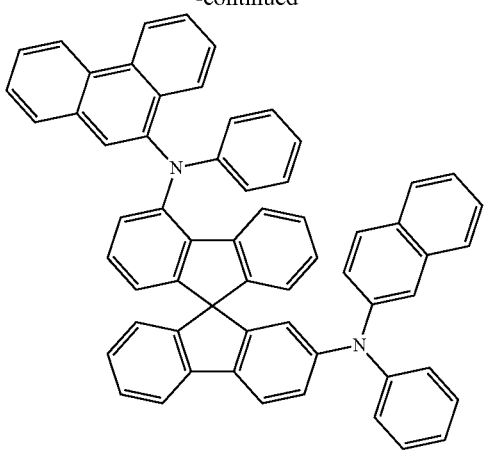
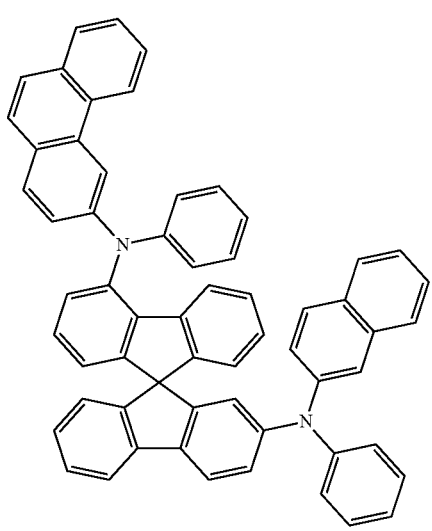
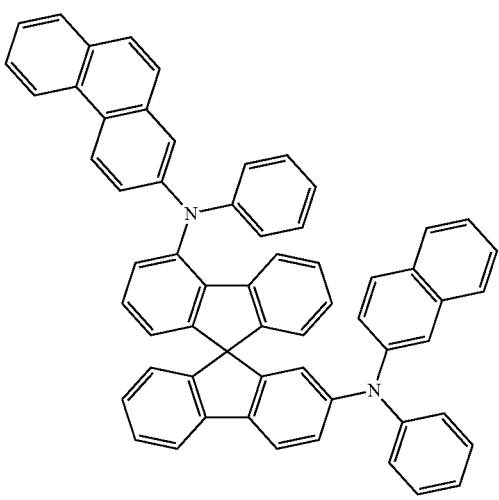
50
-continued
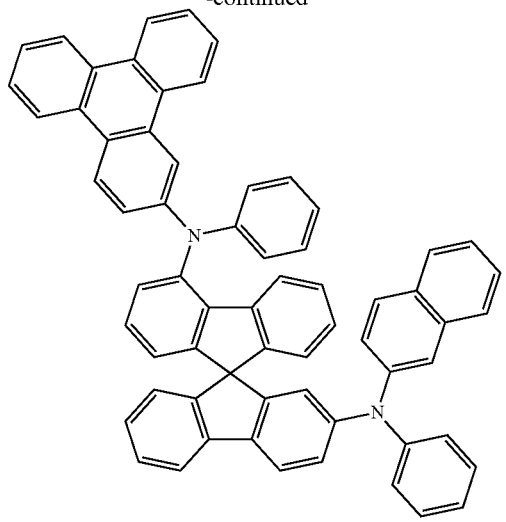
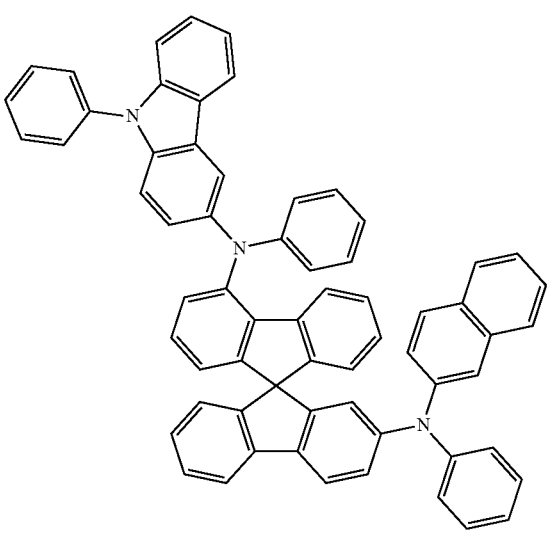
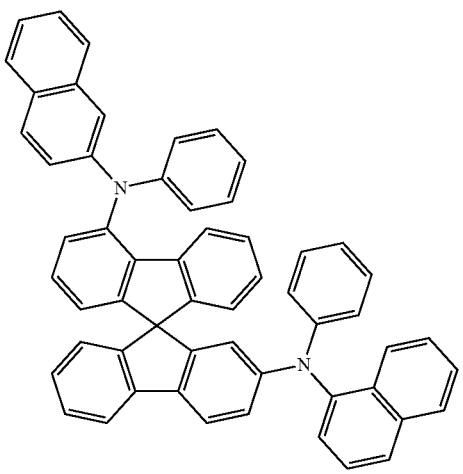

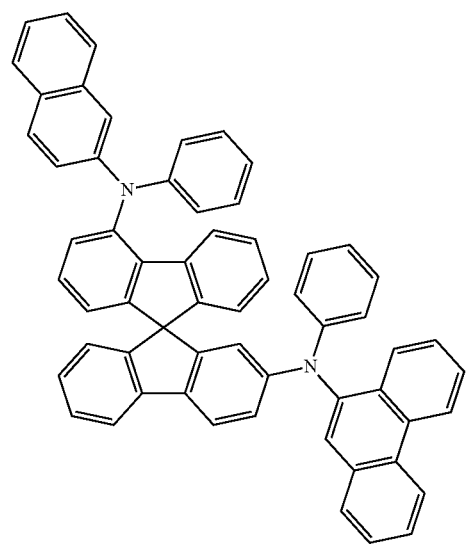
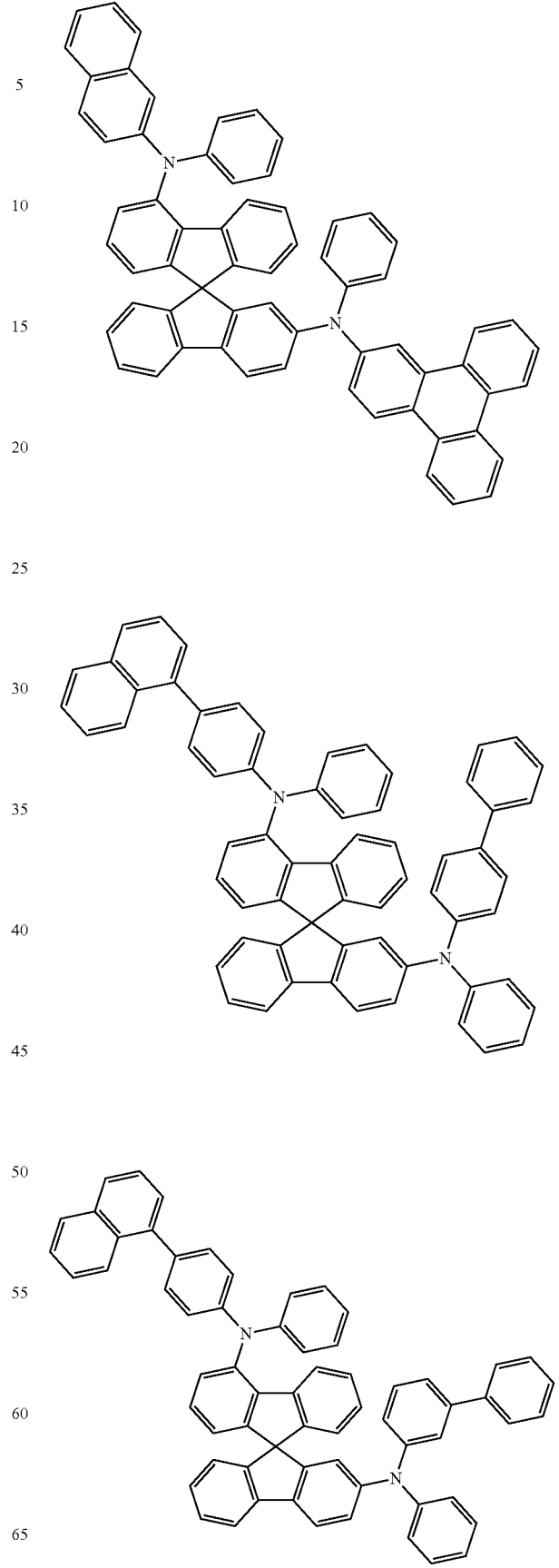

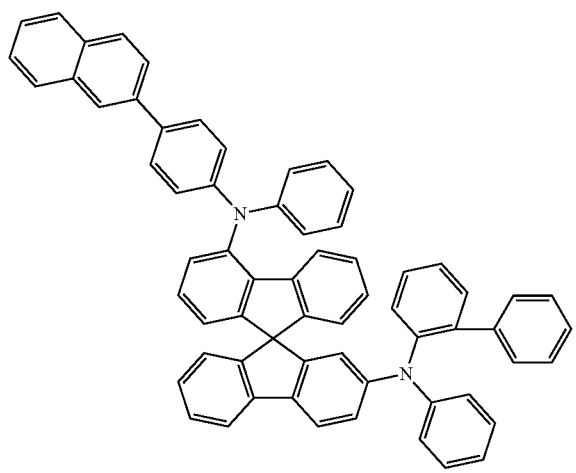
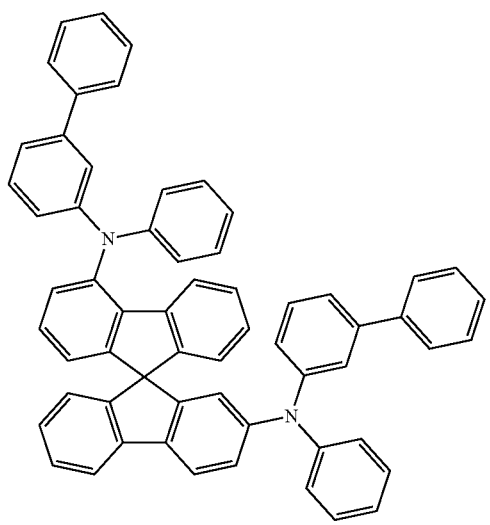
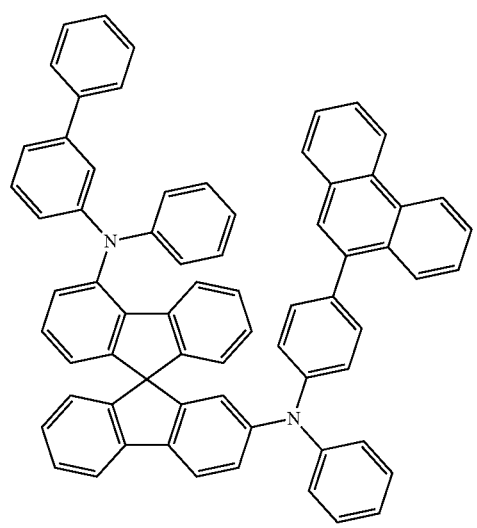
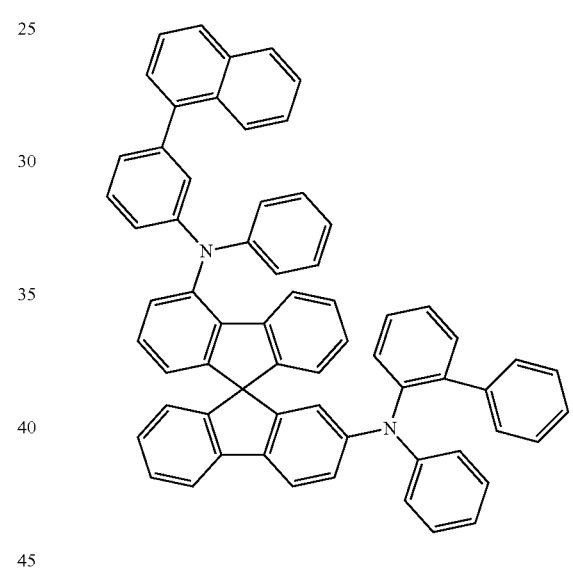
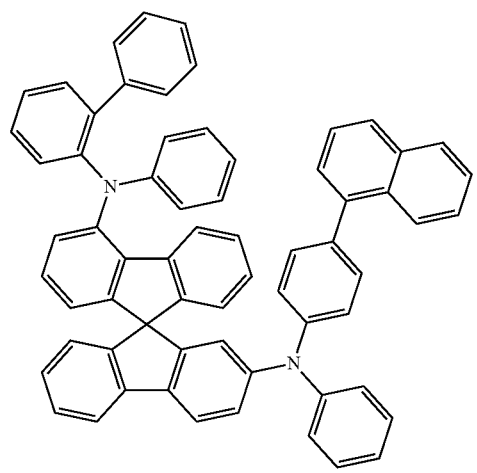
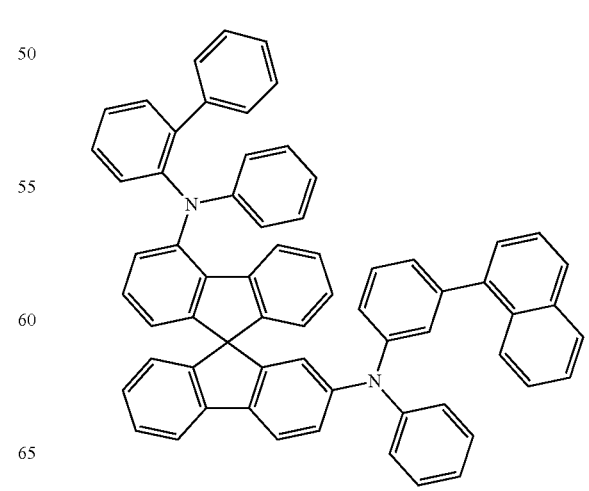

-continued
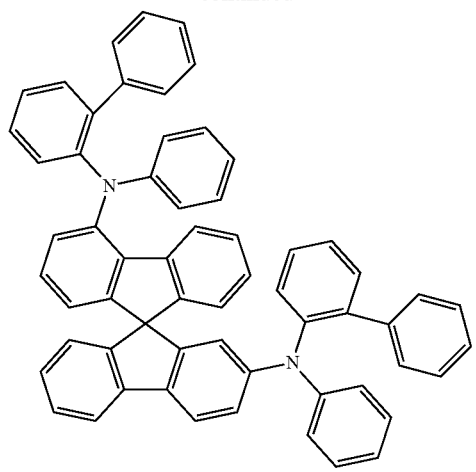
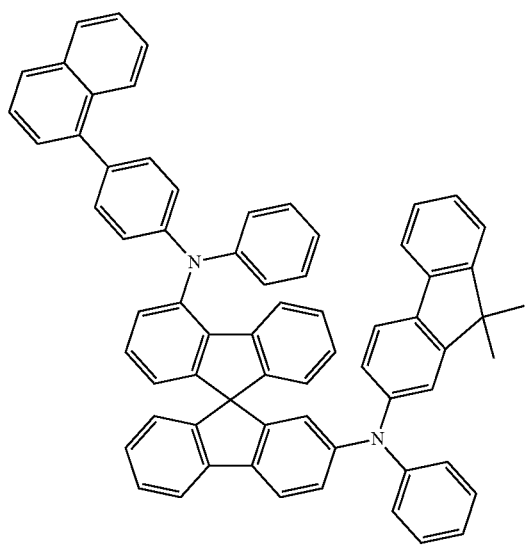
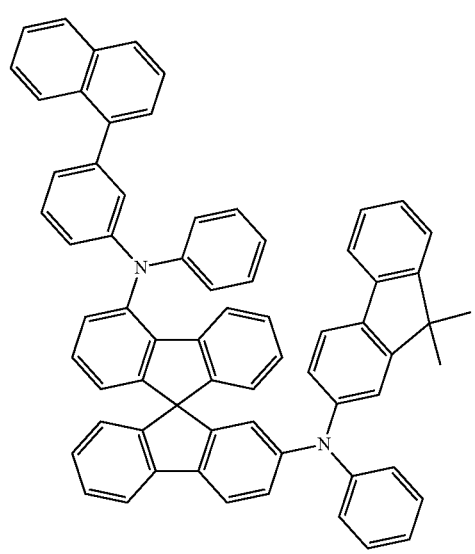
-continued
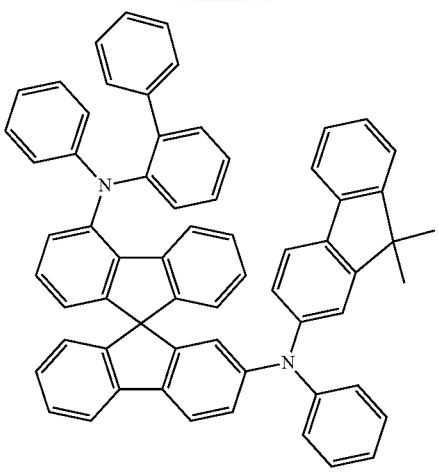
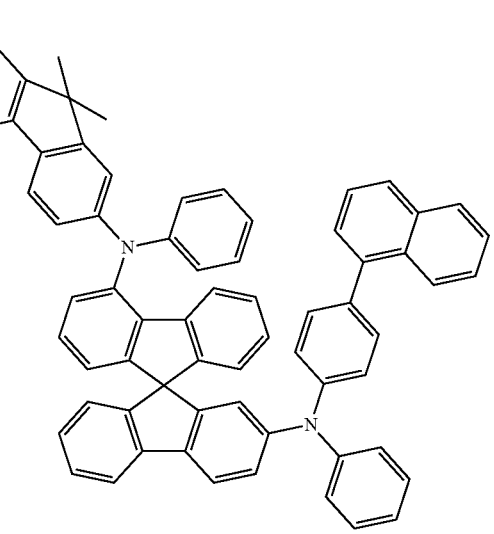
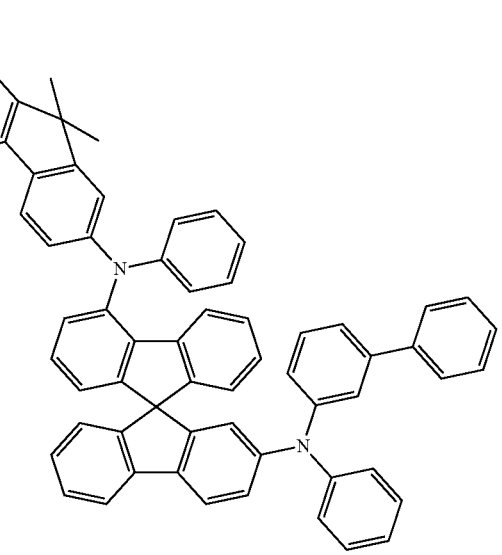

-continued
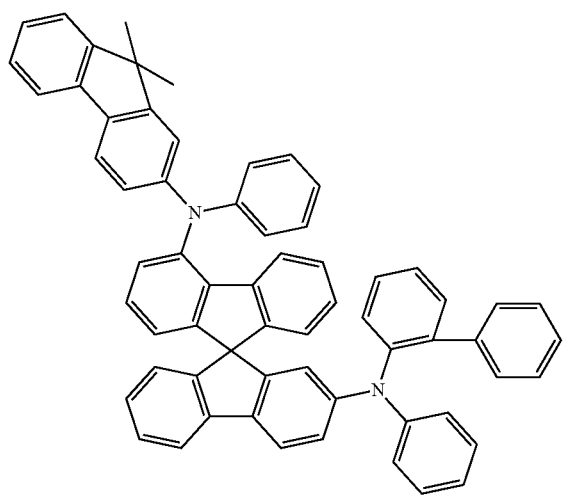
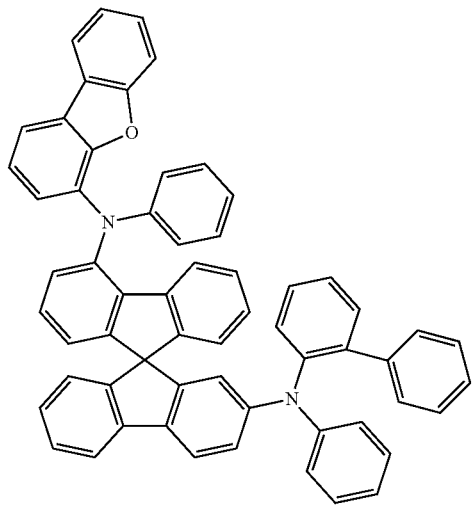
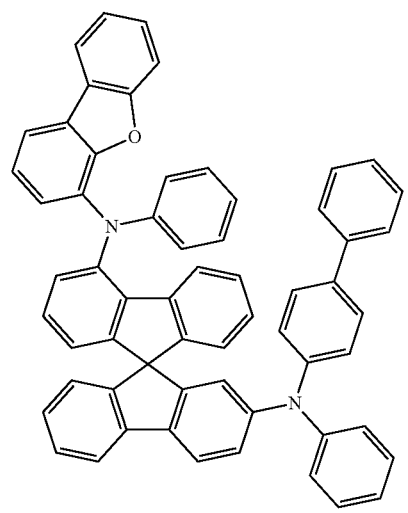
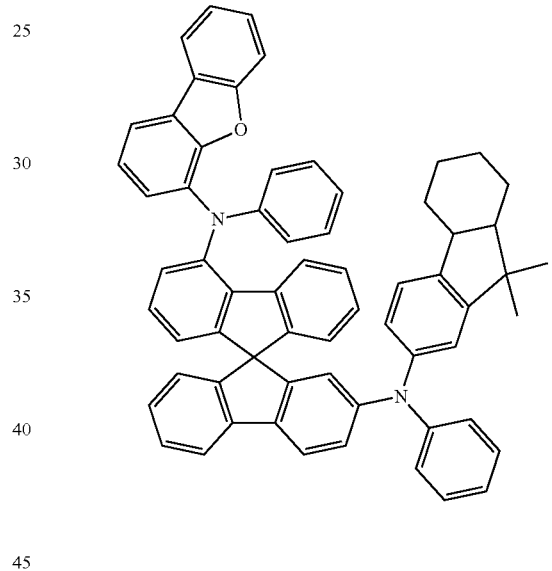
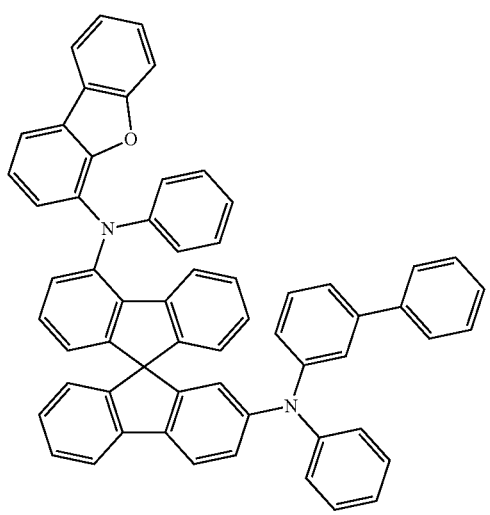
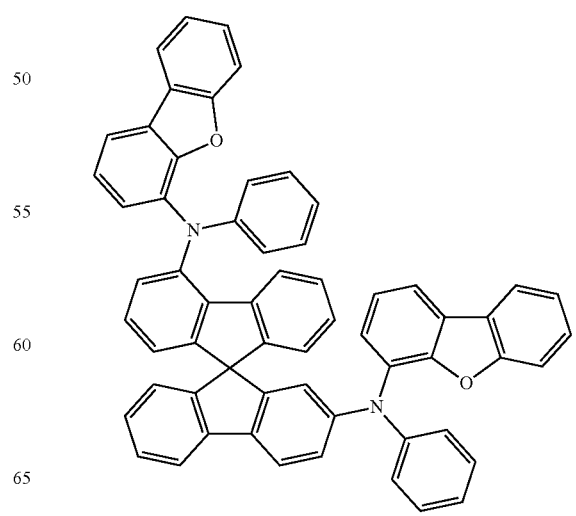

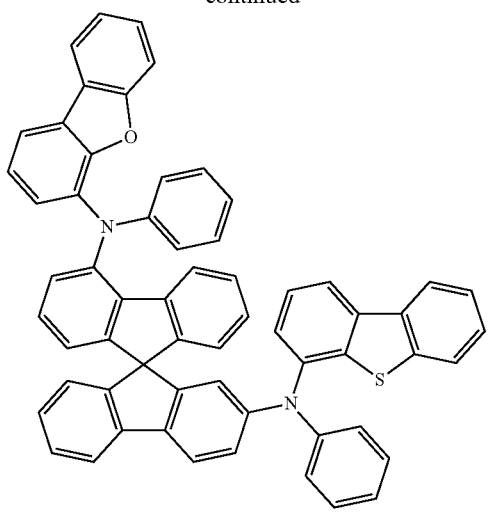
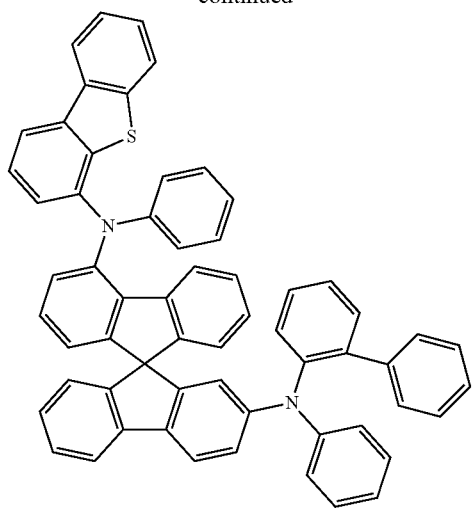
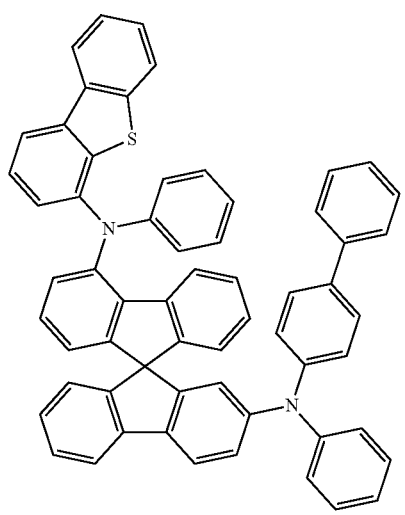
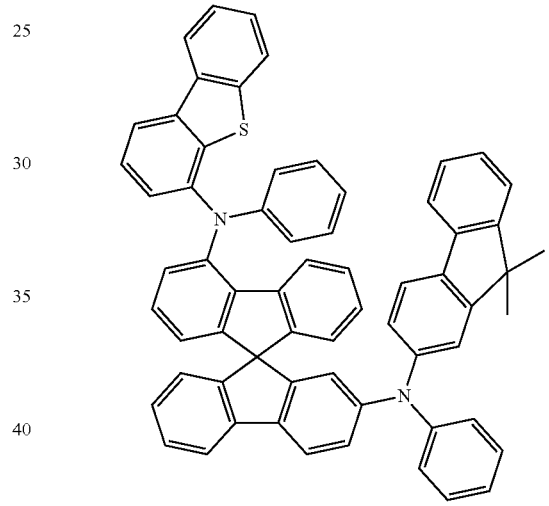
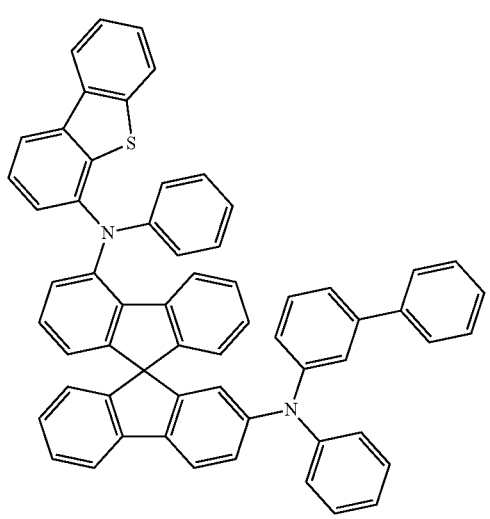
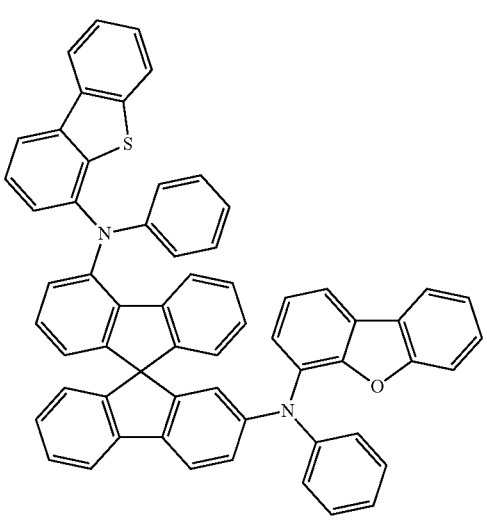

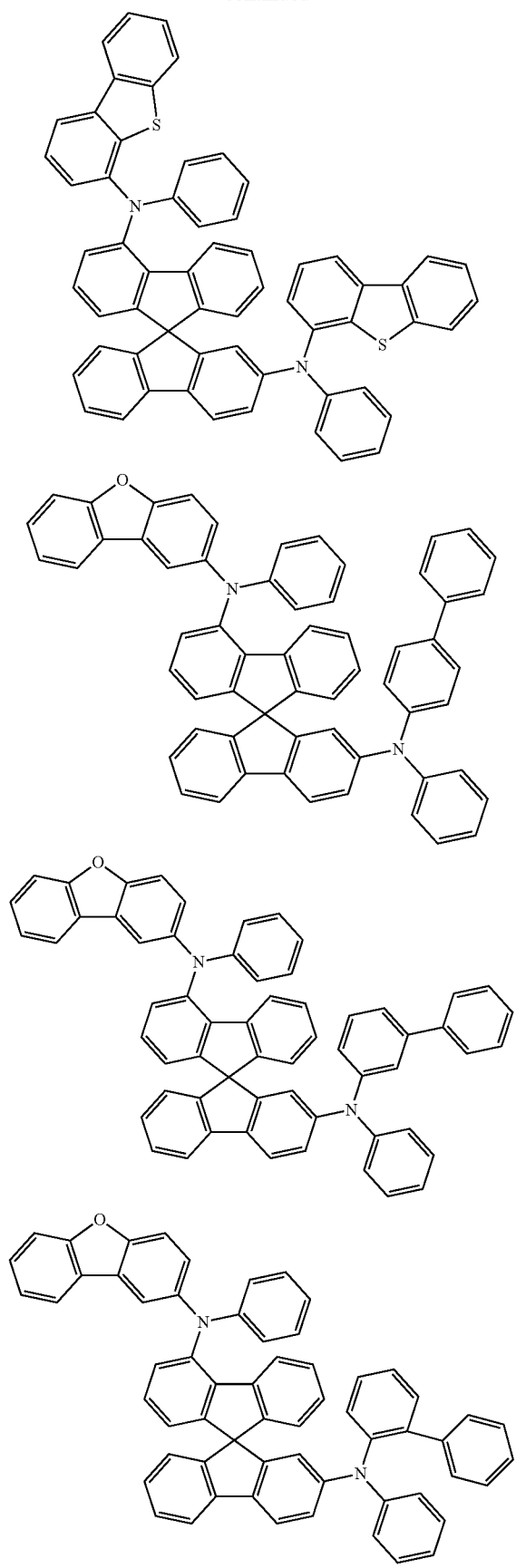
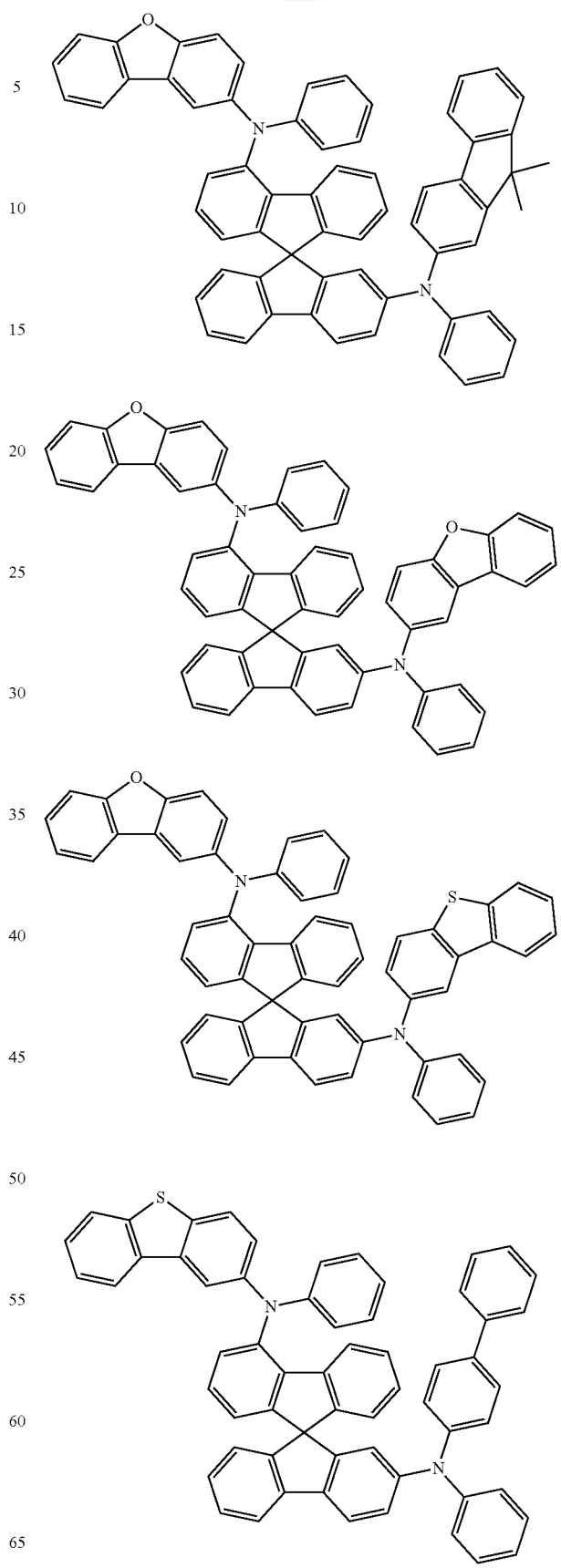

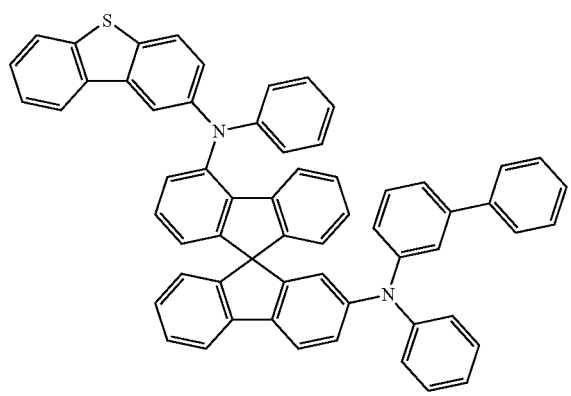
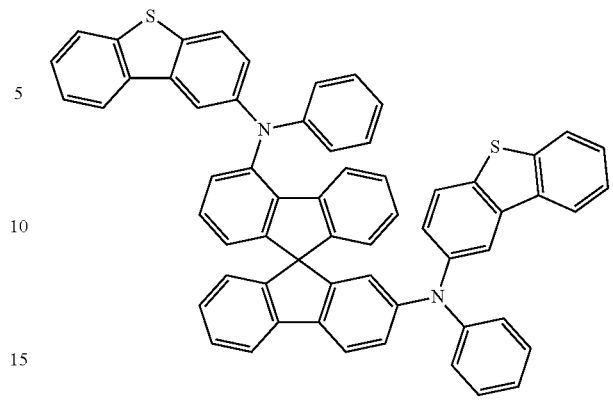
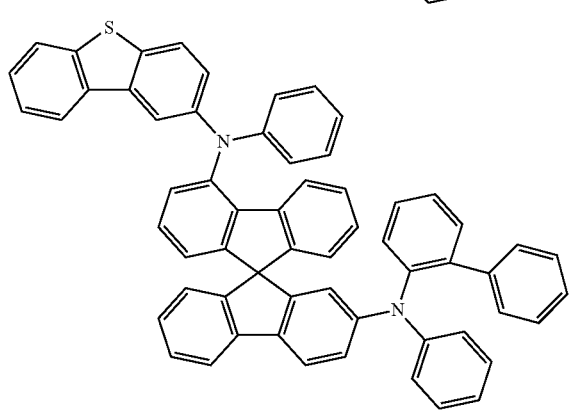
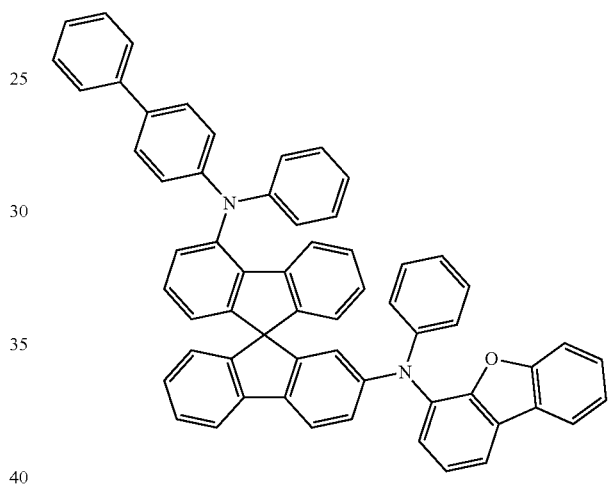
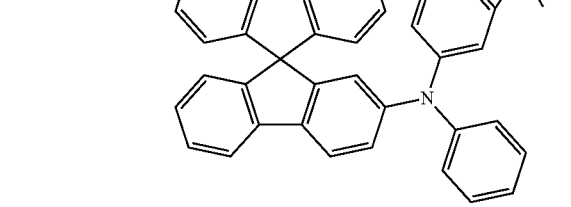
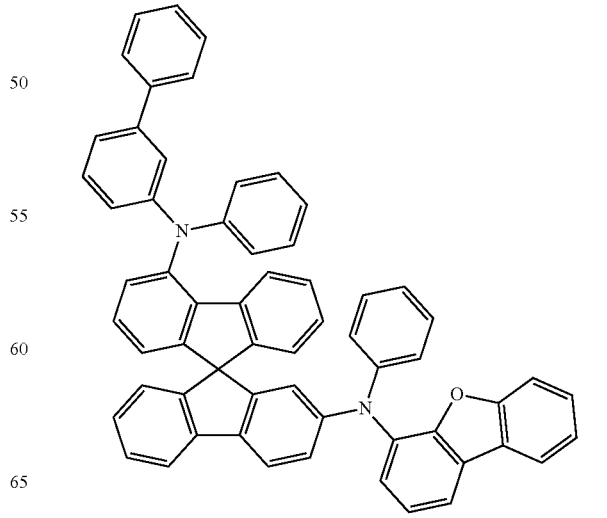

65
-continued
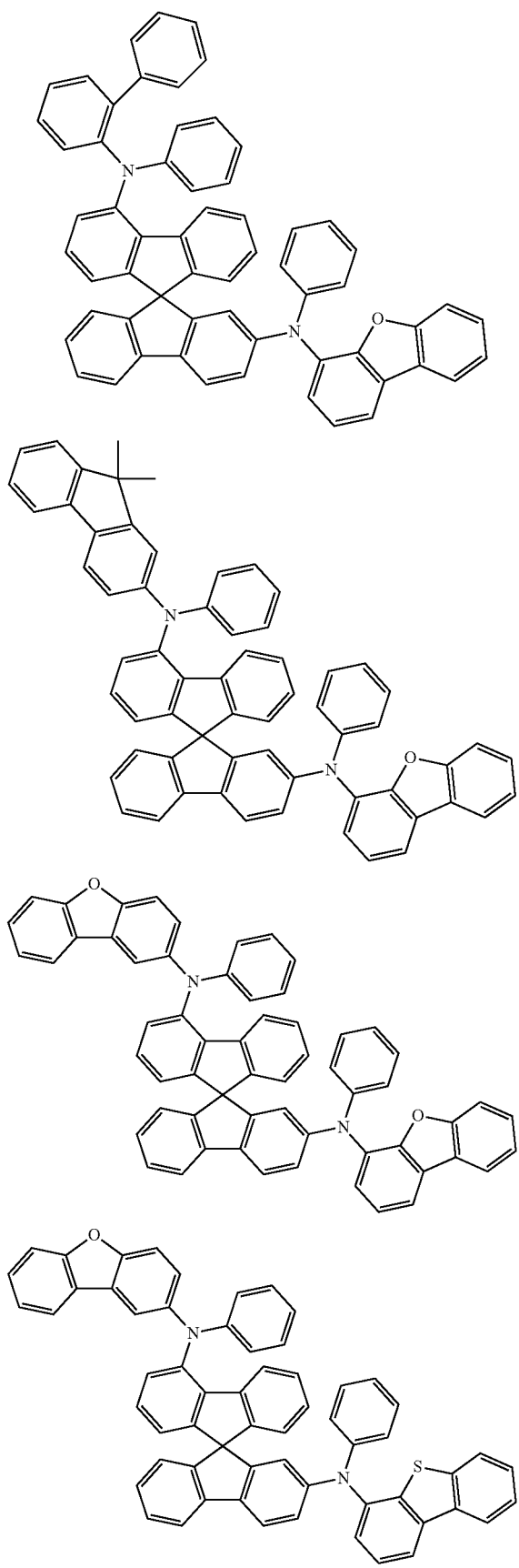 [SMILES: c1ccc(-c2ccccc2N(c2ccccc2)c2cccc3c2-c2ccccc2C32c3ccccc3-c3ccc(N(c4ccccc4)c4cccc5c4oc4ccccc45)cc32)cc1 ; CC1(C)c2ccccc2-c2ccc(N(c3ccccc3)c3cccc4c3-c3ccccc3C43c4ccccc4-c4ccc(N(c5ccccc5)c5cccc6c5oc5ccccc56)cc43)cc21 ; c1ccc(N(c2ccc3oc4ccccc4c3c2)c2cccc3c2-c2ccccc2C32c3ccccc3-c3ccc(N(c4ccccc4)c4cccc5c4oc4ccccc45)cc32)cc1 ; c1ccc(N(c2ccc3oc4ccccc4c3c2)c2cccc3c2-c2ccccc2C32c3ccccc3-c3ccc(N(c4ccccc4)c4cccc5c4sc4ccccc45)cc32)cc1]
66
-continued
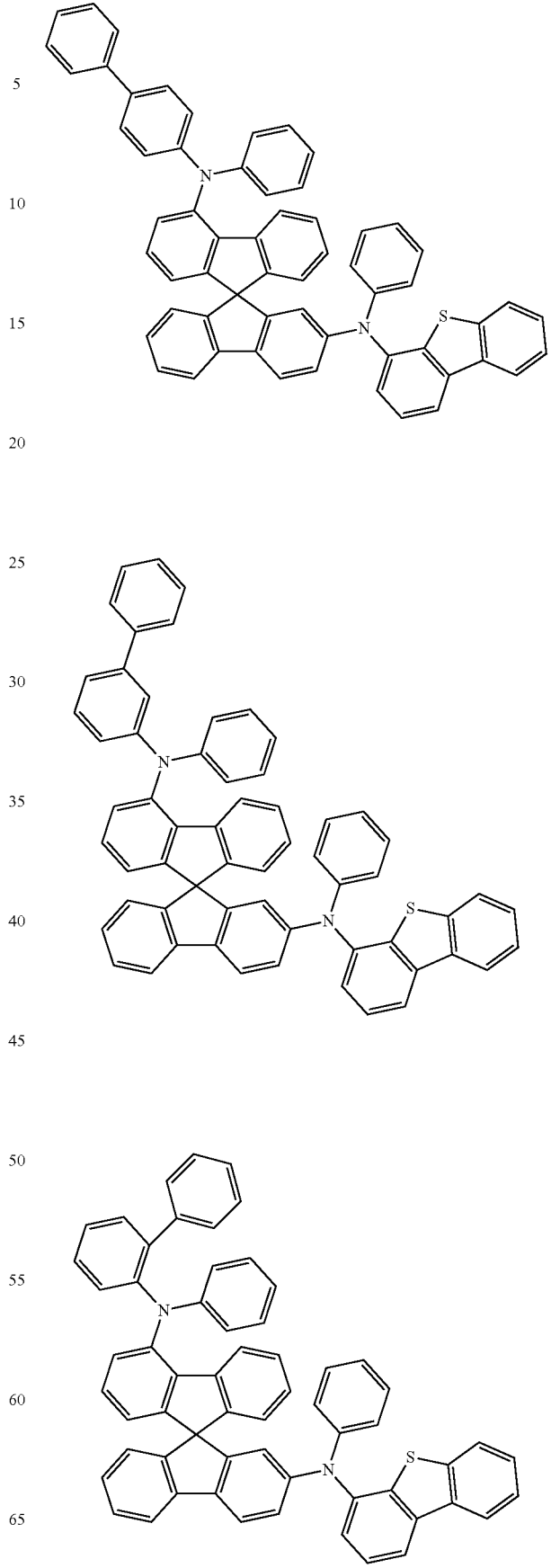

67
-continued
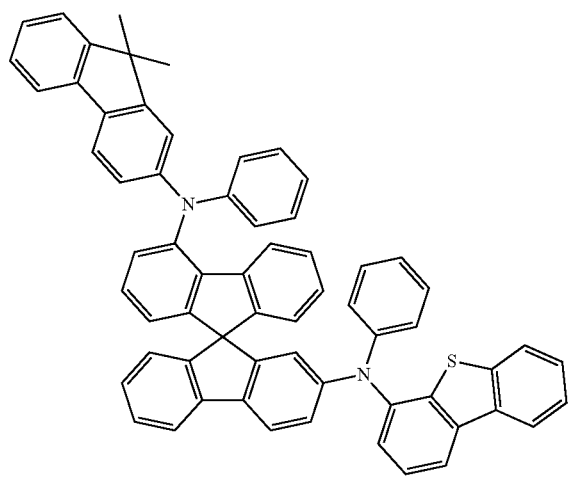
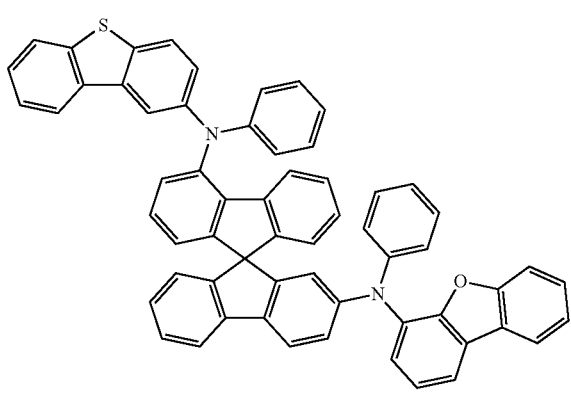
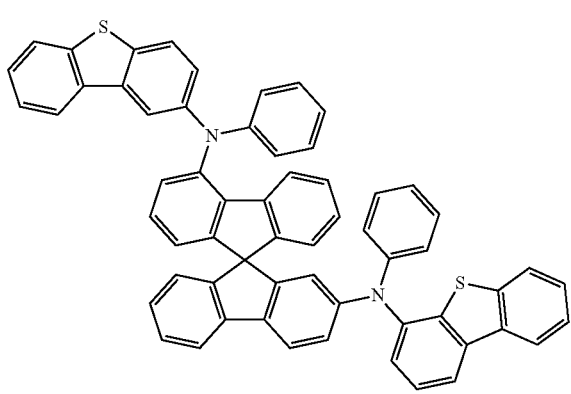
68
-continued
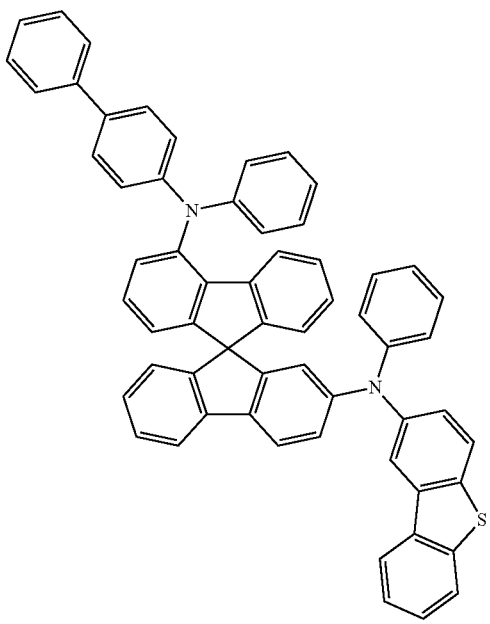
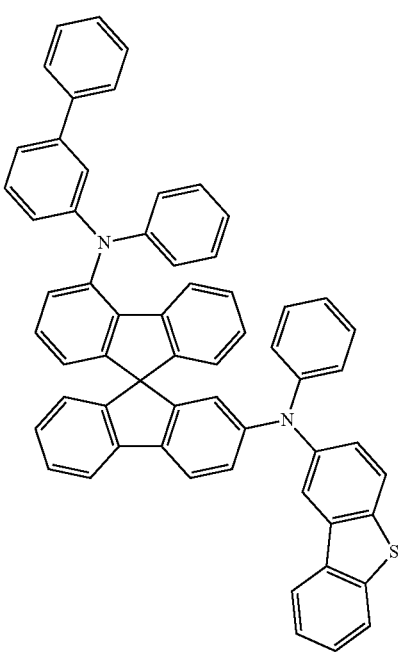

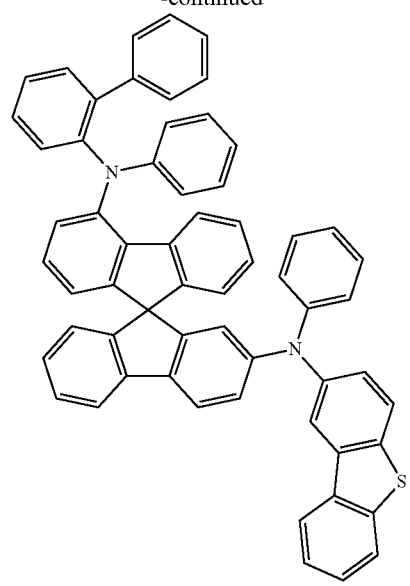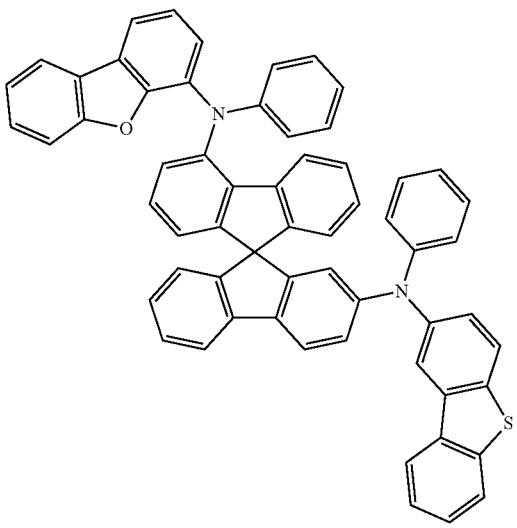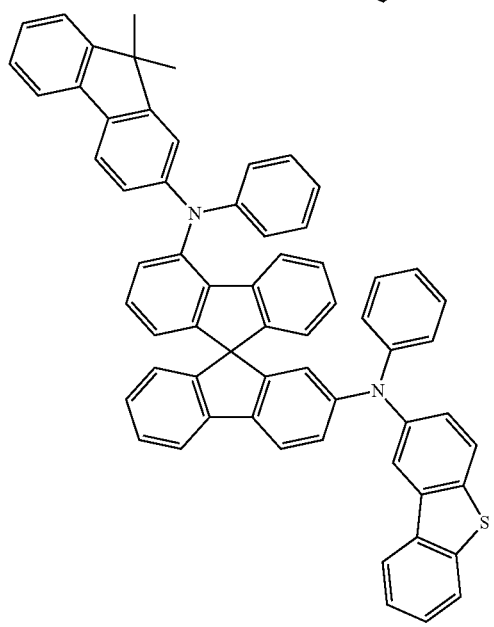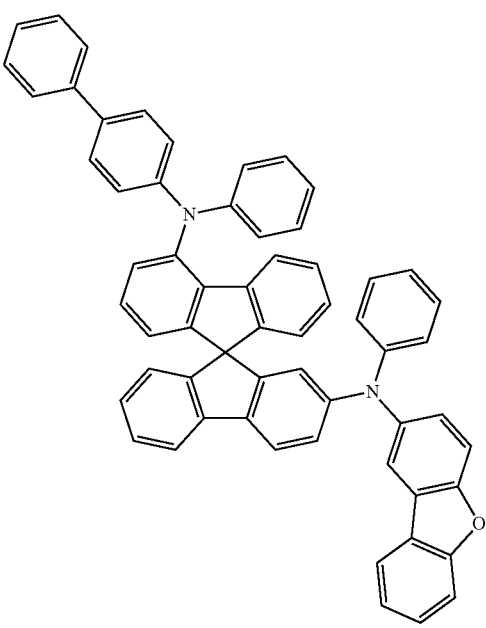

71
-continued
72
-continued
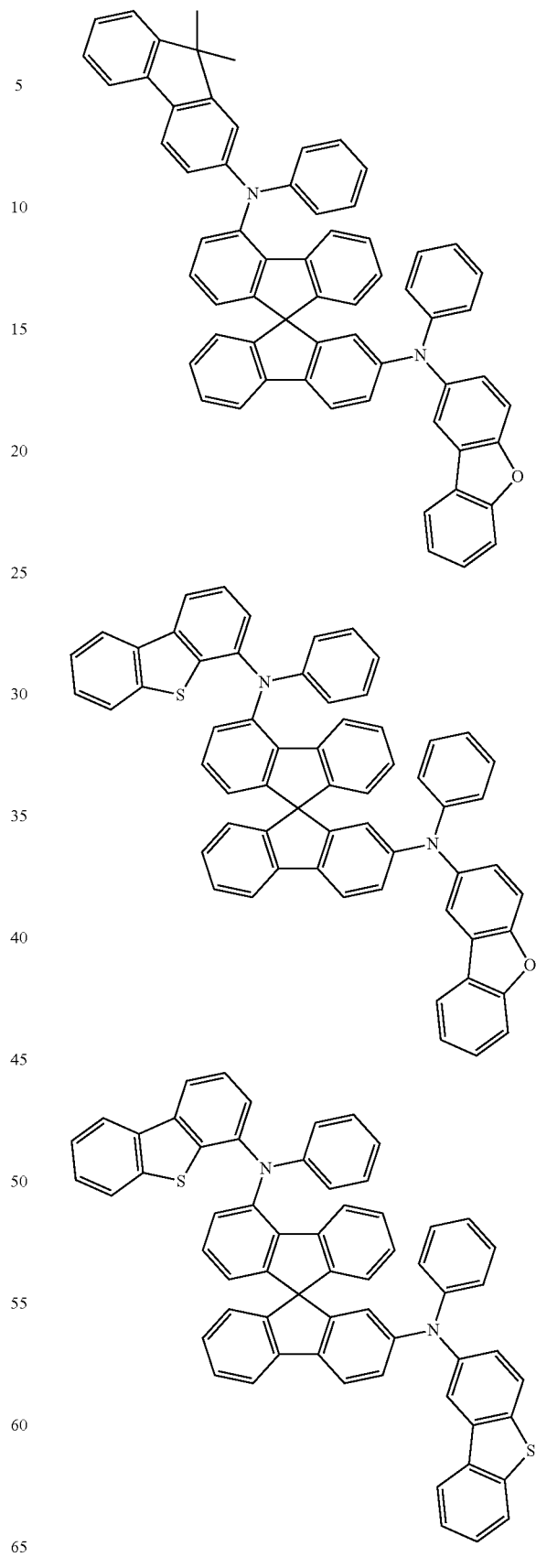

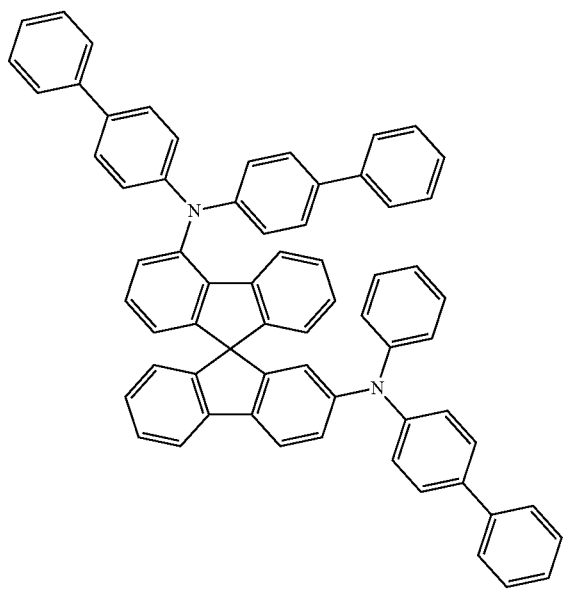
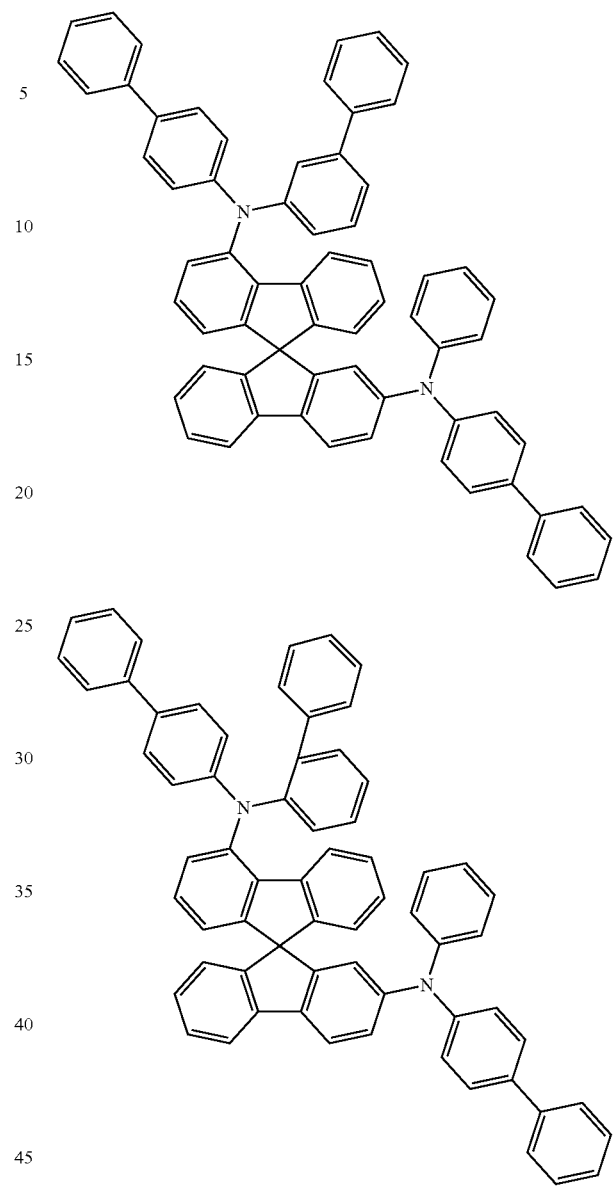
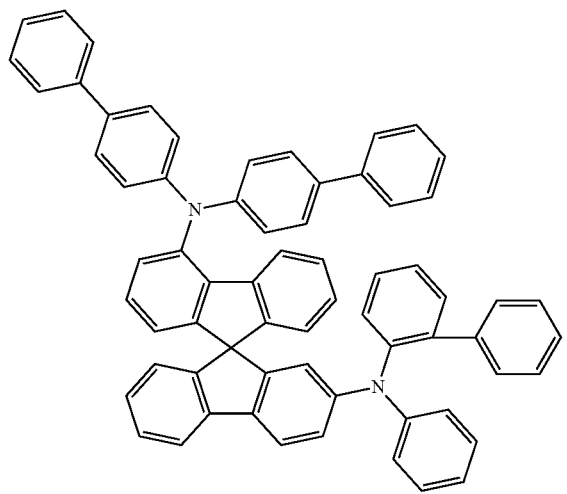
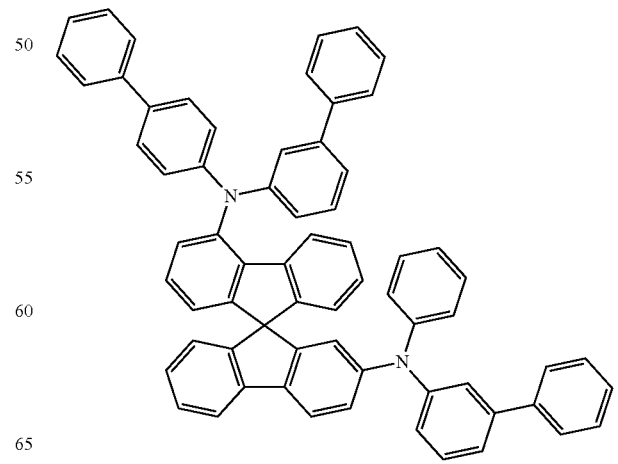

75
-continued
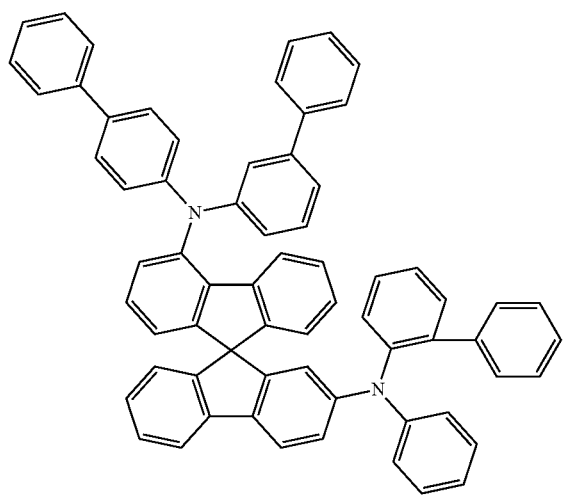
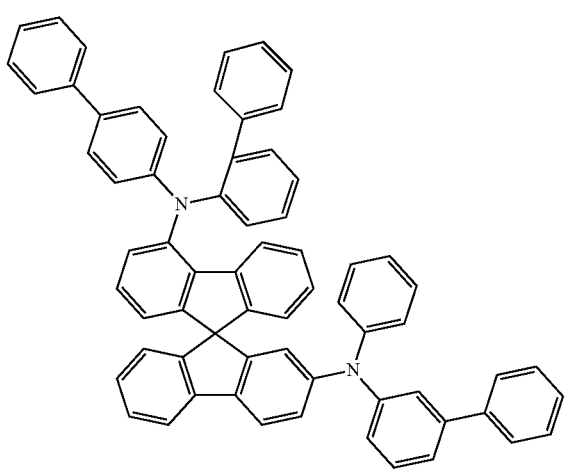
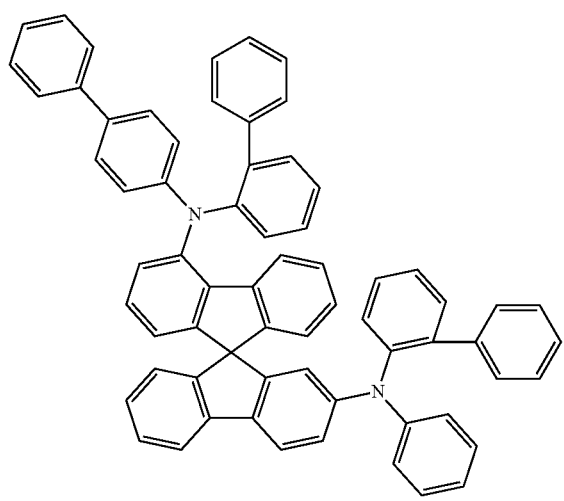
76
-continued
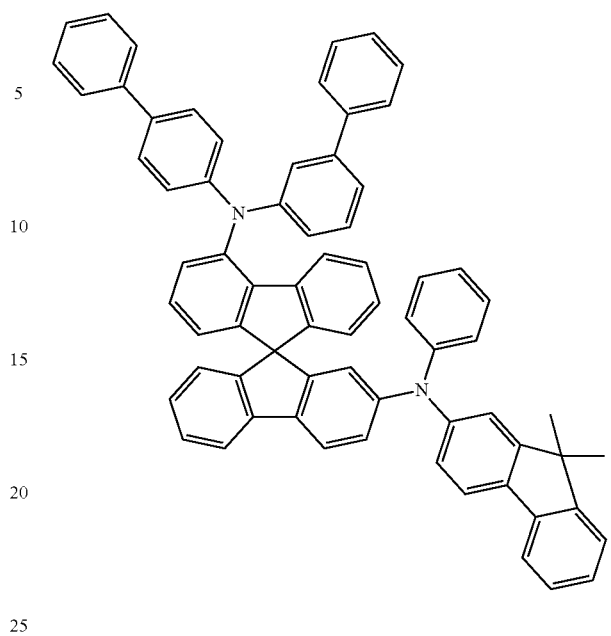
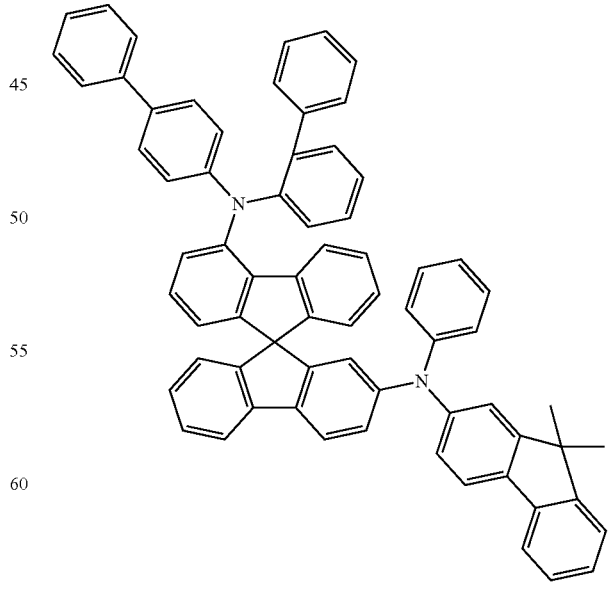

77
-continued
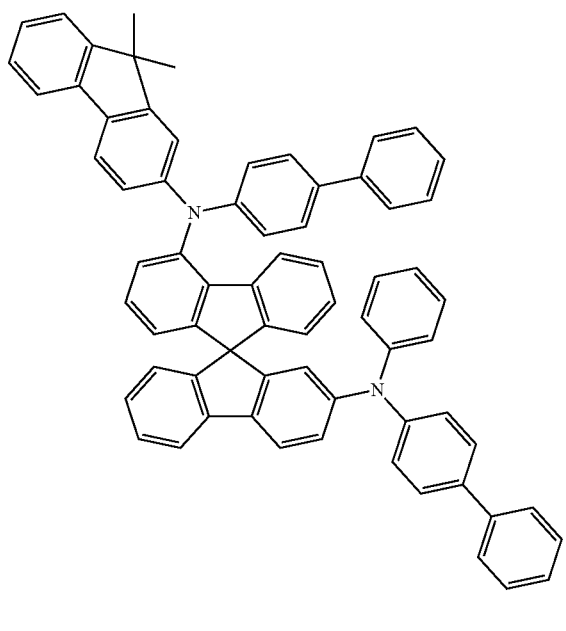
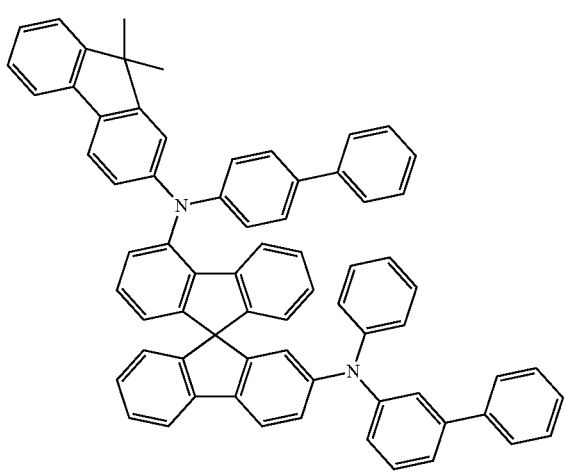
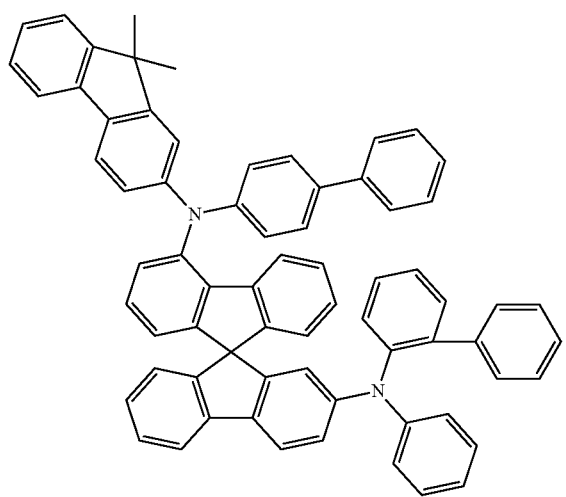
78
-continued
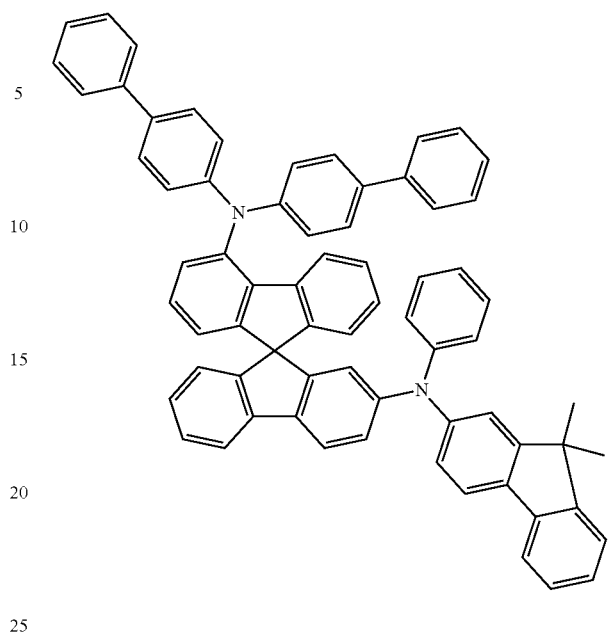
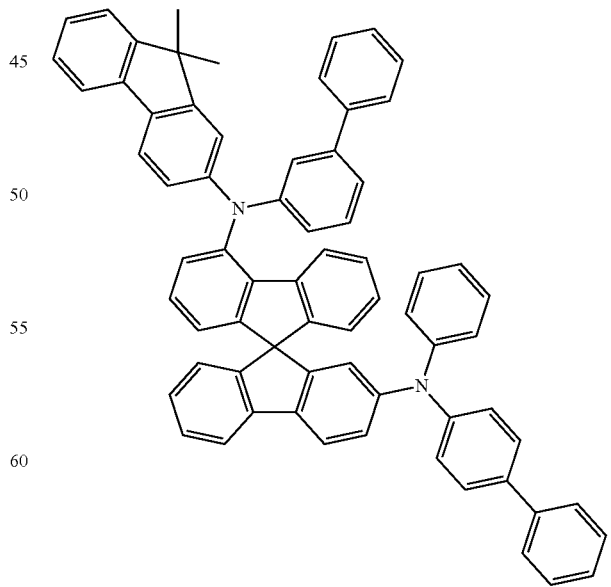

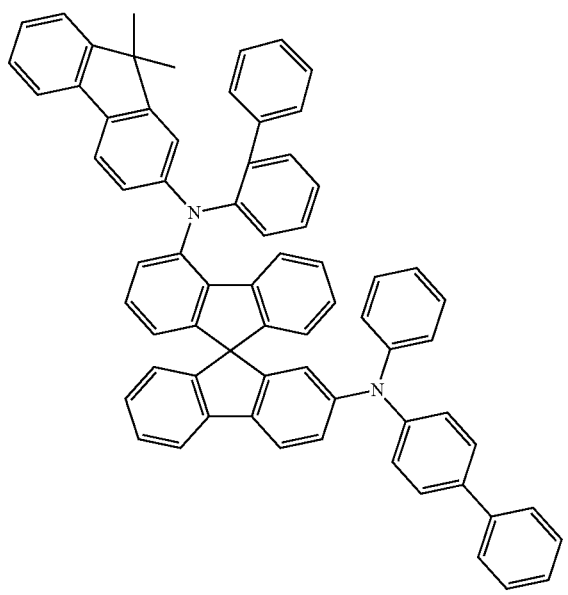
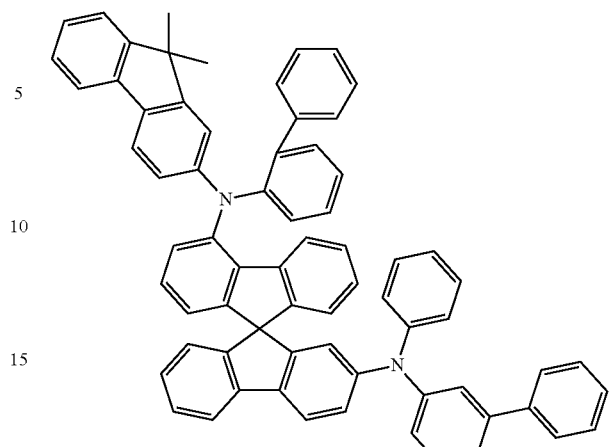
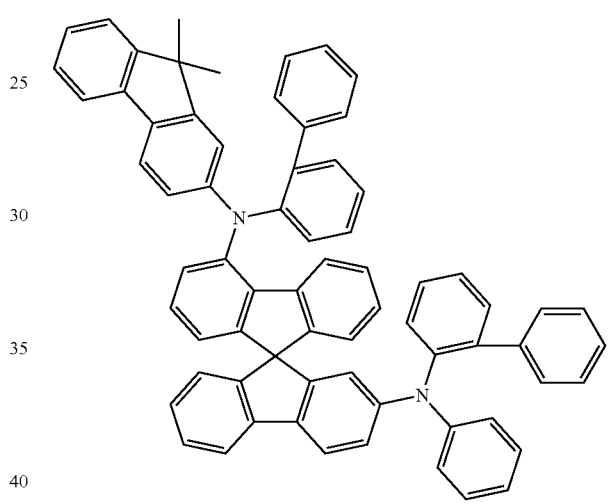
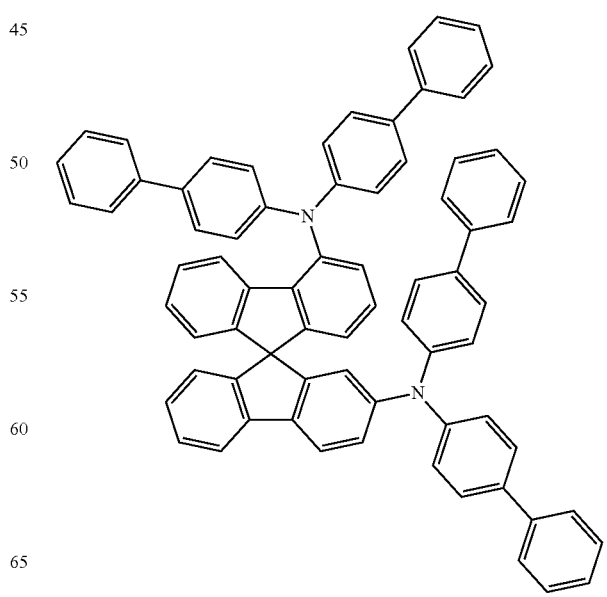

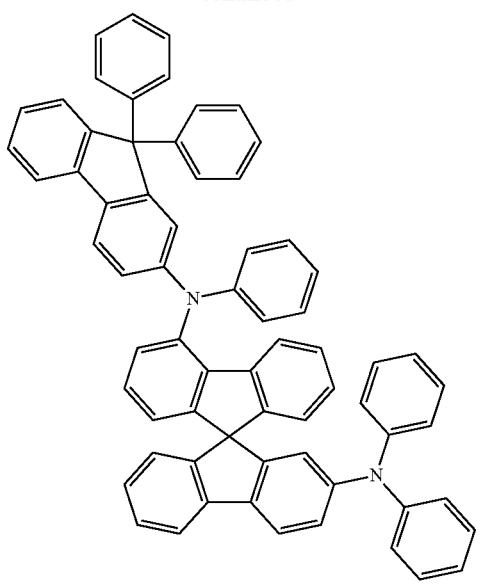
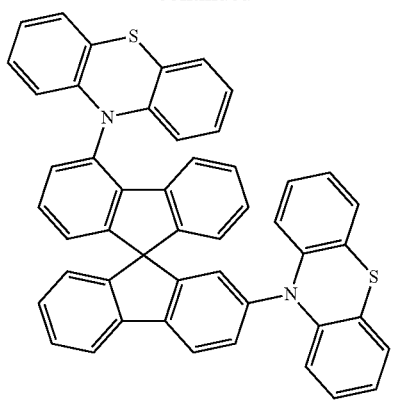
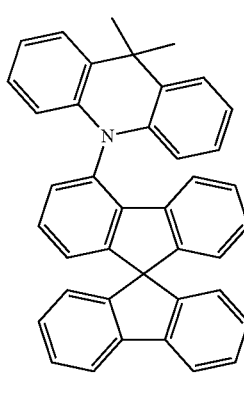
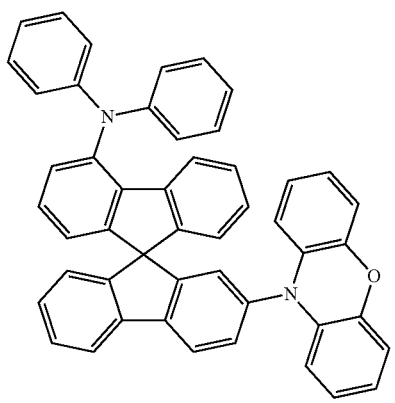
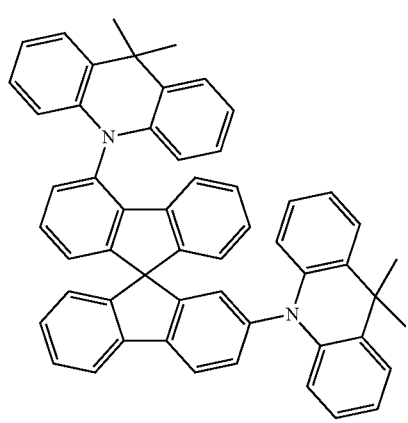
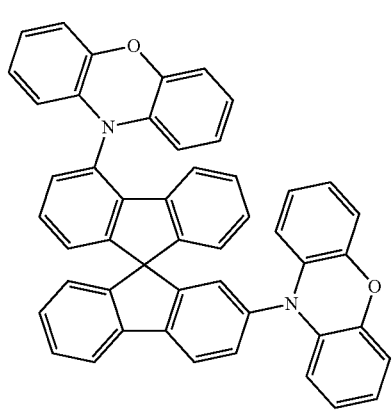
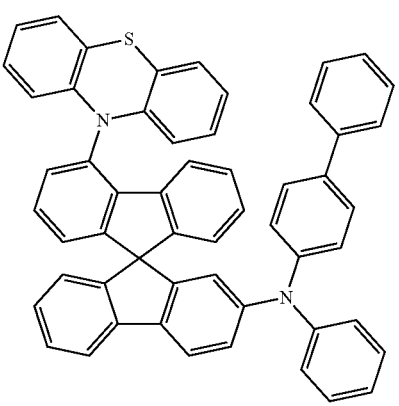

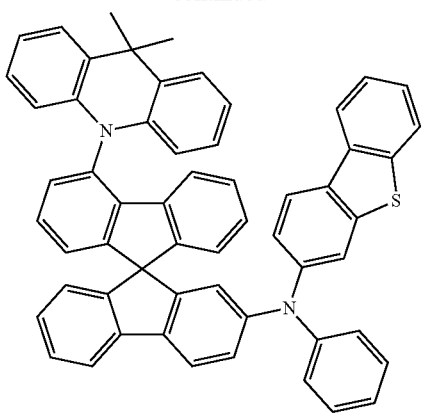
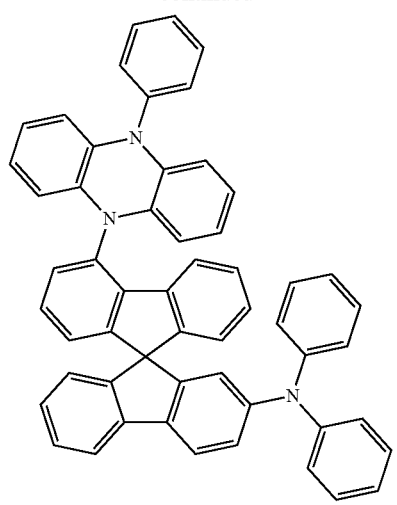
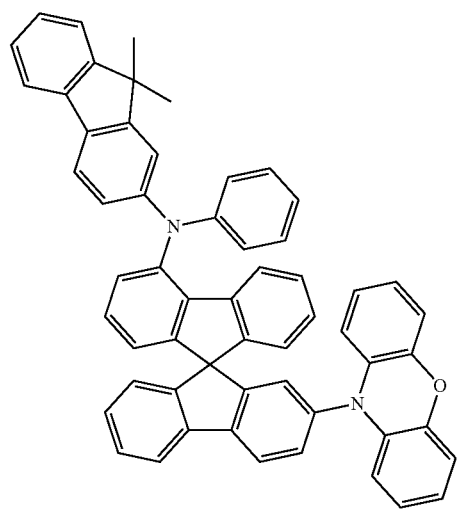
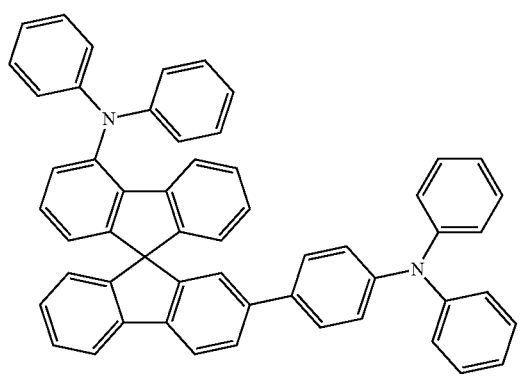
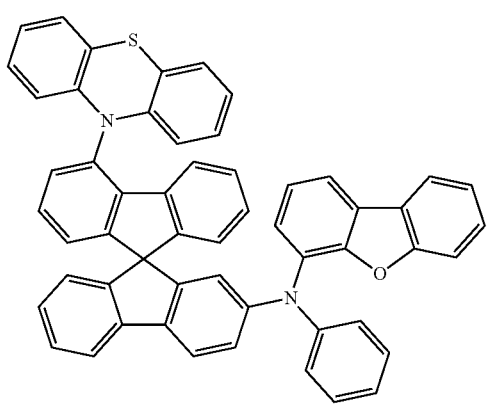
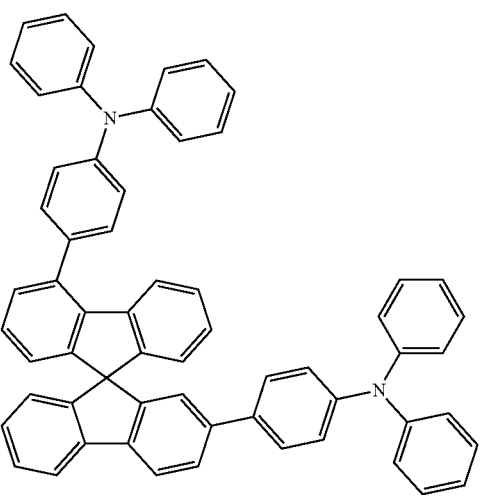

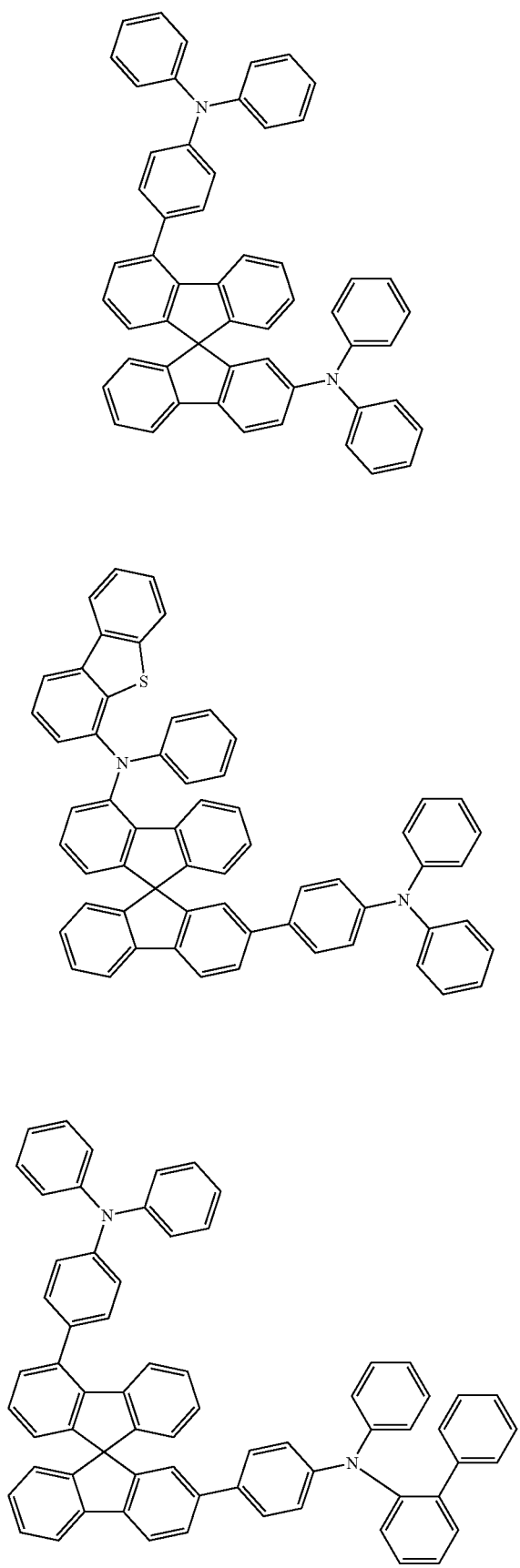

-continued

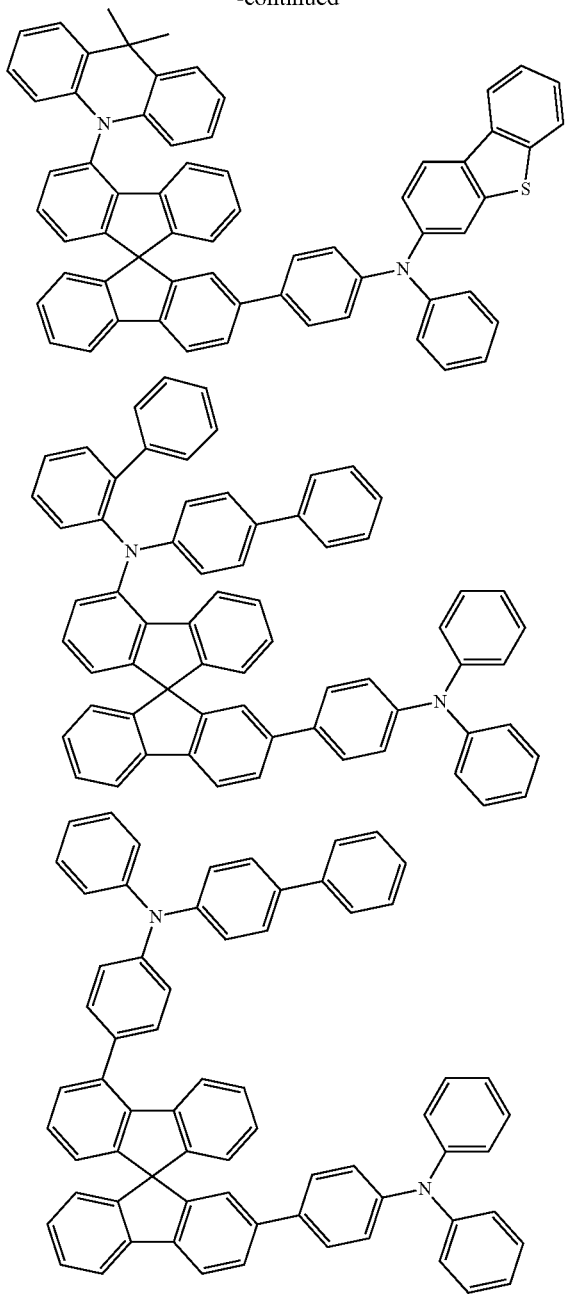

Further, the present specification provides an organic light emitting device including the compound represented by Chemical Formula 1.

An exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transport layer, a light emitting layer, an electron transport layer, an electron injection layer, and the like as organic material layers. However, the structure of the organic light emitting device is not limited thereto, and may include a fewer number of organic layers.

In an exemplary embodiment of the present specification, the organic material layer includes a hole transport layer, and the hole transport layer includes the compound of Chemical Formula 1.

In an exemplary embodiment of the present specification, the organic material layer includes a hole injection layer, and the hole injection layer includes the compound of Chemical Formula 1.

In an exemplary embodiment of the present specification, the organic material layer includes a hole injection layer, and the hole injection layer includes the compound of Chemical Formula 1, and further includes a doping material.

In an exemplary embodiment of the present specification, the organic material layer includes a hole injection layer, and the hole injection layer includes the compound of Chemical Formula 1, and includes a doping material to be doped at a doping concentration of 1 wt % to 20 wt %.

In an exemplary embodiment of the present specification, the hole injection layer may include a compound having the following structural formula.

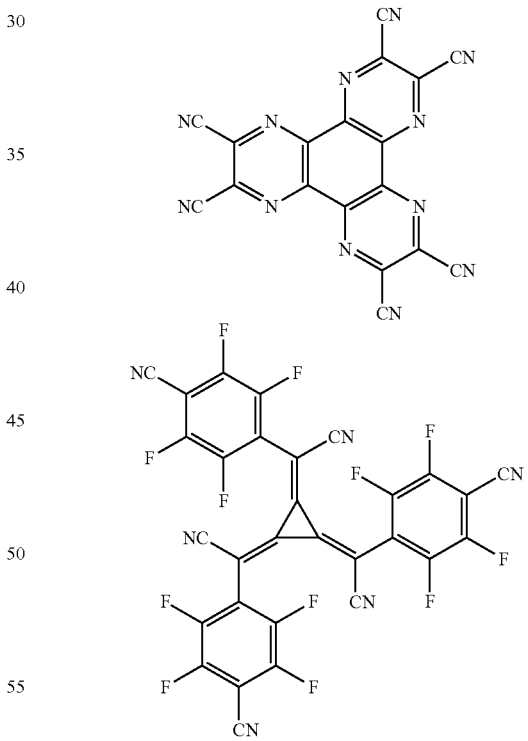

In an exemplary embodiment of the present specification, a hole injection layer is formed by using only the compound having the above structural formula, or a mixture of the compound of the present invention and the compound having the above structural formula.

In an exemplary embodiment of the present specification, the organic material layer includes a hole injection layer, a hole transport layer, or a layer which injects and transports holes simultaneously, and the hole injection layer, the hole transport layer, or the layer which injects and transports holes simultaneously includes the compound of Chemical Formula 1.

In another exemplary embodiment, the organic material layer includes a light emitting layer, and the light emitting layer includes the compound of Chemical Formula 1. According to an example, the compound of Chemical Formula 1 is a light emitting dopant, and may be included along with a light emitting host in a light emitting layer.

In an exemplary embodiment of the present specification, the organic material layer includes an electron transport layer or an electron injection layer, and the electron transport layer or the electron injection layer includes the compound of Chemical Formula 1.

In an exemplary embodiment of the present specification, the organic material layer includes a hole adjusting layer, and the hole adjusting layer includes the compound of Chemical Formula 1.

In an exemplary embodiment of the present specification, the electron transport layer, the electron injection layer, or the layer which transports and injects electrons simultaneously includes the compound of Chemical Formula 1.

In another exemplary embodiment, the organic material layer includes a light emitting layer and an electron transport layer, and the electron transport layer includes the compound of Chemical Formula 1.

According to an exemplary embodiment of the present specification, the organic material layer includes a light emitting layer, and the light emitting layer includes a compound represented by the following Chemical Formula A-1.

[Chemical Formula A-1]

in Chemical Formula A-1, w is an integer of 1 or more,

Ar5 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L3 is a direct bond; a substituted or unsubstituted arylene group; or a substituted or unsubstituted heteroarylene group, Ar6 and Ar7 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when w is 2 or more, two or more structures in the parenthesis are the same as or different from each other.

According to an exemplary embodiment of the present specification, the organic material layer includes a light emitting layer, and the light emitting layer includes the compound represented by Chemical Formula A-1 as a dopant of the light emitting layer.

According to an exemplary embodiment of the present specification, L3 is a direct bond.

According to an exemplary embodiment of the present specification, w is 2.

In an exemplary embodiment of the present specification, Ar5 is a divalent pyrene group which is unsubstituted or substituted with deuterium, an alkyl group, a cycloalkyl group or an aryl group.

In an exemplary embodiment of the present specification, Ar5 is a divalent pyrene group which is unsubstituted or substituted with deuterium, a methyl group, an ethyl group, or a tert-butyl group.

In an exemplary embodiment of the present specification, Ar5 is a divalent pyrene group.

According to an exemplary embodiment of the present specification, Ar6 and Ar7 are the same as or different from each other, and are each independently a substituted or unsubstituted aryl group having 6 to 30 carbon atoms; or a substituted or unsubstituted heteroaryl group having 2 to 30 carbon atoms.

According to an exemplary embodiment of the present specification, Ar6 and Ar7 are the same as or different from each other, and are each independently an aryl group which is unsubstituted or substituted with an alkyl group; or a heteroaryl group which is unsubstituted or substituted with an alkyl group.

According to an exemplary embodiment of the present specification, Ar6 and Ar7 are the same as or different from each other, and are each independently a phenyl group which is unsubstituted or substituted with a methyl group or a tert-butyl group; a dibenzofuran group which is unsubstituted or substituted with a methyl group or a tert-butyl group; or a dibenzothiophene group which is unsubstituted or substituted with a methyl group or a tert-butyl group.

According to an exemplary embodiment of the present specification, Ar6 and Ar7 are the same as or different from each other, and are each independently a phenyl group which is unsubstituted or substituted with a methyl group; or a dibenzofuran group which is unsubstituted or substituted with a tert-butyl group.

According to an exemplary embodiment of the present specification, Ar6 and Ar7 are the same as or different from each other, and are each independently a phenyl group which is substituted with a methyl group; or a dibenzofuran group which is substituted with a tert-butyl group.

According to an exemplary embodiment of the present specification, Chemical Formula A-1 is represented by the following compounds.

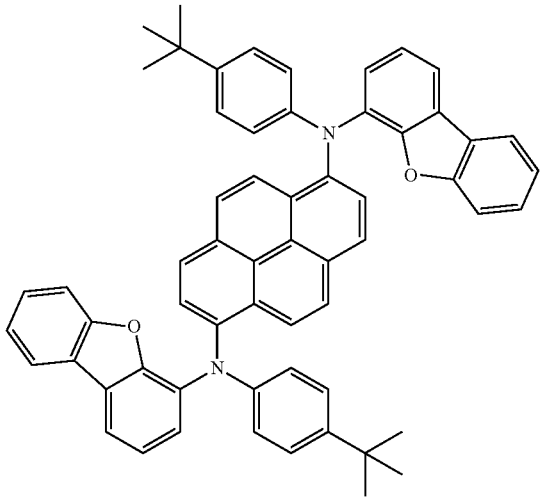

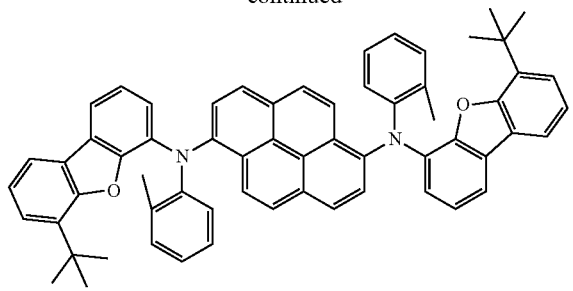

According to an exemplary embodiment of the present specification, the organic material layer includes a light emitting layer, and the light emitting layer includes a compound represented by the following Chemical Formula A-2.

[Chemical Formula A-2]

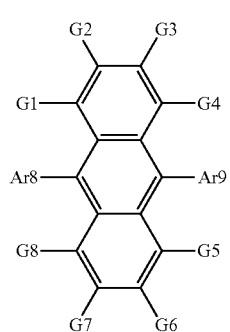

In Chemical Formula A-2,

Ar8 and Ar9 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula A-2 as a host of the light emitting layer.

According to an exemplary embodiment of the present specification, Ar8 and Ar9 are the same as or different from each other, and are each independently a substituted or unsubstituted polycyclic aryl group.

According to an exemplary embodiment of the present specification, Ar8 and Ar9 are the same as or different from each other, and are each independently a substituted or unsubstituted polycyclic aryl group having 10 to 30 carbon atoms.

According to an exemplary embodiment of the present specification, Ar8 and Ar9 are the same as or different from each other, and are each independently a substituted or unsubstituted naphthyl group.

According to an exemplary embodiment of the present specification, Ar8 and Ar9 are the same as or different from each other, and are each independently a substituted or unsubstituted 1-naphthyl group or 2-naphthyl group.

According to an exemplary embodiment of the present specification, Ar8 is a 1-naphthyl group, and Ar9 is a 2-naphthyl group.

According to an exemplary embodiment of the present specification, G1 to G8 are hydrogen.

According to an exemplary embodiment of the present specification, Chemical Formula A-2 is represented by the following compound.

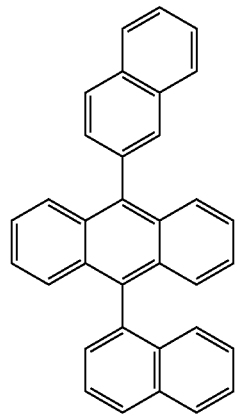 [SMILES: c1ccc2cc(-c3c4ccccc4c(-c4cccc5ccccc45)c4ccccc34)ccc2c1]

According to an exemplary embodiment of the present specification, the organic material layer includes a light emitting layer, and the light emitting layer includes the compound represented by Chemical Formula A-1 as a dopant of the light emitting layer, and includes the compound represented by Chemical Formula A-2 as a host of the light emitting layer.

An exemplary embodiment of the present specification provides an organic light emitting device including: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the compound of Chemical Formula 1. In one exemplary embodiment, as the two or more organic material layers, two or more may be selected from the group consisting of an electron transport layer, an electron injection layer, a layer which transports and injects electrons simultaneously, and a hole blocking layer. In an exemplary embodiment of the present specification, the organic material layer includes two or more electron transport layers, and at least one of the two or more electron transport layers includes the compound of Chemical Formula 1. Specifically, in an exemplary embodiment of the present specification, the compound of Chemical Formula 1 may also be included in one layer of the two or more electron transport layers, and may be included in each of the two or more electron transport layers.

Further, in an exemplary embodiment of the present specification, when the compound of Chemical Formula 1 is included in each of the two or more electron transport layers, the other materials except for the compound of Chemical Formula 1 may be the same as or different from each other.

In another exemplary embodiment, the organic light emitting device may be an organic light emitting device having a structure (normal type) in which a positive electrode, one or more organic material layers, and a negative electrode are sequentially stacked on a substrate.

In still another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present specification is exemplified in FIGS. 1 and 2.

FIG. 1 illustrates an example of an organic light emitting device composed of a substrate 1, a positive electrode 2, a light emitting layer 3, and a negative electrode 4. In the structure as described above, the compound may be included in the light emitting layer.

FIG. 2 illustrates an example of an organic light emitting device composed of a substrate 1, a positive electrode 2, a hole injection layer 5, a hole transport layer 6, a light emitting layer 7, an electron transport layer 8, and a negative electrode 4. In the structure as described above, the compound may be included in one or more of the hole injection layer, the hole transport layer, the light emitting layer, and the electron transport layer.

The organic light emitting device of the present specification may be manufactured by the materials and methods known in the art, except that one or more layers of the organic material layers include the compound of the present specification, that is, the compound of Chemical Formula 1.

When the organic light emitting device includes a plurality of organic material layers, the organic material layers may be formed of the same material or different materials.

The organic light emitting device of the present specification may be manufactured by the materials and methods known in the art, except that one or more layers of the organic material layers include the compound of Chemical Formula 1, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamine group, and examples thereof include a pyrene, an anthracene, a chrysene, a periflanthene, and the like, which have an arylamine group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamine group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material is a material which may receive electrons well from a negative electrode and transfer the electrons to a light emitting layer, and is suitably a material having a large mobility for electrons. Specific examples thereof include: an Al complex of 8-hydroxyquinoline; a complex including Alq$_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Chemical Formula 1 may be included in an organic solar cell or an organic transistor in addition to an organic light emitting device.

MODE FOR INVENTION

The preparation of the compound represented by Chemical Formula 1 and the organic light emitting device including the same will be specifically described in the following Examples. However, the following Examples are provided for exemplifying the present specification, and the scope of the present specification is not limited thereby.

PREPARATION EXAMPLES

<Preparation Example 1> Synthesis of A1 to A3

Synthesis of A1 and A3

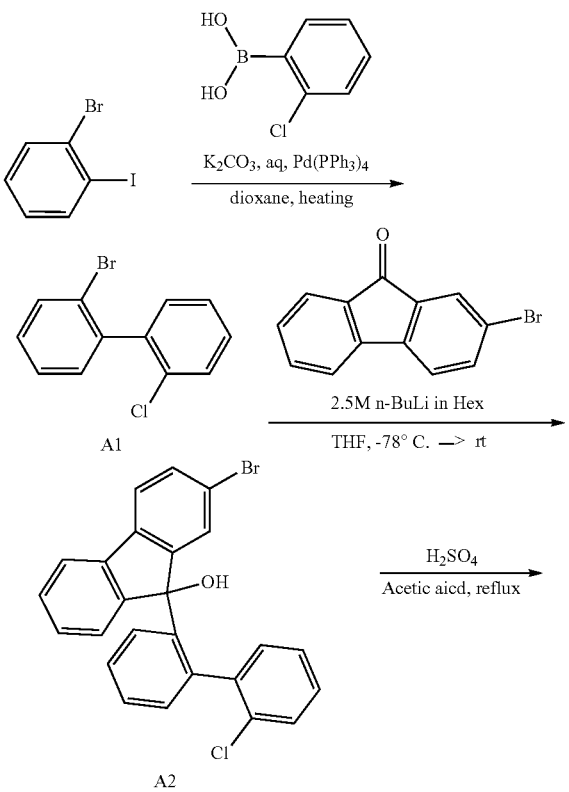

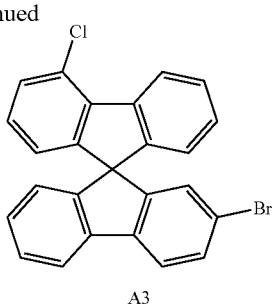

A3

1. Synthesis of A1

After 1-bromo-2-iodobenzene (30 g, 106 mmol) and (2-chlorophenyl)boronic acid (16.9 g, 108.6 mmol) were added to dioxane (300 ml), a 2M aqueous potassium carbonate solution (100 ml) was added thereto, tetrakistriphenyl-phosphinopalladium (2.45 g, 2 mol %) was put thereinto, and then the resulting mixture was heated and stirred for 4 hours. The temperature was lowered to normal temperature, the reaction was terminated, and then the potassium carbonate solution was removed to separate the layers. After the solvent was removed, the residue was columned with hexane to prepare Compound A-1, which is a white solid (25.3 g, 90%).

MS[M+H]$^+$=266.95

2. Synthesis of A2

After Compound A-1 (20 g, 75.2 mmol) was dissolved in THF (250 ml), the temperature was lowered to −78° C., and then 2.5 M n-BuLi (39 ml) was added dropwise thereto, and after 30 minutes, 2-bromo-9H-fluoren-9-one (19.3 g, 75.2 mmol) was put thereinto, the temperature was increased to normal temperature, and then the resulting mixture was stirred for 1 hour. After 1 N HCl (300 ml) was put thereinto and the resulting mixture was stirred for 30 minutes, the layers were separated to remove the solvent, and then the residue was washed with ethyl acetate to prepare Compound A2 (28.5 g, 85%).

MS[M+H]$^+$=447.01

3. Synthesis of A3

After Compound A2 (20 g, 44.84 mmol) was put into acetic acid (250 ml), 2 ml of sulfuric acid was added dropwise thereto, and the resulting mixture was stirred and refluxed. The temperature was lowered to normal temperature, the resulting product was neutralized with water, and then the filtered solid was recrystallized with ethyl acetate to prepare Compound A3 (13.43 g, 70%).

MS[M+H]$^+$=429.00

<Preparation Example 2> Synthesis of Compounds 1 to 5

Synthesis of Compound 1

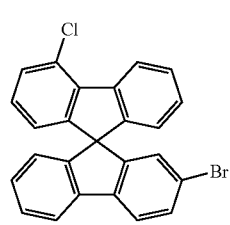 + 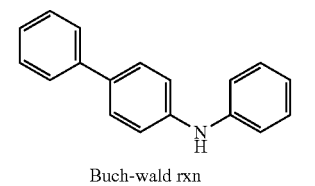 →Buch-wald rxn→

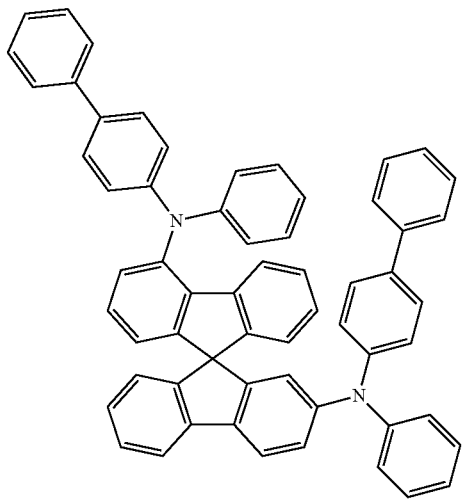

1

A3 (15 g, 35.05 mmol), N-phenyl-[1,1'-biphenyl]-4-amine (17.35 g, 70.8 mmol), and sodium-t-butoxide (9.43 g, 98.14 mmol) were put into xylene and heated and stirred and then the resulting mixture was refluxed, and [bis(tri-t-butylphosphine)]palladium (358 mg, 2 mmol %) was put thereinto. The temperature was lowered to normal temperature, the reaction was terminated, and then the resulting product was recrystallized by using tetrahydrofuran and ethyl acetate to prepare Compound 1.

MS[M+H]$^+$=803.33

Synthesis of Compound 2

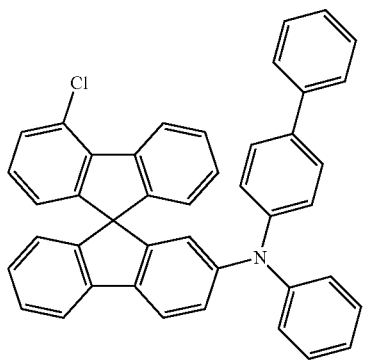

B1

-continued

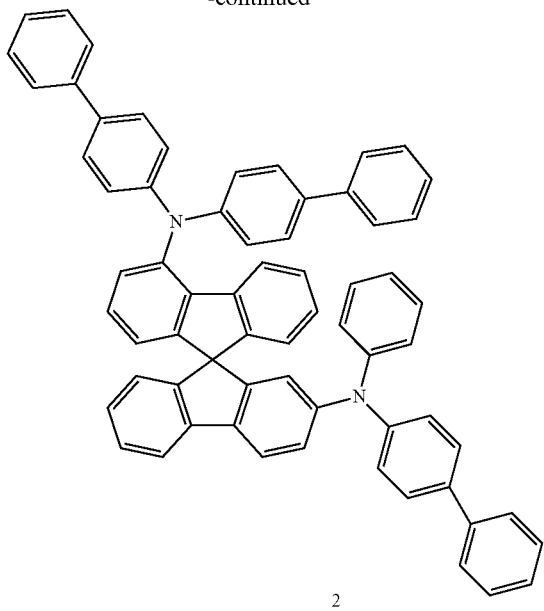

2

A3 (15 g, 35.05 mmol), N-phenyl-[1,1'-biphenyl]-4-amine (8.7 g, 35.4 mmol), and sodium-t-butoxide (4.72 g, 49.07 mmol) were put into toluene and heated and stirred and then the resulting mixture was refluxed, and [bis(tri-t-butylphosphine)]palladium (179 mg, 2 mmol %) was put thereinto. The temperature was lowered to normal temperature, the reaction was terminated, and then recrystallization was performed by using tetrahydrofuran and ethyl acetate to prepare B1, B1 was dried, then B1 (15 g, 25.28 mmol), di([1,1'-biphenyl]-4-yl)amine (8.2 g, 25.54 mmol), and sodium-t-butoxide (3.4 g, 35.4 mmol) were put into toluene and heated and stirred and then the resulting mixture was refluxed, and [bis(tri-t-butylphosphine)]palladium (257 mg, 2 mmol %) was put thereinto. The temperature was lowered to normal temperature, the reaction was terminated, and then the resulting product was recrystallized by using tetrahydrofuran and ethyl acetate to prepare Compound 2.

MS[M+H]$^+$=879.37

Synthesis of Compound 3

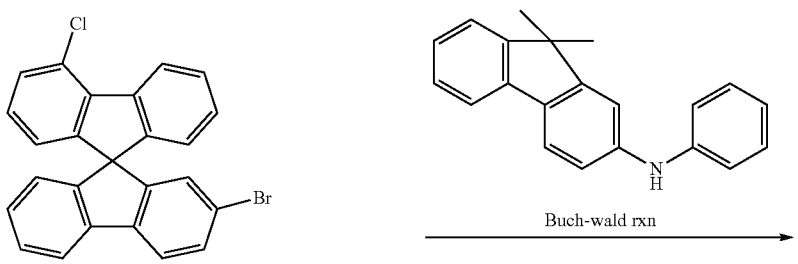

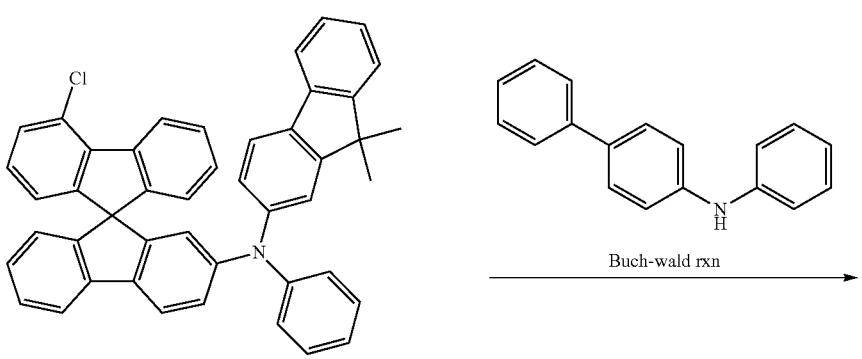

B2

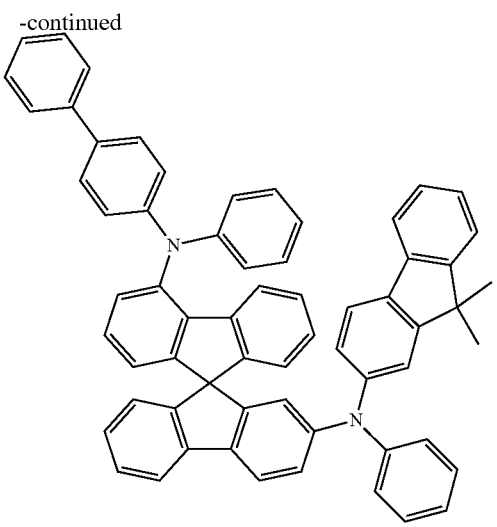
3
B2 was prepared by performing the synthesis in the same manner as in the synthesis of Compound 2, except that 9,9'-dimethyl-N-phenyl-9H-fluoren-2-amine was used instead of N-phenyl-[1,1'-biphenyl]-4-amine, and then Compound 3 was prepared by using N-phenyl-[1,1'-biphenyl]-4-amine instead of di([1,1'-biphenyl]-4-yl)amine.
MS[M+H]⁺=843.37
Synthesis of Compound 4
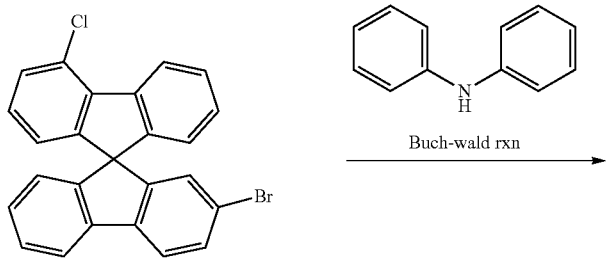
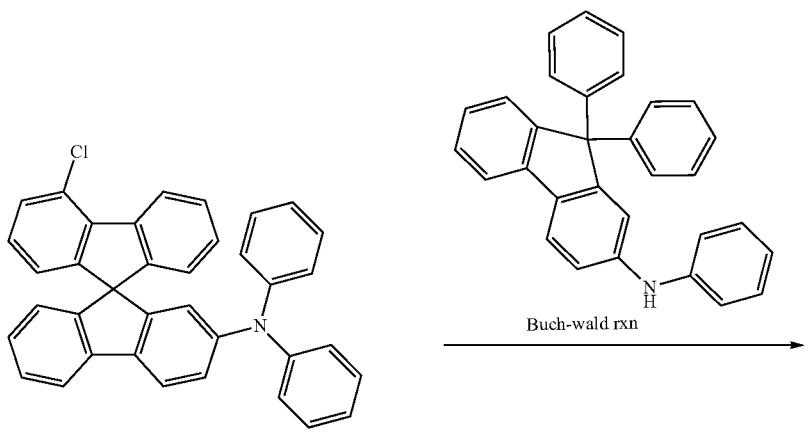
B3

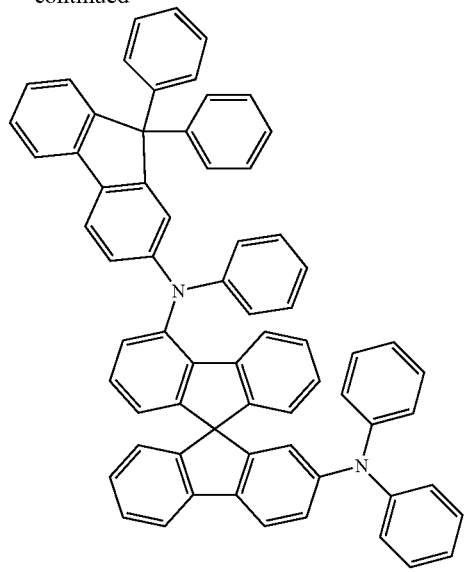

4

B3 was prepared by performing the synthesis in the same manner as in the synthesis of Compound 2, except that diphenylamine was used instead of N-phenyl-[1,1'-biphenyl]-4-amine, and then Compound 4 was prepared by using N, 9, 9-triphenyl-9H-fluoren-2-amine instead of di([1,1'-biphenyl]-4-yl)amine.

MS[M+H]$^+$=891.37

Synthesis of Compound 5

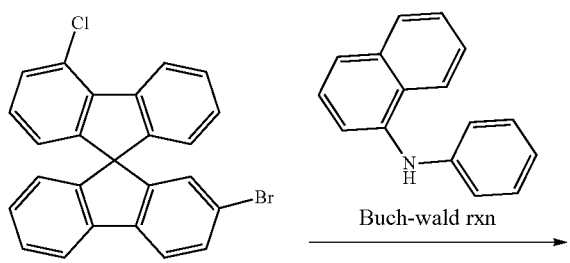

Buch-wald rxn

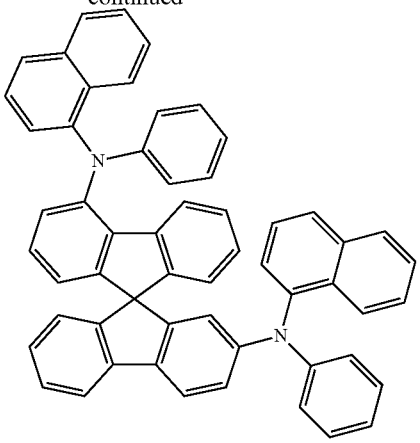

5

Compound 5 was prepared by performing the synthesis in the same manner as in the synthesis of Compound 1, except that N-phenylnaphthalen-1-amine was used instead of N-phenyl-[1,1'-biphenyl]-4-amine.
MS[M+H]$^+$=751.30
Synthesis of Compound 6

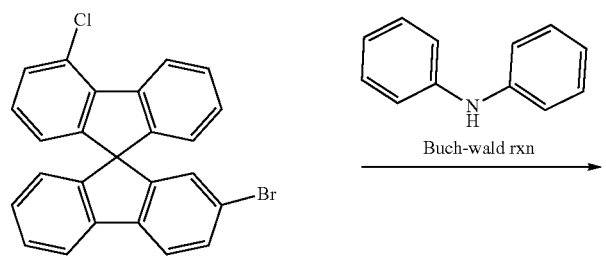

Buch-wald rxn

-continued

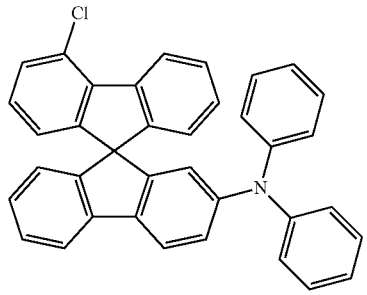

B3

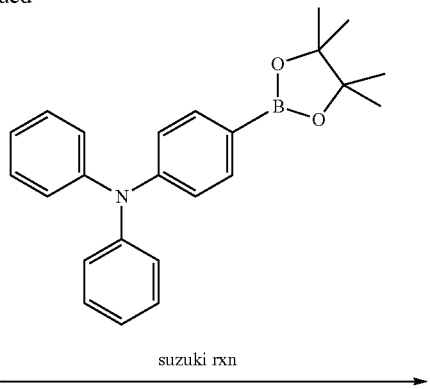

suzuki rxn →

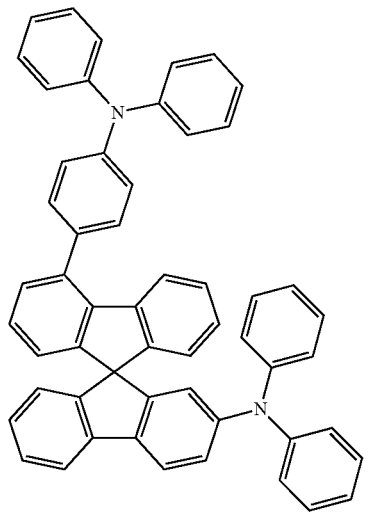

6

A3 (15 g, 34.9 mmol), diphenylamine (6.08 g, 35.9 mmol), and sodium-t-butoxide (4.7 g, 48.9 mmol) were put into toluene and heated and stirred and then the resulting mixture was refluxed, and [bis(tri-t-butylphosphine)]palladium (357 mg, 2 mmol %) was put thereinto. The temperature was lowered to normal temperature, the reaction was terminated, and then recrystallization was performed by using tetrahydrofuran and ethyl acetate to prepare B3, B3 was dried, then B3 (15 g, 28.95 mmol) and N,N-diphenyl-4-(4,4,5,5-tetramethyl-1,3,2-dioxaboran-2-yl)aniline (11.29 g, 30.40 mmol) were put into dioxane (300 ml), a 2M aqueous potassium carbonate solution (100 ml) was added thereto, tetrakistriphenyl-phosphinopalladium (669 mg, 57.9 mmol) was put thereinto, and then the resulting mixture was heated and stirred for 3 hours. The temperature was lowered to normal temperature, the reaction was terminated, and then the potassium carbonate solution was removed to separate the layers. After the solvent was removed, a white solid was recrystallized by using tetrahydrofuran and ethyl acetate to prepare Compound 6 (15 g, yield 68.4%).

MS[M+H]$^+$=727.92

Synthesis of Compound 7

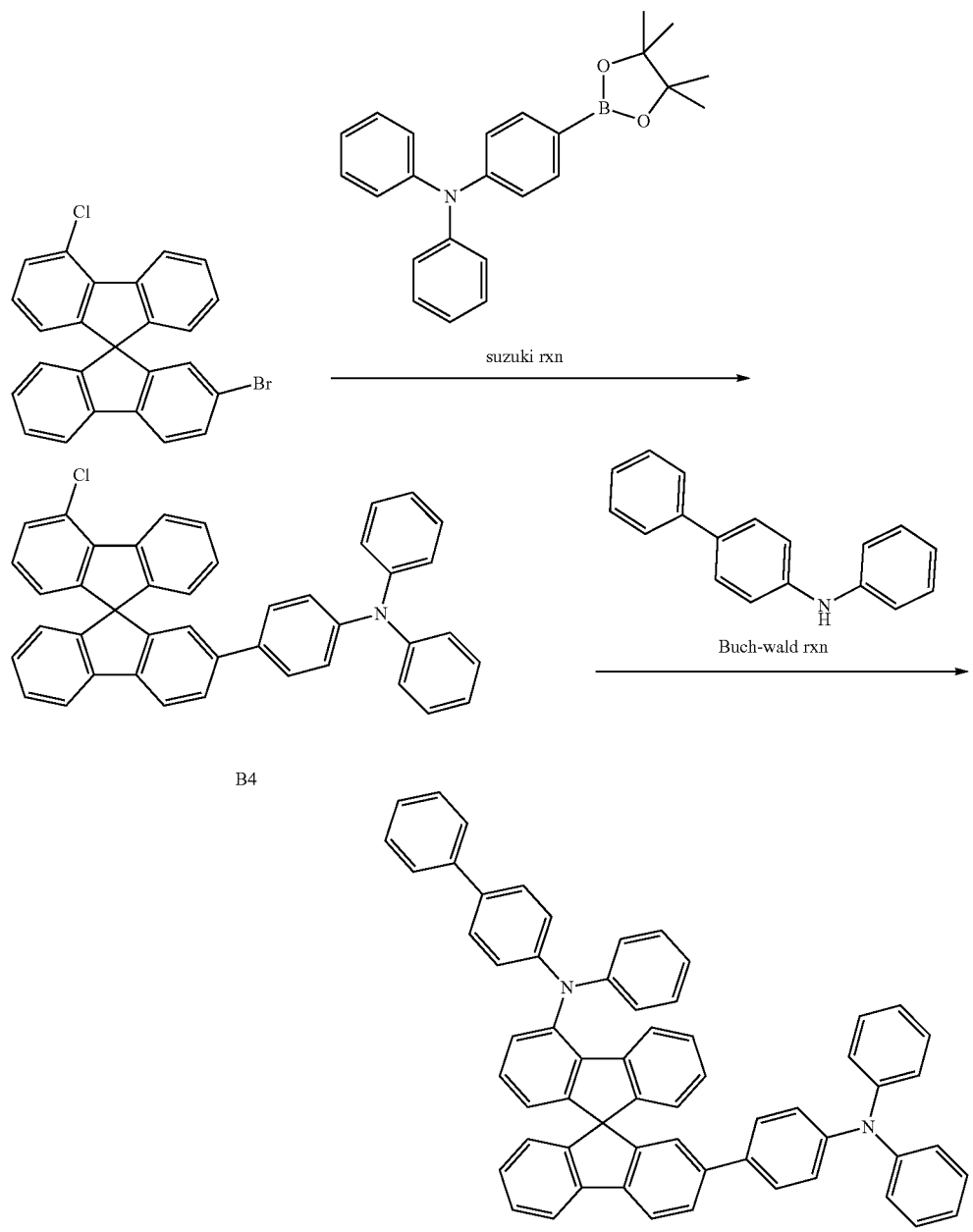

A3 (15 g, 28.95 mmol) and N,N-diphenyl-4-(4,4,5,5-tetramethyl-1,3,2-dioxaboran-2-yl)aniline (11.29 g, 30.40 mmol) were put into dioxane (300 ml), a 2M aqueous potassium carbonate solution (100 ml) was added thereto, tetrakistriphenyl-phosphinopalladium (669 mg, 57.9 mmol) was put thereinto, and then the resulting mixture was heated and stirred for 3 hours. The temperature was lowered to normal temperature, the reaction was terminated, and then the potassium carbonate solution was removed to separate the layers. After the solvent was removed, a white solid was recrystallized by using tetrahydrofuran and ethyl acetate to prepare B4, B4 was dried, and then B4 (15 g, 35.05 mmol), N-phenyl-[1,1'-biphenyl]-4-amine (8.7 g, 35.4 mmol), and sodium-t-butoxide (4.72 g, 49.07 mmol) were put into toluene and heated and stirred, and then the resulting mixture was refluxed, and [bis(tri-t-butylphosphine)]palladium (179 mg, 2 mmol %) was put thereinto. The temperature was lowered to normal temperature, the reaction was terminated, and then the resulting product was recrystallized by using tetrahydrofuran and ethyl acetate to prepare Compound 7.

MS[M+H]$^+$=804.02

Example 1

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co. was used as a detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

A1 (hexanitrile hexaazatriphenylene) was thermally vacuum deposited to have a thickness of 500 Å on a transparent ITO electrode thus prepared, thereby forming a hole injection layer. Compound 3 (1,100 Å) synthesized in Preparation Example 2, which is a material for transporting holes, was vacuum deposited thereon, and then HT2 was sequentially vacuum deposited to have a film thickness of 600 Å on the hole transport layer, thereby forming a hole adjusting layer. As a light emitting layer, a compound (2%) of host H1 and dopant D1 was vacuum deposited to have a thickness of 300 Å. And then, E1 compound was formed as an electron transport layer along with LiQ at a ratio of 1:1 (350 Å), and then lithium fluoride (LiF) and aluminum were sequentially deposited to have a thickness of 10 Å and 1,000 Å, respectively, to form a negative electrode, thereby manufacturing an organic light emitting device.

In the aforementioned procedure, the deposition rates of the organic material, lithium fluoride, and aluminum were maintained at 1 Å/sec, 0.2 Å/sec, and 3 to 7 Å/sec, respectively.

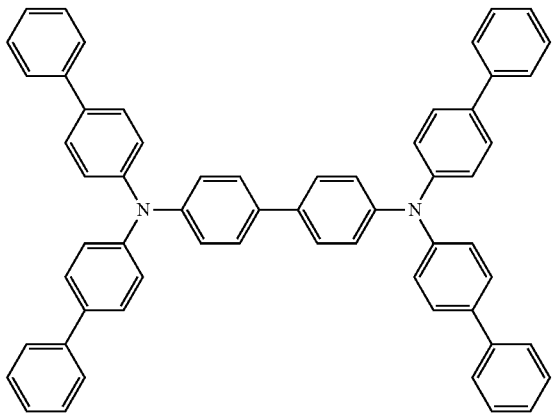

[HT1]

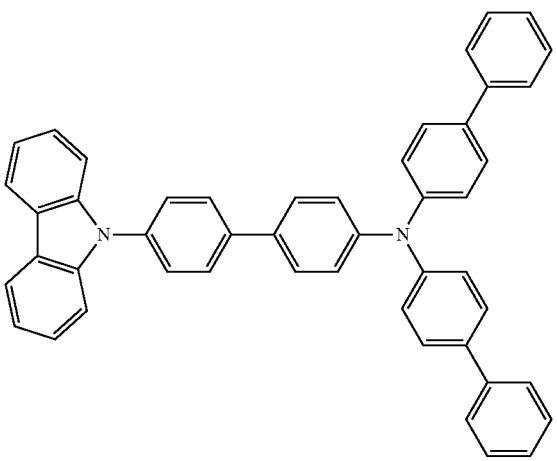

[HT2]

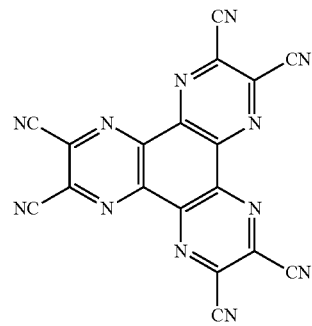

[A1]

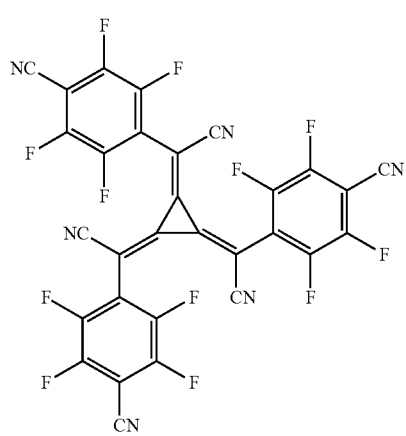

[A2]

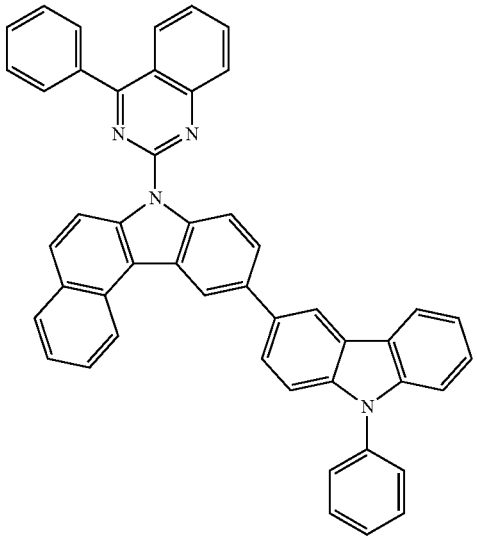

[H1]

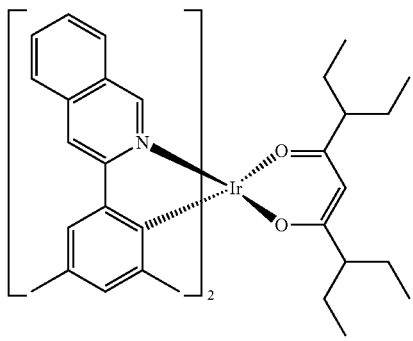

[D1]

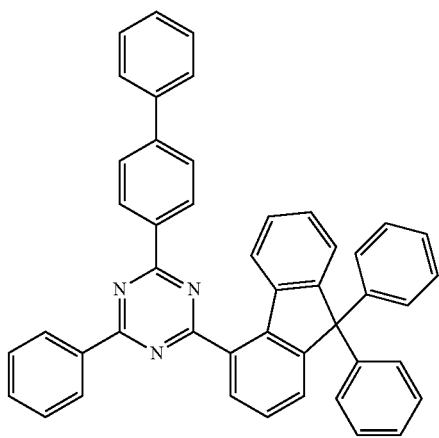

[E1]

Example 2

An organic light emitting device was manufactured in the same manner as in Example 1, except that as the hole transport layer, Compound 4 was used instead of Compound 3 synthesized in Preparation Example 2.

Example 3

An organic light emitting device was manufactured in the same manner as in Example 1, except that as the hole transport layer, Compound 5 was used instead of Compound 3 synthesized in Preparation Example 2.

Example 4

An organic light emitting device was manufactured in the same manner as in Example 1, except that as the hole transport layer, HT1 was used instead of Compound 3 synthesized in Preparation Example 2, and as the hole adjusting layer, Compound 1 was used instead of HT2.

Example 5

An organic light emitting device was manufactured in the same manner as in Example 4, except that as the hole adjusting layer, Compound 2 was used instead of Compound 1 synthesized in Preparation Example 2.

Example 6

Compound 3 was thermally vacuum deposited to have a thickness of 50 Å on a transparent ITO electrode as prepared in Example 1, thereby forming a hole injection layer (100 Å), A2 was doped at a doping concentration of 5%, the aforementioned Compound 3 (1,100 Å), which is a material for transporting holes, was vacuum deposited thereon, and then HT2 was sequentially vacuum deposited to have a film thickness (600 Å) on the hole transport layer, thereby forming a hole adjusting layer. As a light emitting layer, a compound (2%) of host H1 and dopant D1 was vacuum deposited to have a thickness of 300 Å. And then, E1 compound was formed as an electron transport layer along with LiQ at a ratio of 1:1 (350 Å), and then lithium fluoride (LiF) and aluminum were sequentially deposited to have a thickness of 10 Å and 1,000 Å, respectively, to form a negative electrode, thereby manufacturing an organic light emitting device.

Example 7

An organic light emitting device was manufactured in the same manner as in Example 6, except that as the hole injection layer and the hole transport layer, Compound 5 was used instead of Compound 3 synthesized in Preparation Example 2.

Example 8

An organic light emitting device was manufactured in the same manner as in Example 6, except that as the hole injection layer and the hole transport layer, HT1 was used instead of Compound 3, and as the hole adjusting layer, Compound 1 was used instead of HT2.

Example 9

An organic light emitting device was manufactured in the same manner as in Example 8, except that as the hole adjusting layer, Compound 2 was used instead of Compound 1 synthesized in Preparation Example 2.

Example 10

An organic light emitting device was manufactured in the same manner as in Example 1, except that as the hole transport layer, Compound 6 was used instead of Compound 3 synthesized in Preparation Example 2.

Example 11

An organic light emitting device was manufactured in the same manner as in Example 8, except that as the hole adjusting layer, Compound 7 was used instead of Compound 1 synthesized in Preparation Example 2.

Comparative Example 1

An experiment was performed in the same manner as in Example 1, except that as the hole transport layer, HT1 was used instead of Compound 3 synthesized in Preparation Example 2.

Comparative Example 2

An experiment was performed in the same manner as in Example 6, except that as the hole injection layer and the hole transport layer, HT1 was used instead of Compound 3.

TABLE 1

| Experimental Example (10 mA/cm²) | Hole injection layer | Hole transport layer | Hole adjusting layer | Voltage (V) | Efficiency (cd/A) | CIE_x | CIE-y |
|---|---|---|---|---|---|---|---|
| Example 1 | A1 | Compound 3 | HT2 | 4.01 | 25.95 | 0.658 | 0.340 |
| Example 2 | A1 | Compound 4 | HT2 | 4.04 | 25.53 | 0.658 | 0.340 |
| Example 3 | A1 | Compound 5 | HT2 | 3.99 | 25.99 | 0.658 | 0.340 |
| Example 4 | A1 | HT1 | Compound 1 | 3.84 | 26.32 | 0.658 | 0.341 |
| Example 5 | A1 | HT1 | Compound 2 | 3.95 | 28.66 | 0.657 | 0.340 |
| Example 6 | A2 + Compound 3 | Compound 3 | HT2 | 3.82 | 27.01 | 0.658 | 0.340 |
| Example 7 | A2 + Compound 5 | Compound 5 | HT2 | 3.93 | 28.21 | 0.658 | 0.340 |
| Example 8 | A2 + HT1 | HT1 | Compound 1 | 3.86 | 27.88 | 0.657 | 0.341 |
| Example 9 | A2 + HT1 | HT1 | Compound 2 | 3.88 | 28.12 | 0.658 | 0.340 |
| Example 10 | A1 | Compound 6 | HT2 | 4.01 | 25.95 | 0.658 | 0.340 |
| Example 11 | A2 + HT1 | HT1 | Compound 7 | 3.86 | 27.83 | 0.657 | 0.341 |
| Comparative Example 1 | A1 | HT1 | HT2 | 4.32 | 23.55 | 0.658 | 0.340 |
| Comparative Example 2 | A2 + HT1 | HT1 | HT2 | 4.21 | 23.88 | 0.658 | 0.340 |

Example 12

The above-described A1 was thermally vacuum deposited to have a thickness of 50 Å on a transparent ITO electrode prepared, thereby forming a hole injection layer. Compound 3 (800 Å), which is a material for transporting holes, was vacuum deposited thereon, thereby forming a hole transport layer, HT2 (100 Å) was formed as a hole adjusting layer thereon, and then host H2 and dopant D2 (4 wt %) were sequentially vacuum deposited to have a thickness of 300 Å. And then, E1 compound was formed as an electron transport layer along with LiQ at a ratio of 1:1 (300 Å), and then lithium fluoride (LiF) and aluminum were sequentially deposited to have a thickness of 10 Å and 800 Å, respectively, to form a negative electrode, thereby manufacturing an organic light emitting device.

In the aforementioned procedure, the deposition rates of the organic material, lithium fluoride, and aluminum were maintained at 1 Å/sec, 0.2 Å/sec, and 3 to 7 Å/sec, respectively.

[A1]

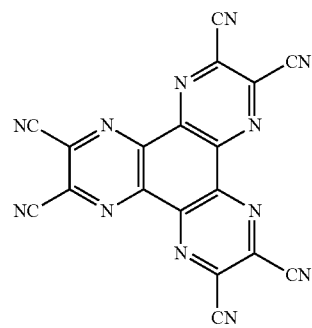

-continued

[A2]

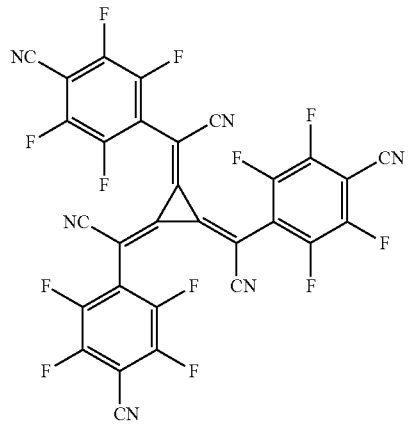

[HT1]

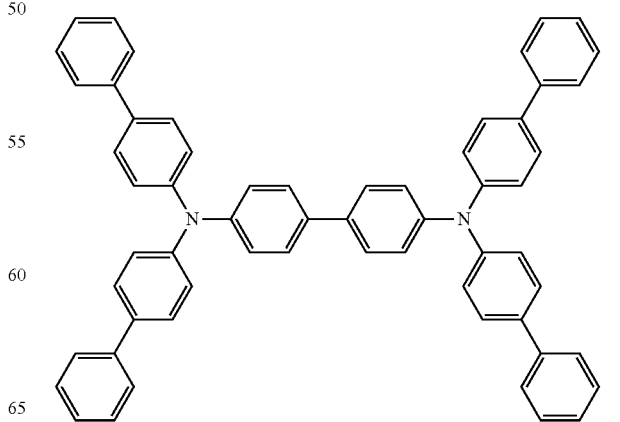

-continued

[HT2]

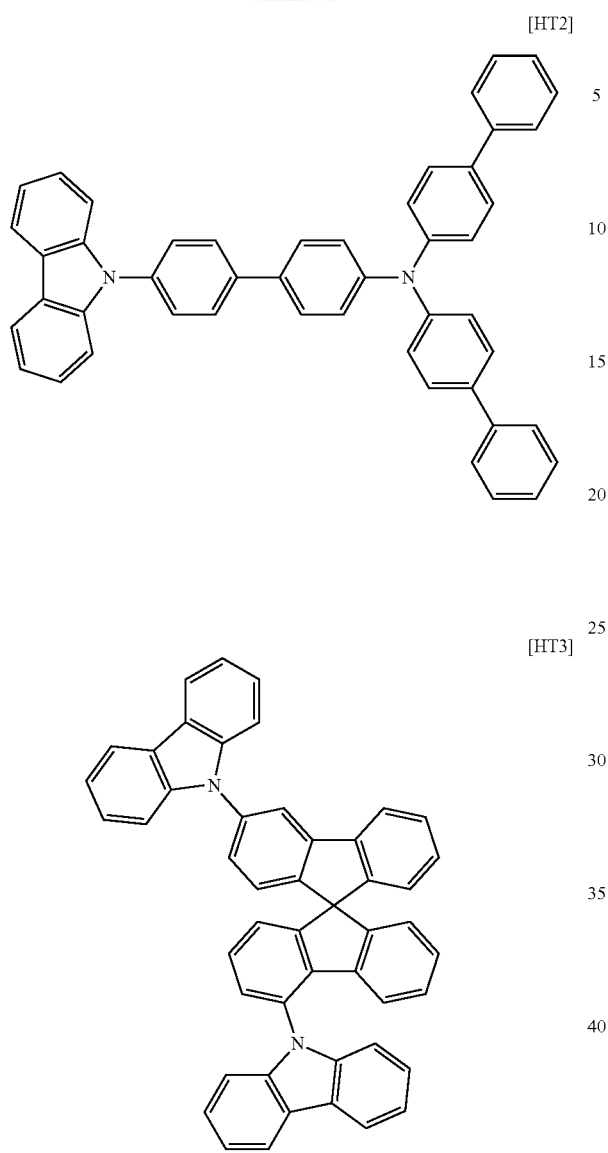

[HT3]

[HT4]

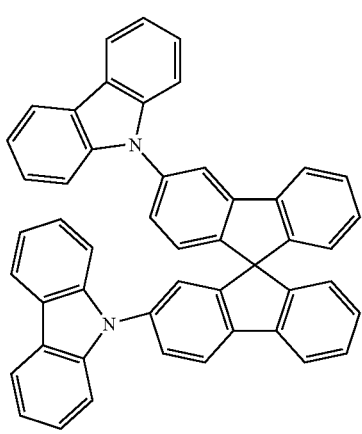

-continued

[H2]

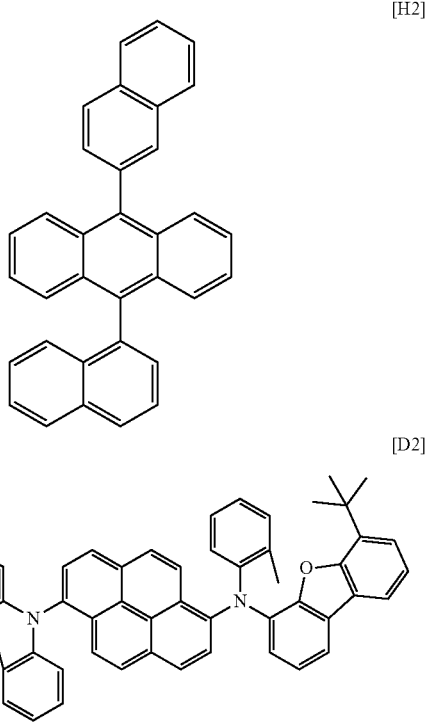

[D2]

Example 13

An experiment was performed in the same manner as in Example 12, except that as the hole transport layer, Compound 4 was used instead of Compound 3 synthesized in Preparation Example 2.

Example 14

An experiment was performed in the same manner as in Example 12, except that as the hole transport layer, Compound 5 was used instead of Compound 3 synthesized in Preparation Example 2.

Example 15

Compound 3 was thermally vacuum deposited to have a thickness of 50 Å on a transparent ITO electrode as prepared in Example 1, thereby forming a hole injection layer, Compound A1 was doped at a doping concentration of 10%, a hole transport layer was formed by vacuum depositing Compound 3 (800 Å), HT2 (100 Å) was formed as a hole adjusting layer thereon, and then host HT2 and dopant D2 (4 wt %) were sequentially vacuum deposited to have a thickness of 300 Å. And then, E1 compound was formed as an electron transport layer along with LiQ at a ratio of 1:1 (300 Å), and then lithium fluoride (LiF) and aluminum were sequentially deposited to have a thickness of 10 Å and 800 Å, respectively, to form a negative electrode, thereby manufacturing an organic light emitting device.

Example 16

An experiment was performed in the same manner as in Example 15, except that as the hole injection layer and the hole transport layer, Compound 5 was used instead of Compound 3.

Example 17

An experiment was performed in the same manner as in Example 13, except that as the hole injection layer and the hole transport layer, HT1 was used instead of Compound 3, and as the hole adjusting layer, Compound 1 was used instead of HT2.

Comparative Example 3

An experiment was performed in the same manner as in Example 12, except that as the hole transport layer, HT1 was used instead of Compound 3 synthesized in Preparation Example 2.

Comparative Example 4

An experiment was performed in the same manner as in Example 15, except that as the hole injection layer and the hole transport layer, HT1 was used instead of Compound 3.

Comparative Example 5

An experiment was performed in the same manner as in Example 12, except that as the hole transport layer, HT3 was used instead of Compound 3 synthesized in Preparation Example 2.

Comparative Example 6

An experiment was performed in the same manner as in Example 12, except that as the hole transport layer, HT4 was used instead of Compound 3 synthesized in Preparation Example 2.

Comparative Example 7

An experiment was performed in the same manner as in Example 15, except that as the hole injection layer and the hole transport layer, HT3 was used instead of Compound 3.

Comparative Example 8

An experiment was performed in the same manner as in Example 15, except that as the hole injection layer and the hole transport layer, HT4 was used instead of Compound 3.

TABLE 2

| Experimental Example ($10\ mA/cm^2$) | Hole injection layer | Hole transport layer | Hole adjusting layer | Voltage (V) | Efficiency (cd/A) | CIE_x | CIE-y |
|---|---|---|---|---|---|---|---|
| Example 12 | A1 | Compound 3 | HT2 | 3.65 | 7.79 | 0.135 | 0.093 |
| Example 13 | A1 | Compound 4 | HT2 | 3.56 | 7.82 | 0.135 | 0.093 |
| Example 14 | A1 | Compound 5 | HT2 | 3.68 | 8.12 | 0.135 | 0.093 |
| Example 15 | A2 + Compound 3 | Compound 3 | HT2 | 3.61 | 8.05 | 0.135 | 0.094 |
| Example 16 | A2 + Compound 5 | Compound 5 | HT2 | 3.71 | 7.99 | 0.135 | 0.093 |
| Example 17 | A2 + HT1 | HT1 | Compound 1 | 3.69 | 8.01 | 0.135 | 0.093 |
| Comparative Example 3 | A1 | HT1 | HT2 | 3.91 | 7.12 | 0.135 | 0.093 |
| Comparative Example 4 | A2 + HT1 | HT1 | HT2 | 3.98 | 7.22 | 0.135 | 0.093 |
| Comparative Example 5 | A1 | HT3 | HT2 | 4.02 | 6.99 | 0.135 | 0.093 |
| Comparative Example 6 | A1 | HT4 | HT2 | 3.99 | 7.02 | 0.135 | 0.093 |
| Comparative Example 7 | A2 + HT3 | HT3 | HT2 | 3.87 | 7.12 | 0.135 | 0.093 |
| Comparative Example 8 | A2 + HT4 | HT4 | HT2 | 4.02 | 6.87 | 0.135 | 0.093 |

As in Table 1 and Table 2, it can be seen that the compounds used in Examples 1 to 17 were used as a hole injection layer, a hole transport layer, and a hole adjusting layer in an organic light emitting device, exhibit low voltage and high efficiency characteristics based on an excellent ability to transport holes as compared to a benzidine-type material, and serve to block electrons and adjust holes based on high triplet energy, which is a characteristic of a spiro material, as compared to a carbazole-type hole adjusting layer.

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:

1. A compound of the following Chemical Formula 2:

[Chemical Formula 2]

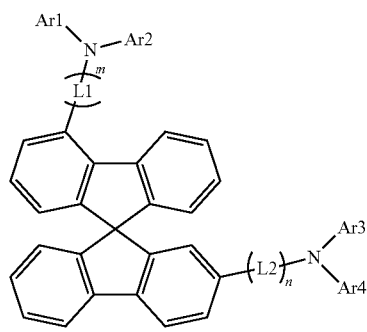

in Chemical Formula 2,
Ar1 to Ar4 are the same as or different from each other, and are each independently a substituted or unsubstituted aryl group or a substituted or unsubstituted heterocyclic group, or Ar1 and Ar2 are linked to each other by E1, or Ar3 and Ar4 are linked to each other by E2,
E1 and E2 are the same as or different from each other, and are each independently a direct bond, CRR', NR, O, or S,
L1 and L2 are the same as or different from each other, and are each independently a direct bond, or a substituted or unsubstituted arylene or a substituted or unsubstituted heteroarylene, n and m are the same as or different from each other, and are each an integer of 0 to 3, and
R' are the same as or different from each other, and are each independently hydrogen; deuterium; a halogen group; a nitrile group; a substituted or unsubstituted alkyl group; a substituted or unsubstituted cycloalkyl group; a substituted or unsubstituted alkoxy group; a substituted or unsubstituted aryloxy group; a substituted or unsubstituted aralkyl group; a substituted or unsubstituted aralkenyl group; a substituted or unsubstituted alkylaryl group; a substituted or unsubstituted aryl group; or a substituted or unsubstituted heterocyclic group, and p and q are the same as or different from each other, and are each an integer of 0 to 7,
wherein at least one of Ar1 to Ar4 is an unsubstituted phenyl, or at least one of Ar1 and Ar2, or Ar3 and Ar4 are bonded to each other through CRR', NR, S, or O, and R and R' are each independently a substituted or unsubstituted alkyl group.

2. The compound of claim 1, wherein Ar1 to Ar4 are the same as or different from each other, and are each independently a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted phenanthryl group, a substituted or unsubstituted triphenylene group, a substituted or unsubstituted fluorenyl group, a substituted or unsubstituted spirobifluorenyl group, a substituted or unsubstituted dibenzothiophene group, a substituted or unsubstituted dibenzofuran group, or a substituted or unsubstituted carbazole group.

3. The compound of claim 1, wherein Ar1 and Ar2 or Ar3 and Ar4 are bonded to each other through CRR', NR, S, or O, and the definitions of R and R' are the same as those described in Chemical Formula 1.

4. The compound of claim 1, wherein Chemical Formula 4-2 is selected from the following structural formulae:

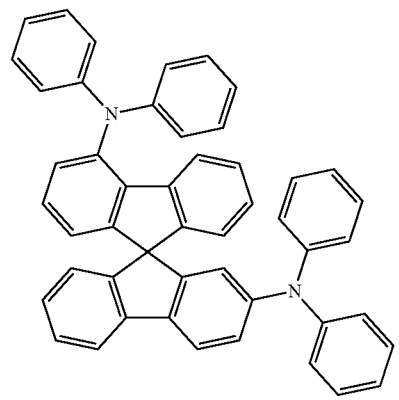

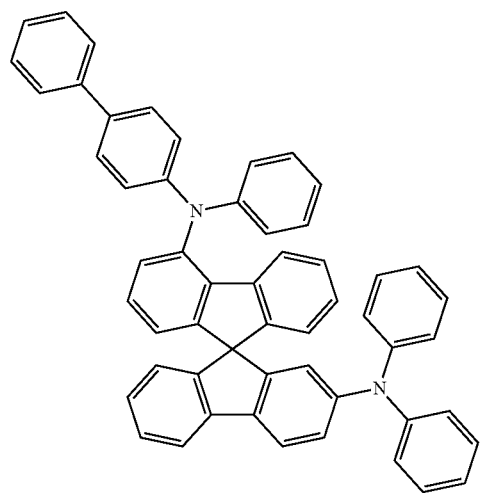

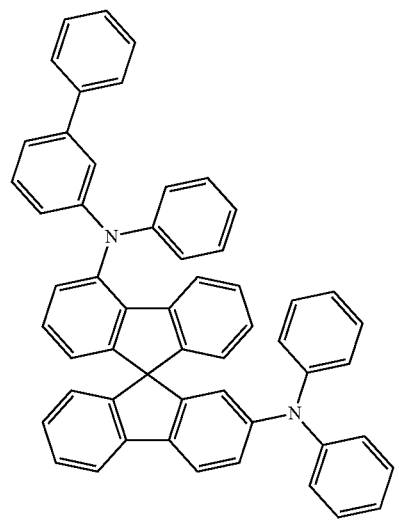

121
-continued
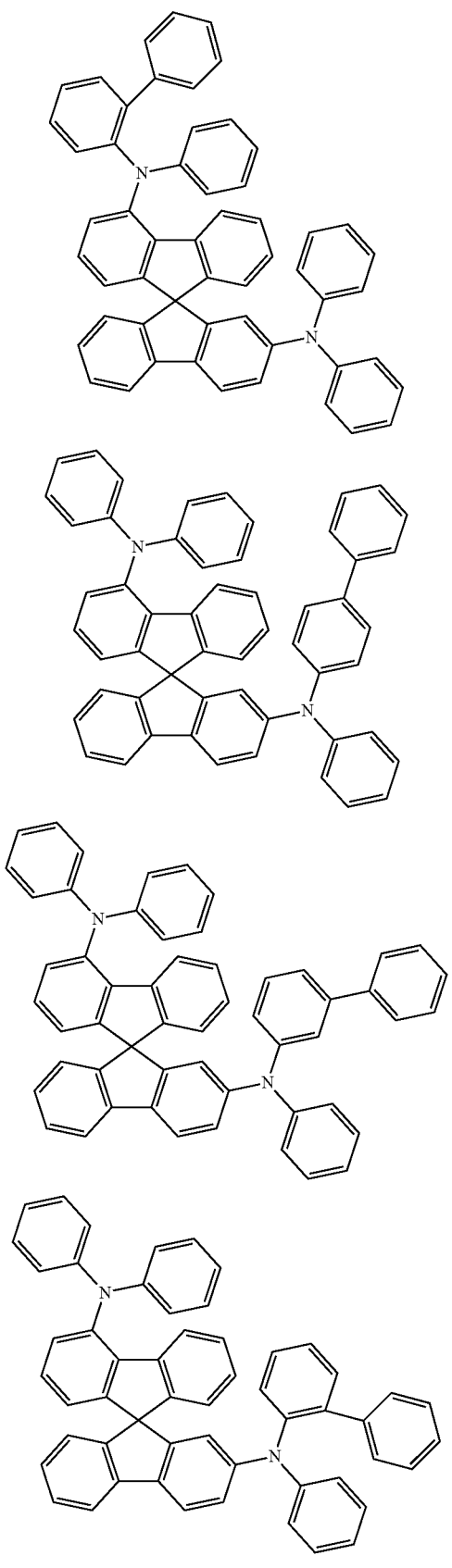
122
-continued
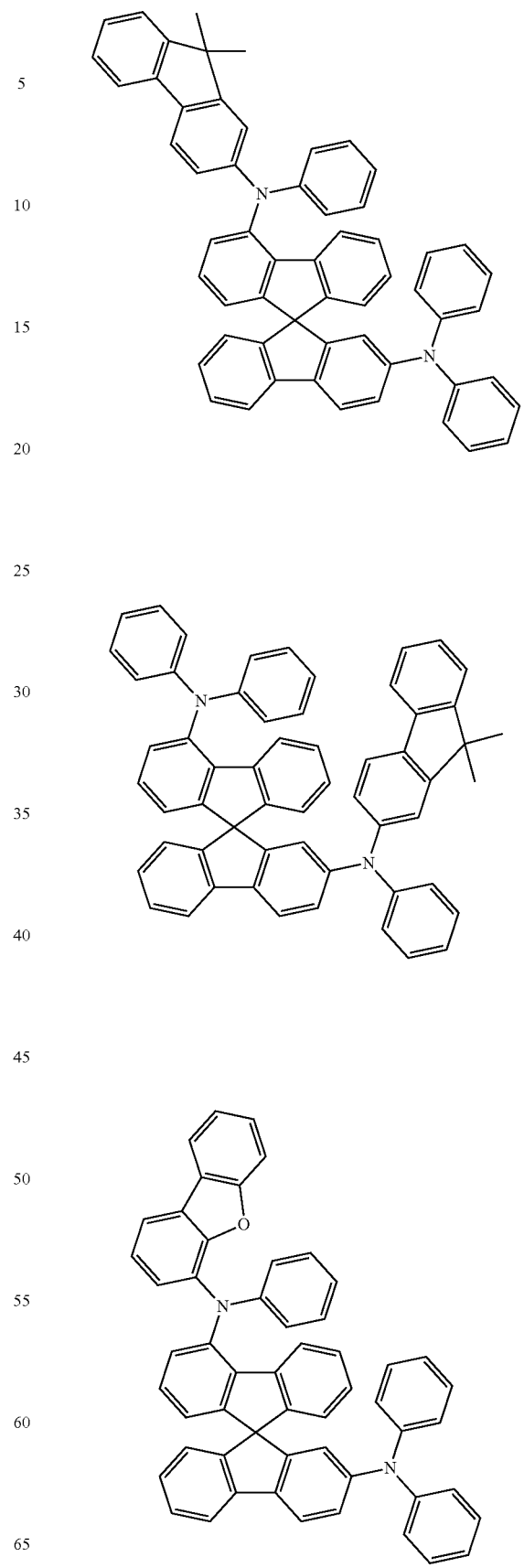

123
-continued
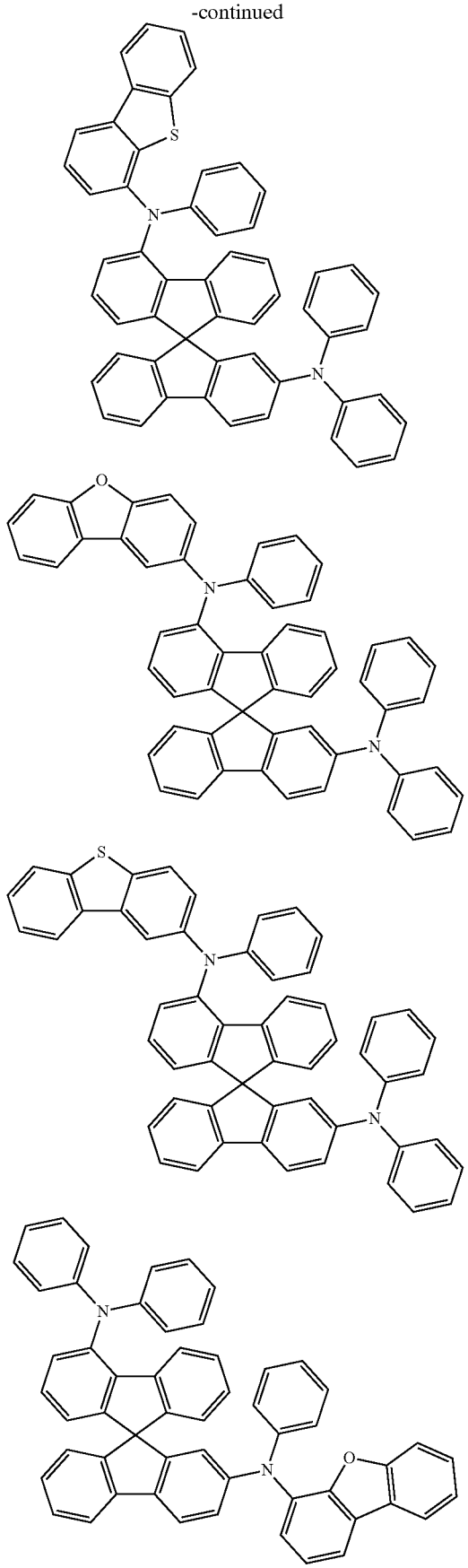
124
-continued
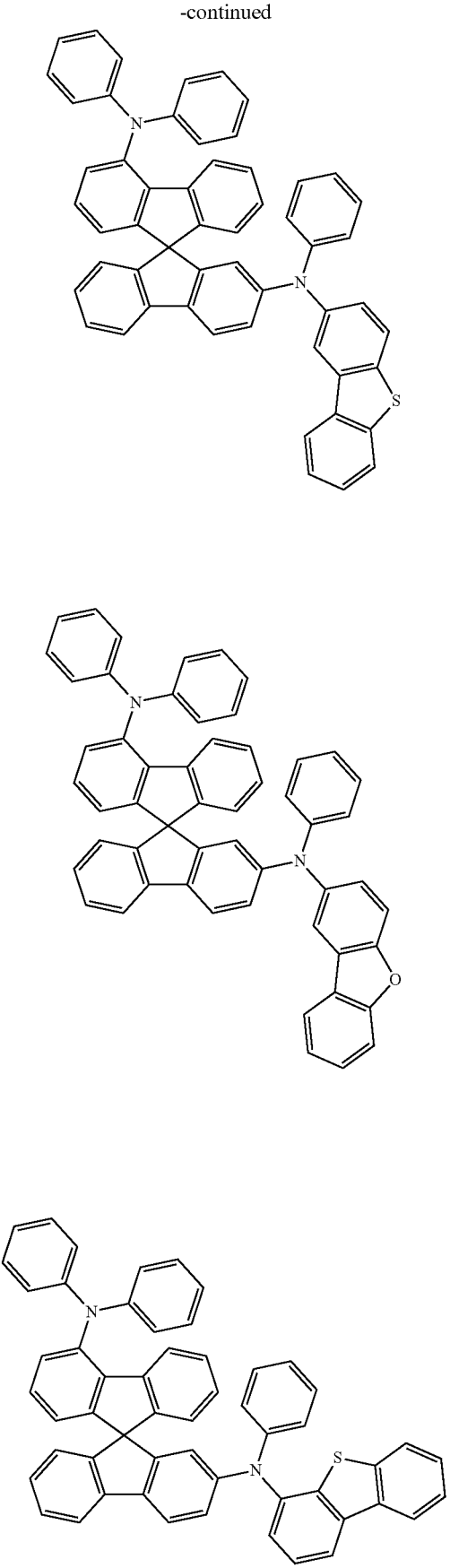

125
-continued
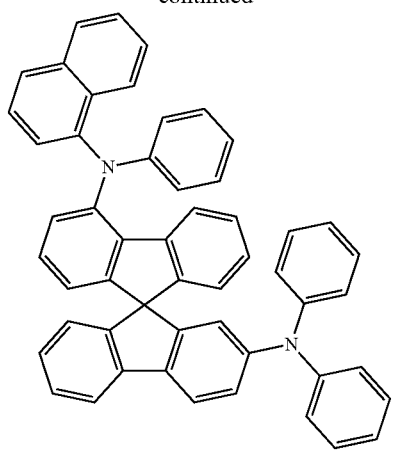
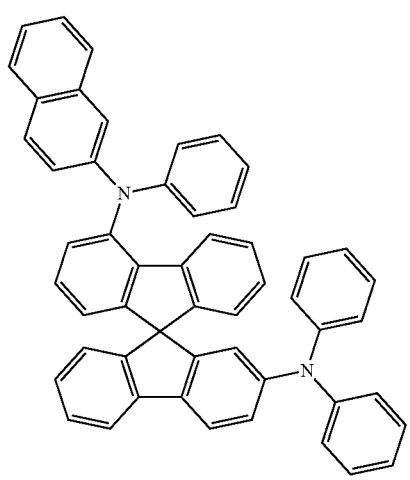
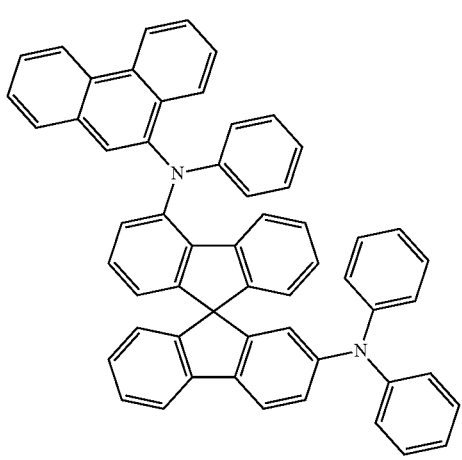
126
-continued
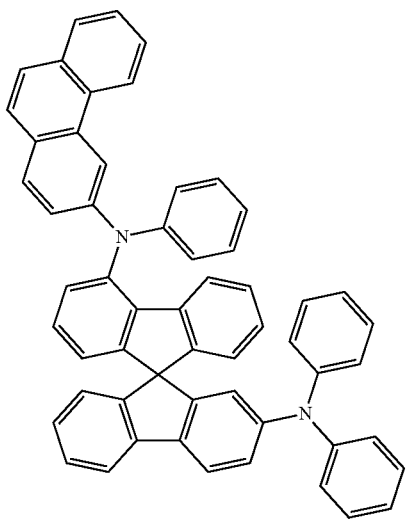
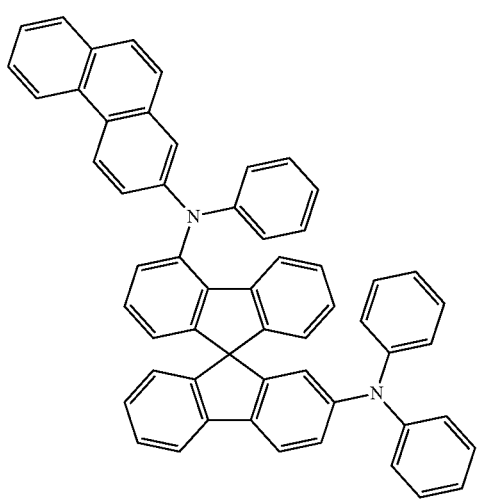
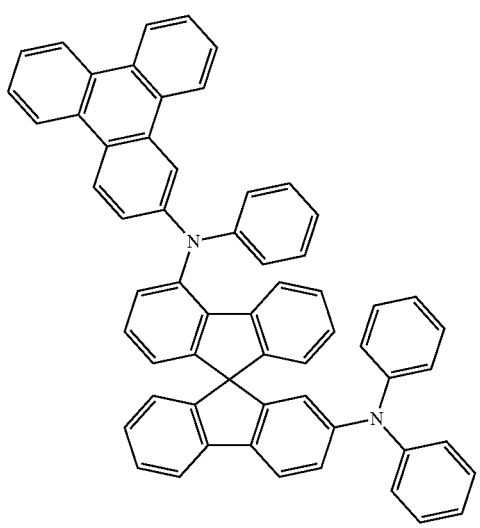

127
-continued
128
-continued
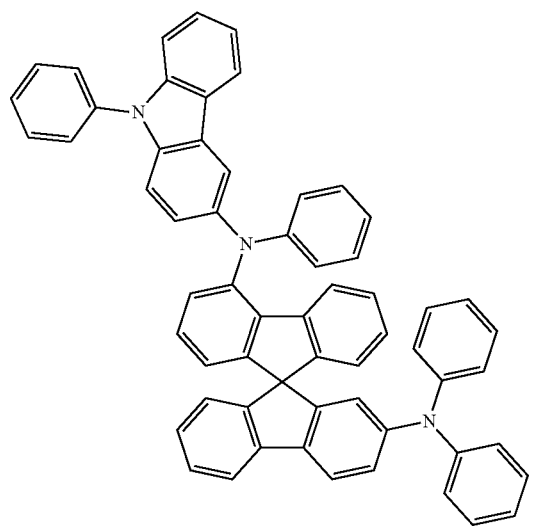
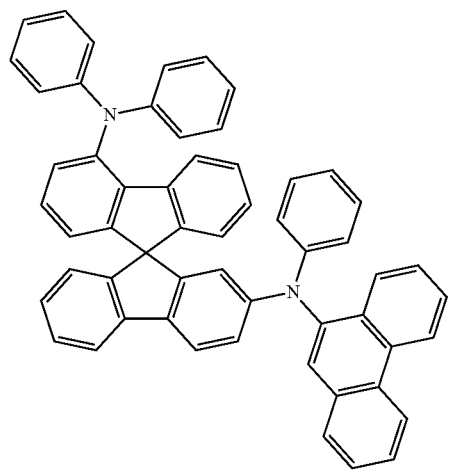
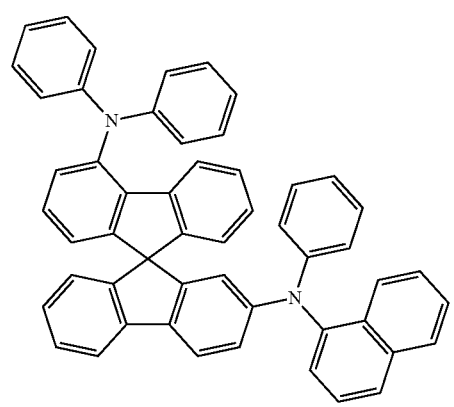
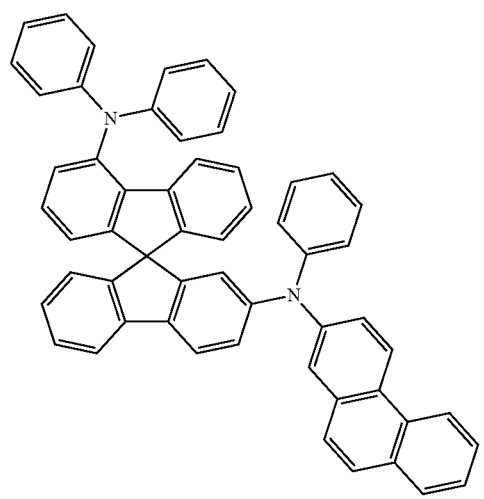
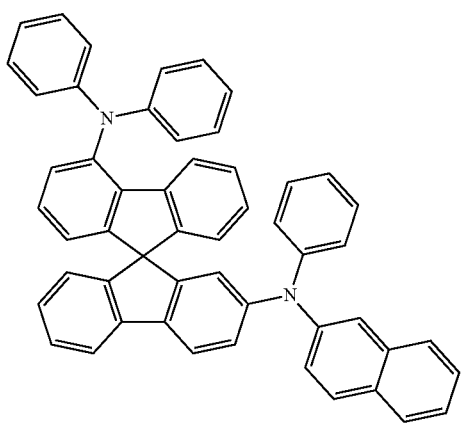
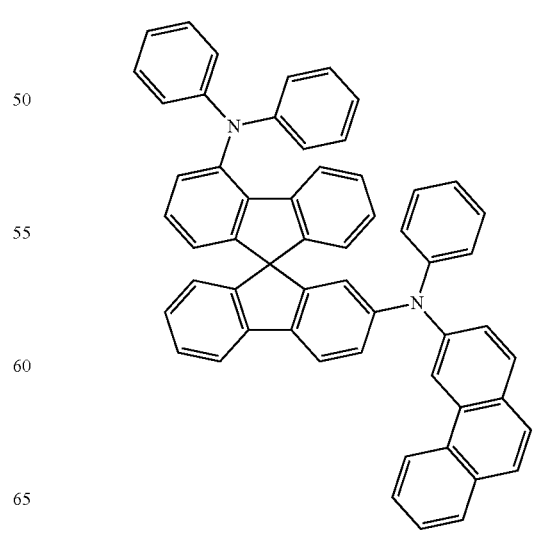

129
-continued
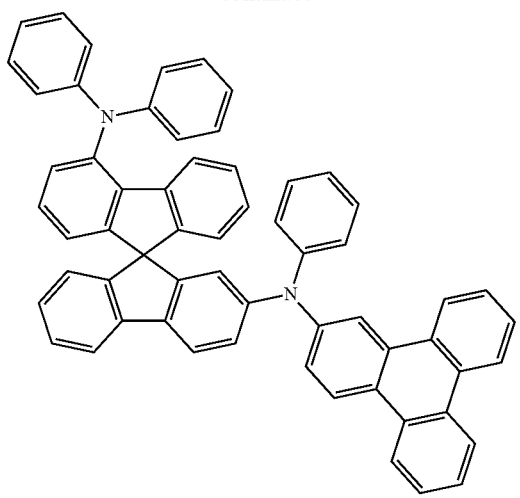
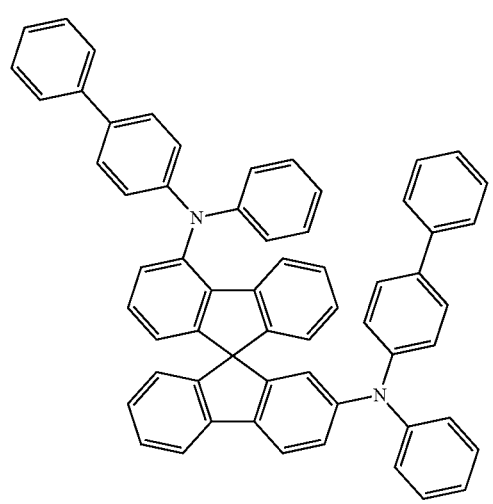
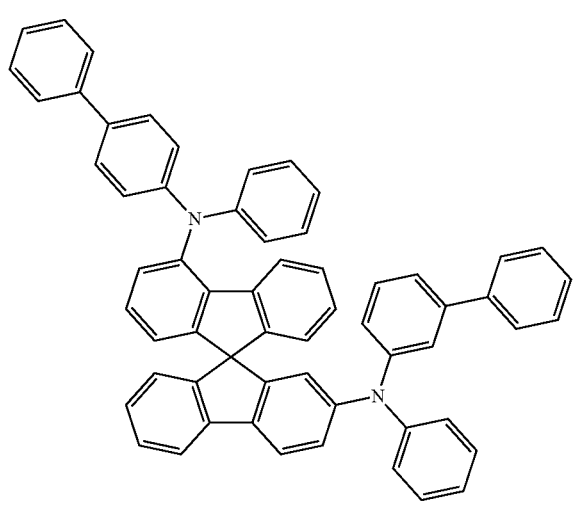
130
-continued
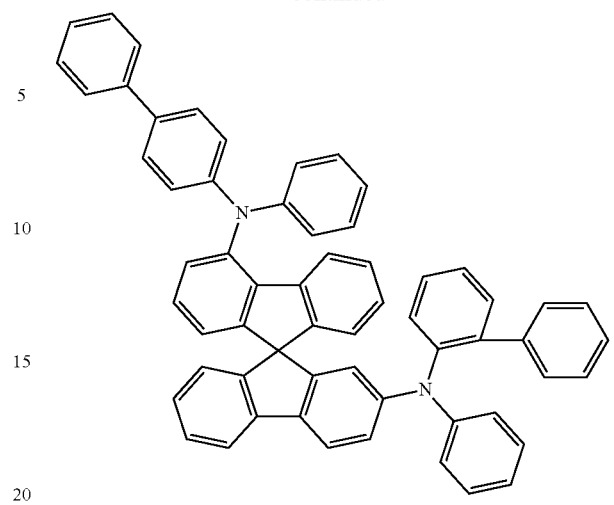
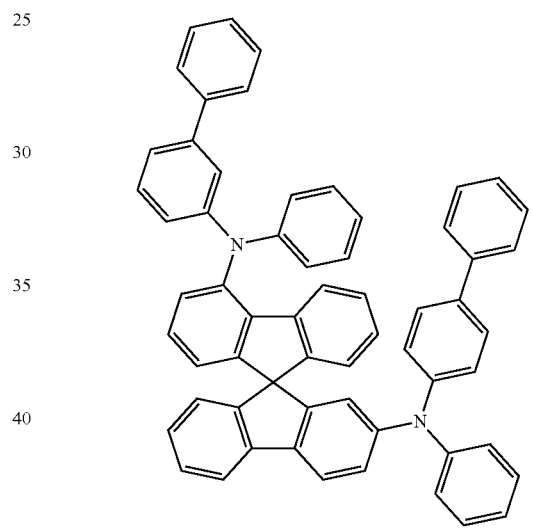
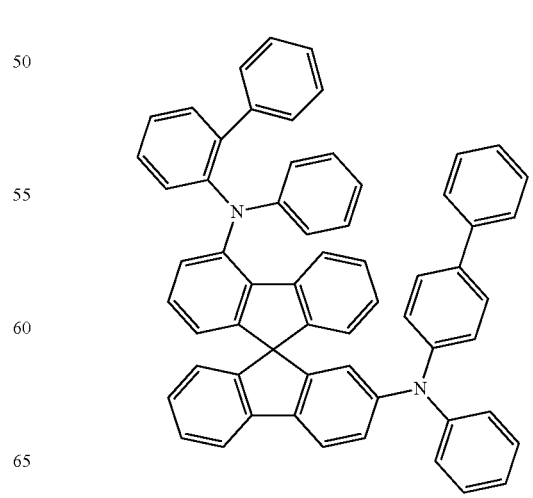

131
-continued
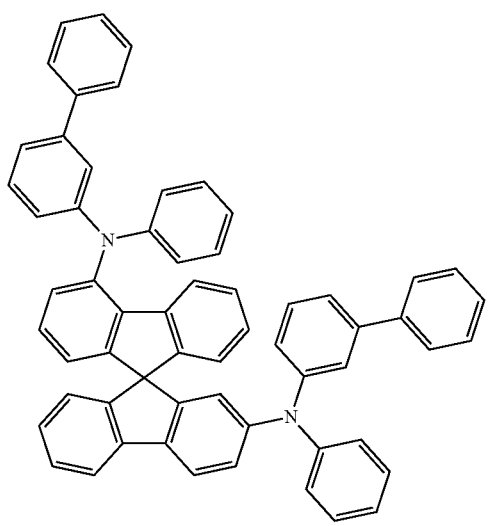
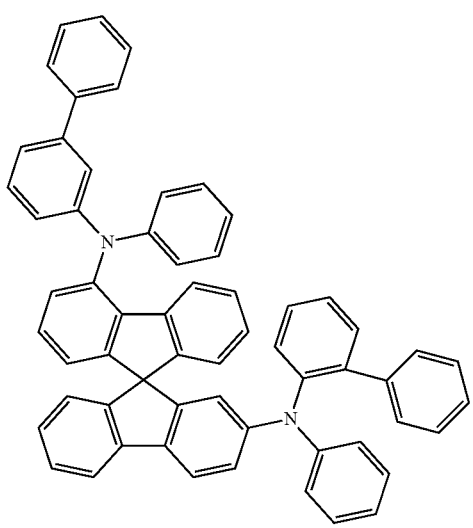
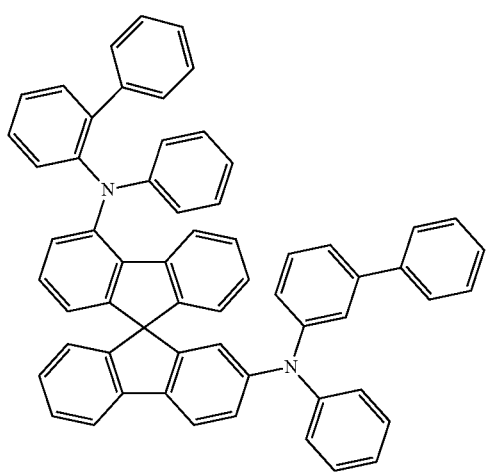
132
-continued
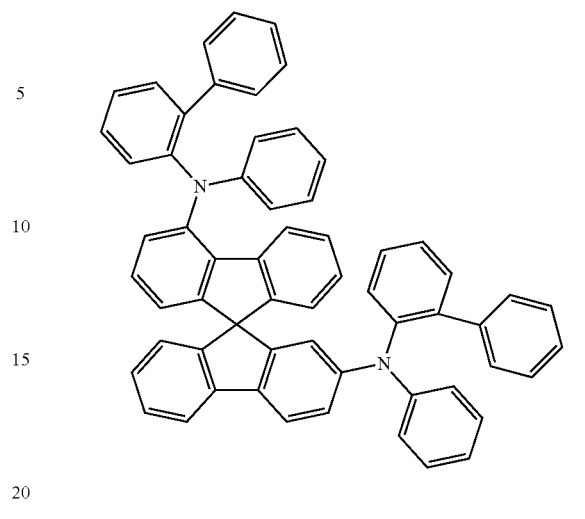
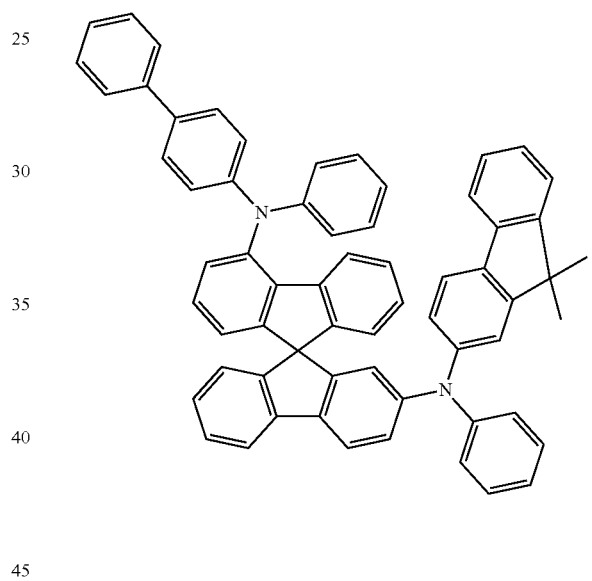
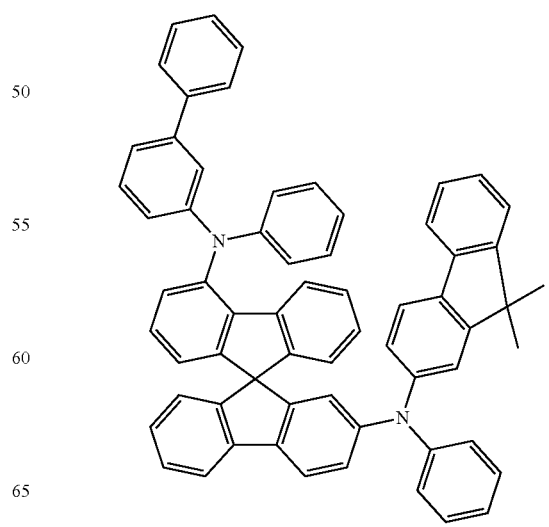

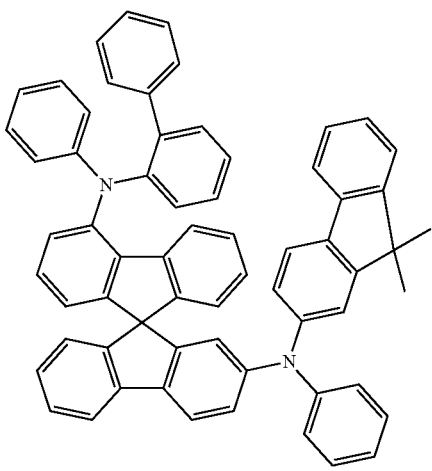
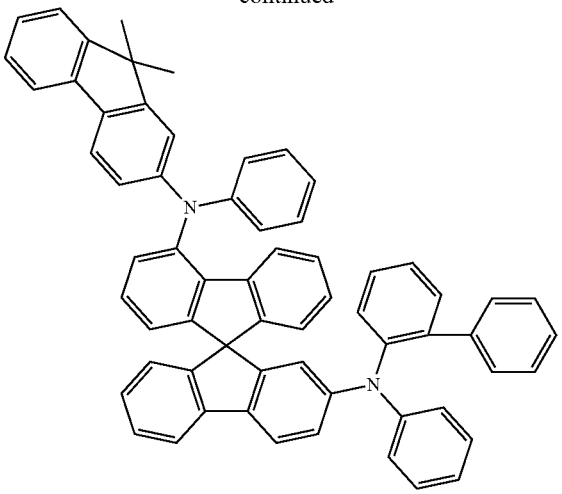
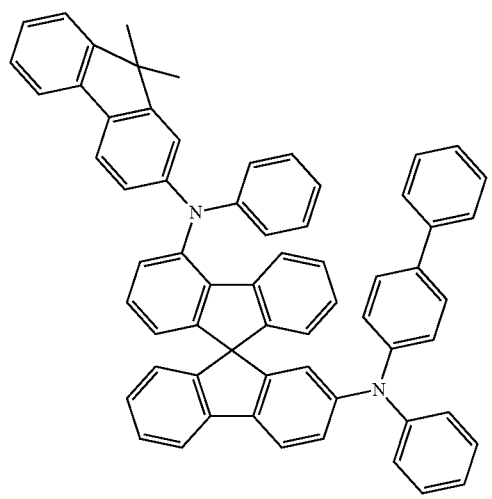
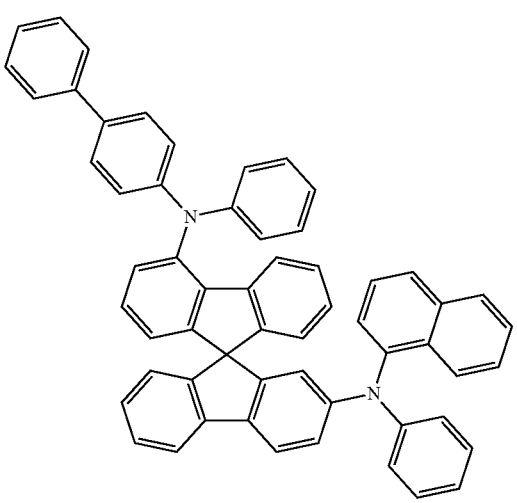
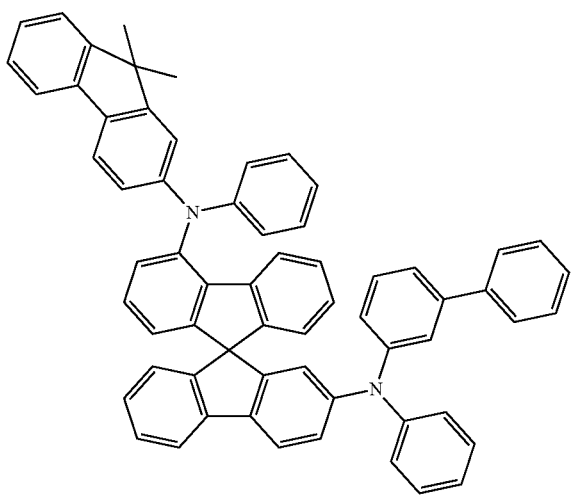
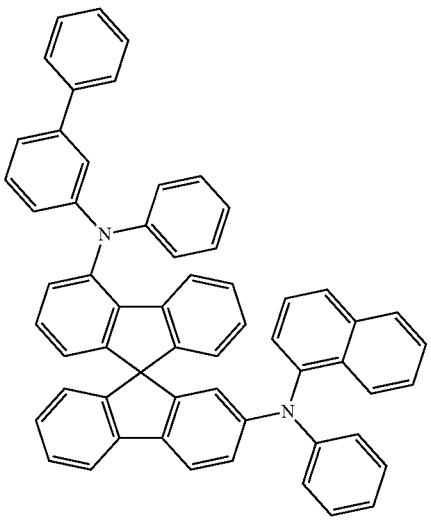

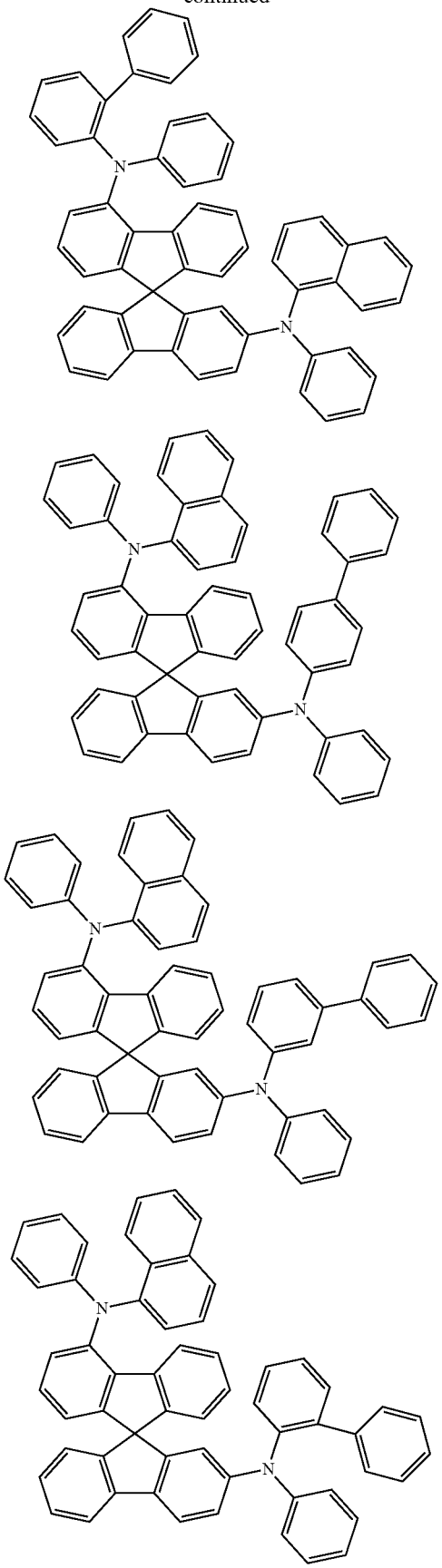
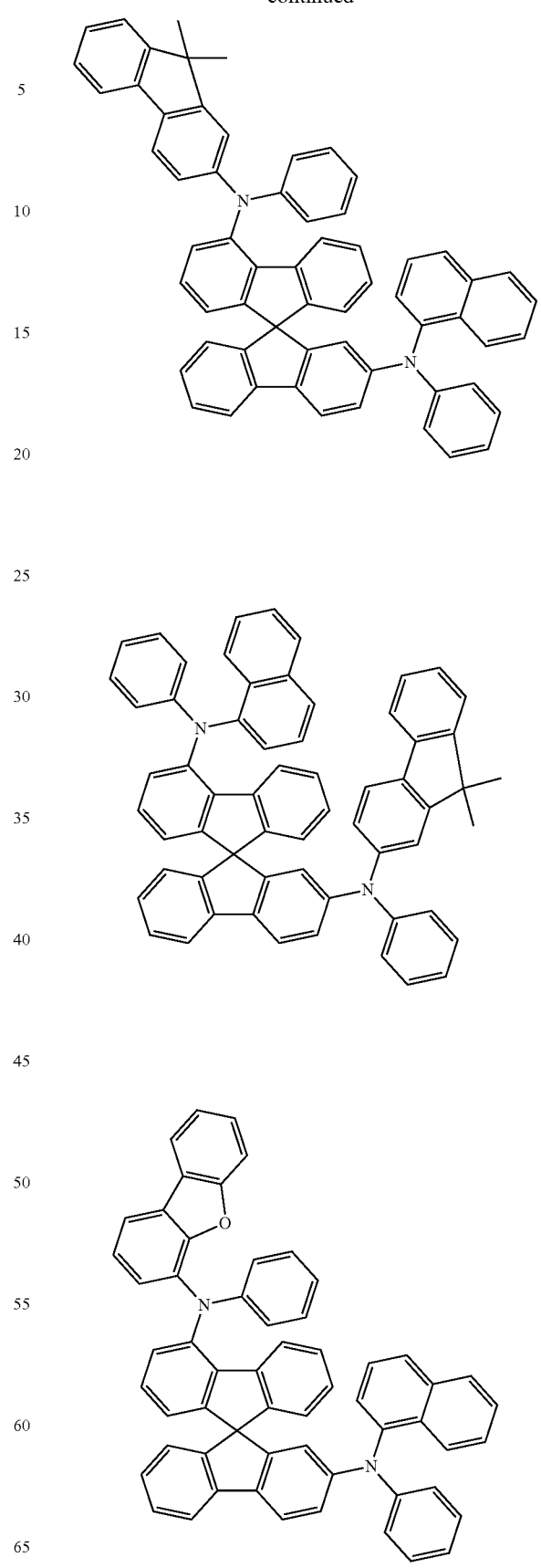

137
-continued
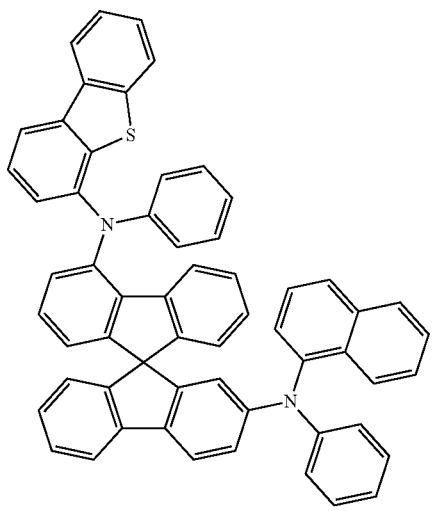
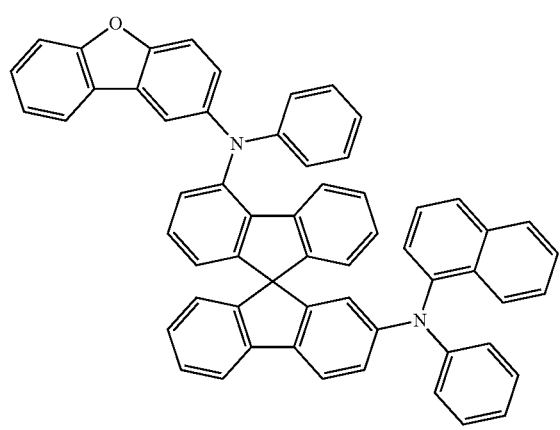
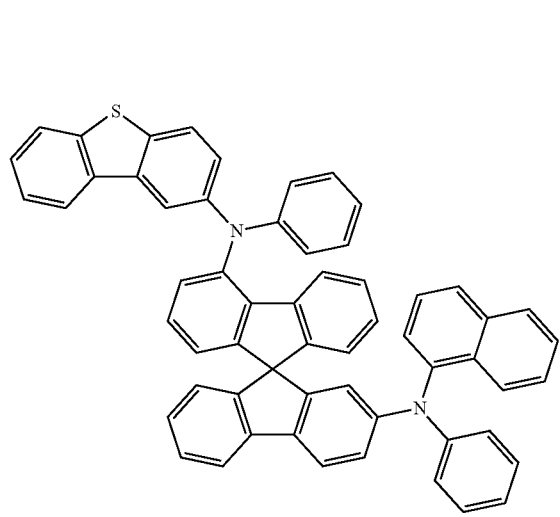
138
-continued
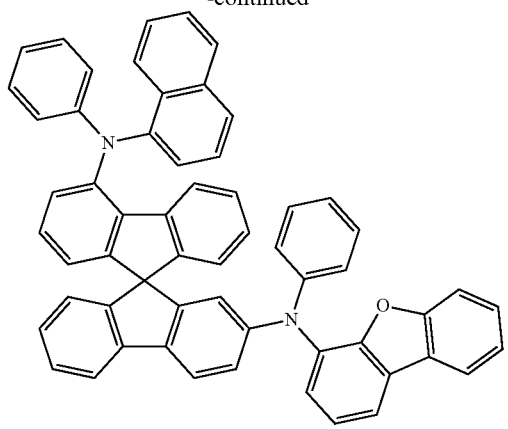
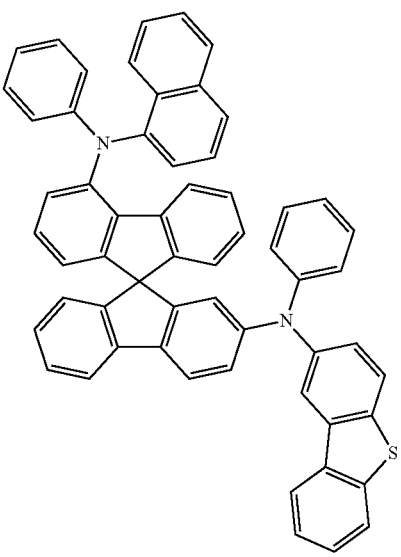
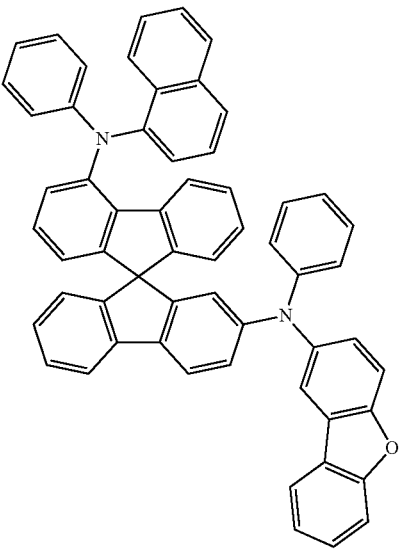

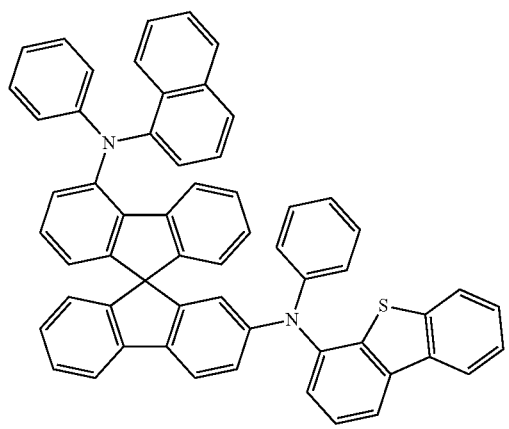
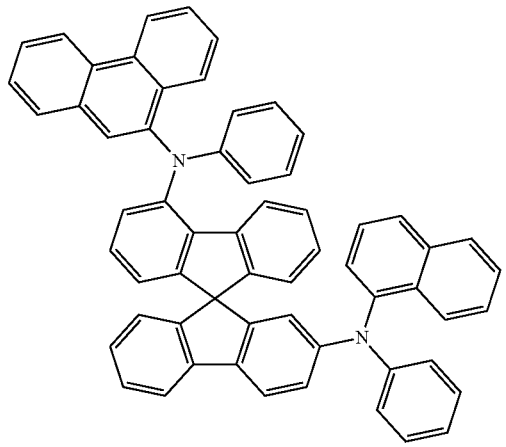
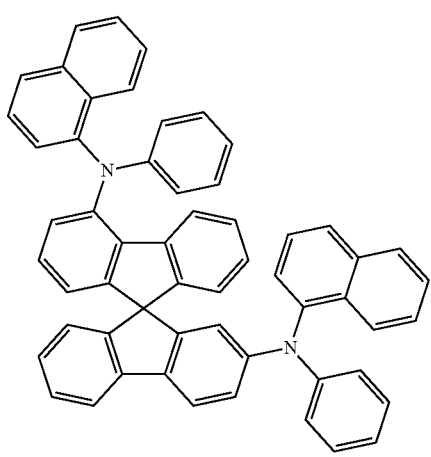
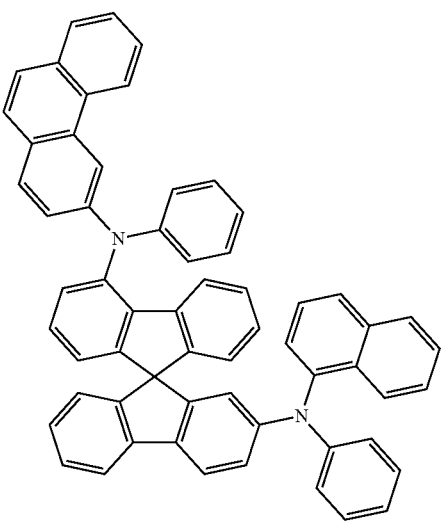
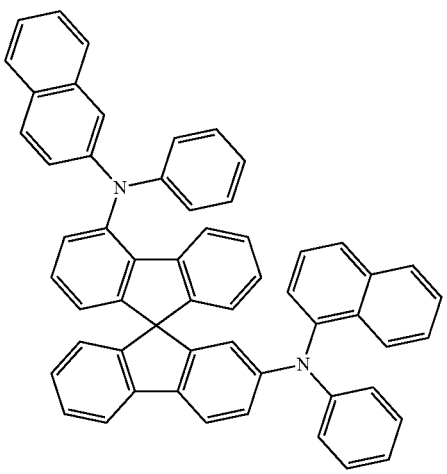
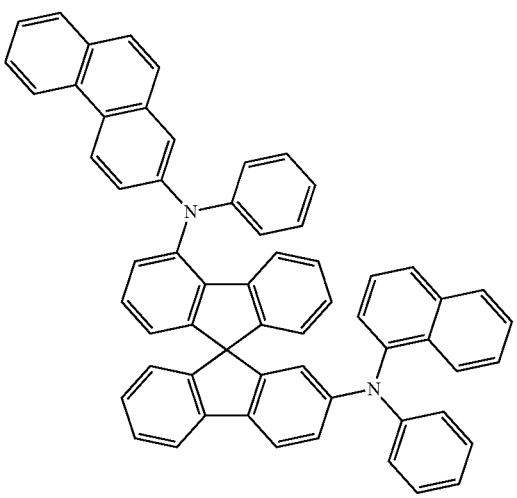

141
-continued
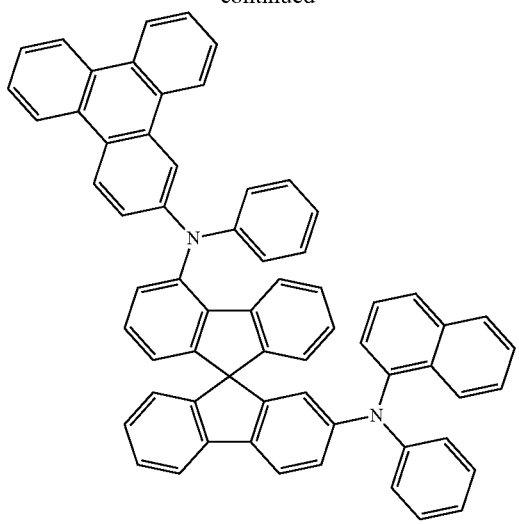
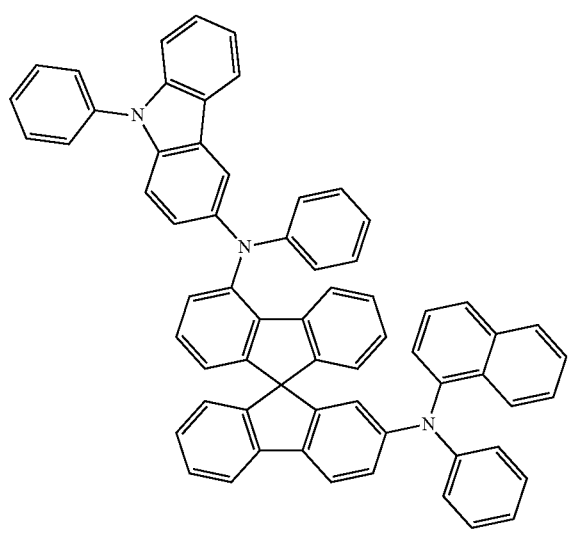
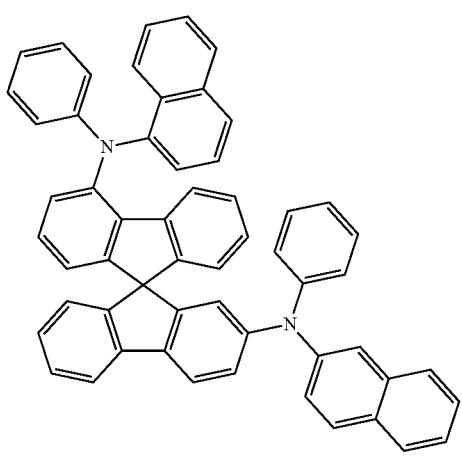
142
-continued
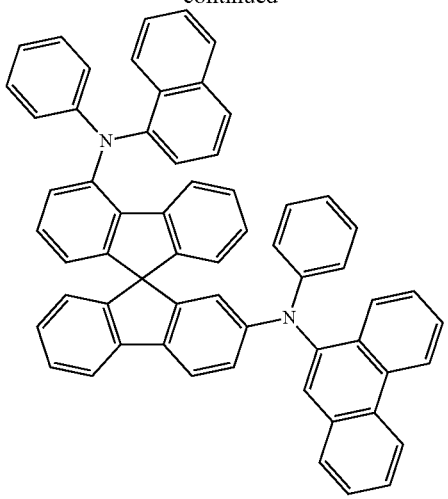
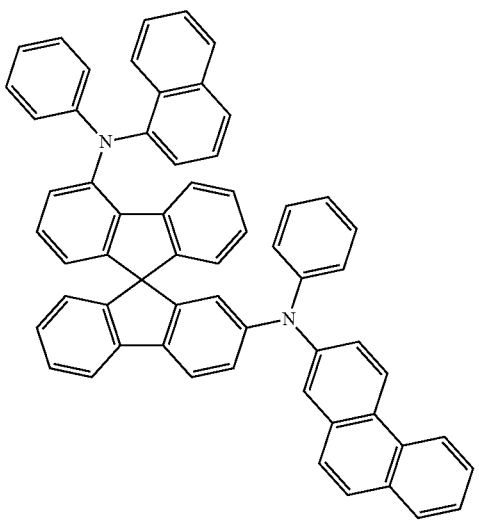
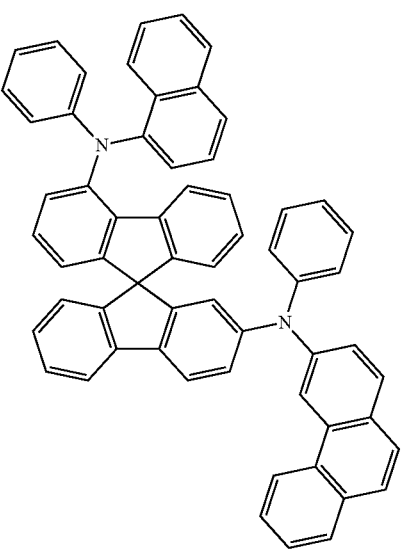

-continued
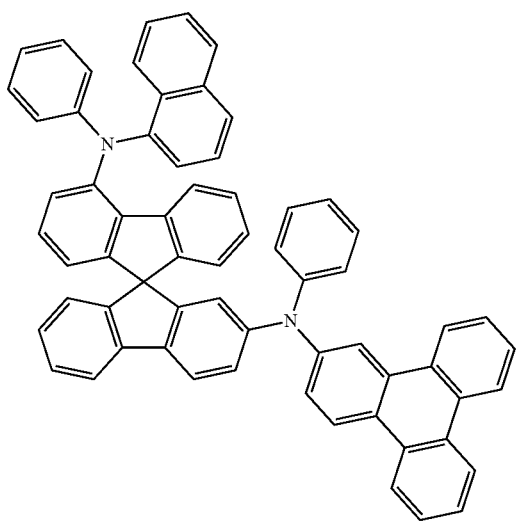
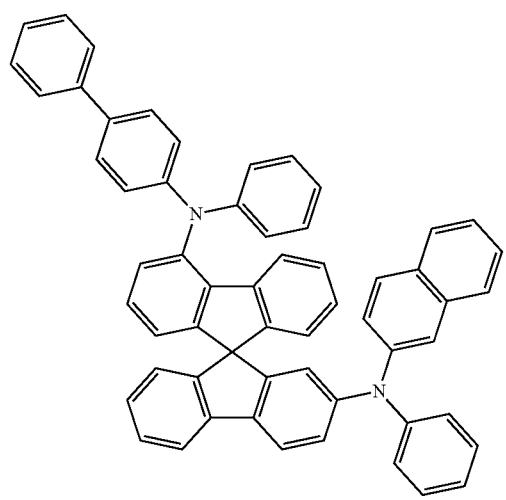
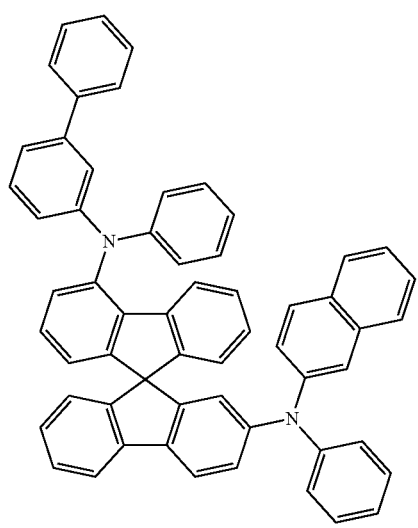
-continued
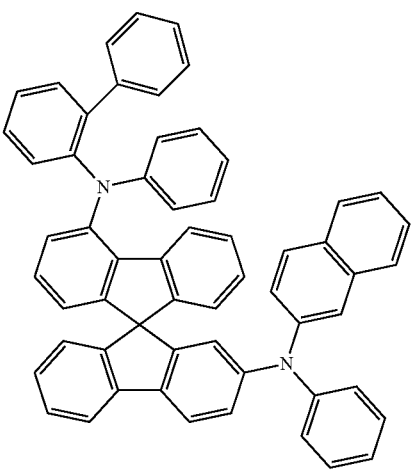
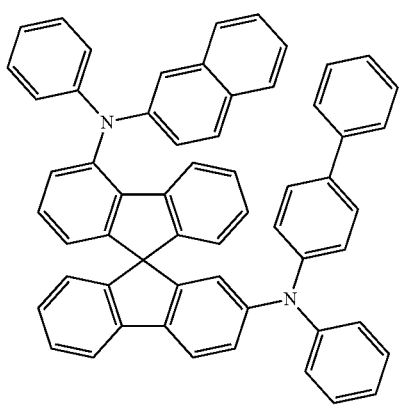
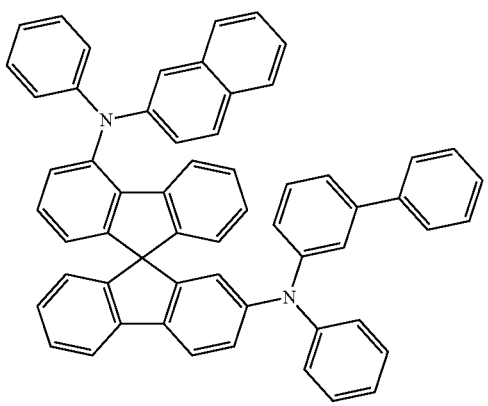
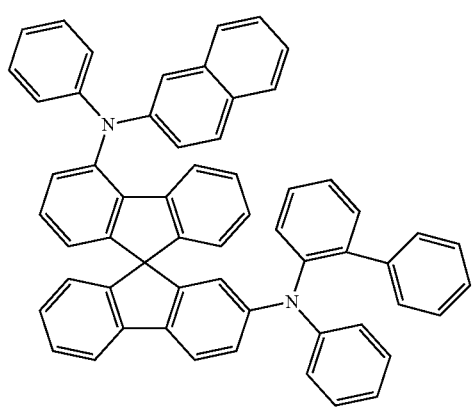

145
-continued
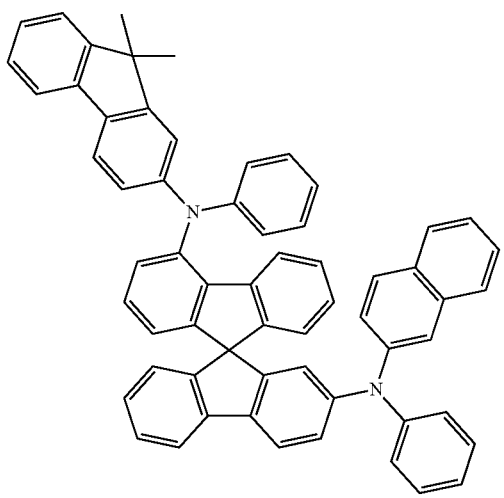
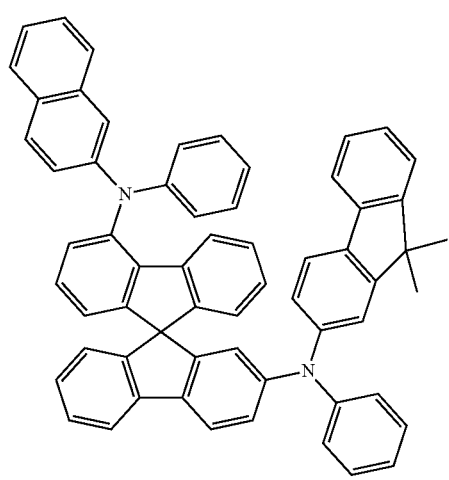
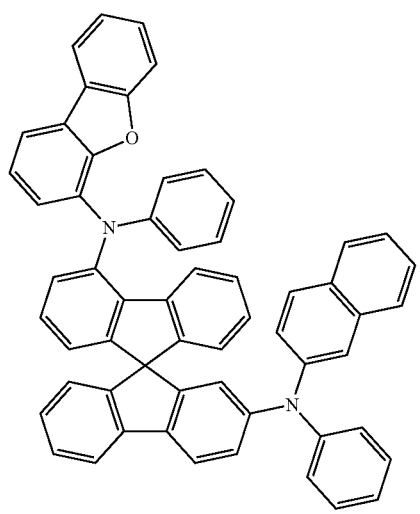
146
-continued
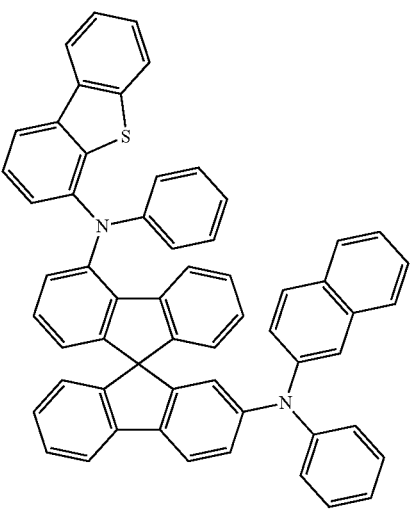
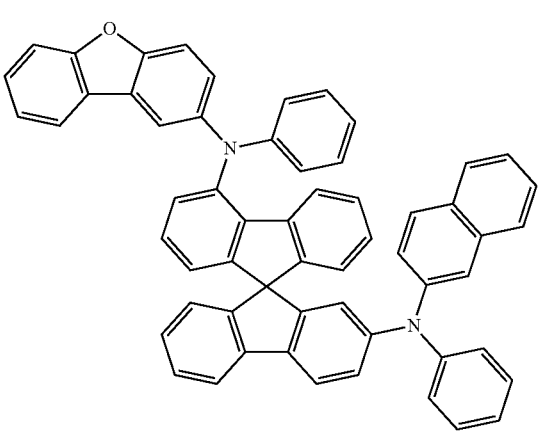
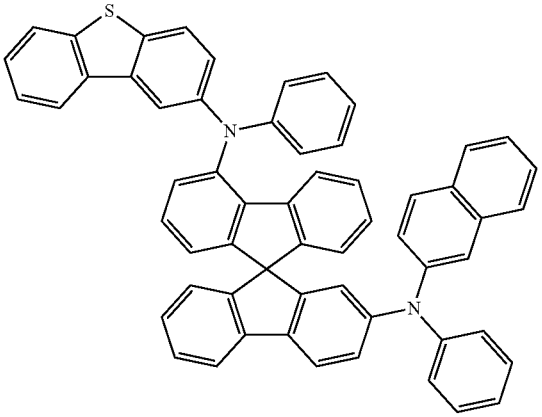

147
-continued
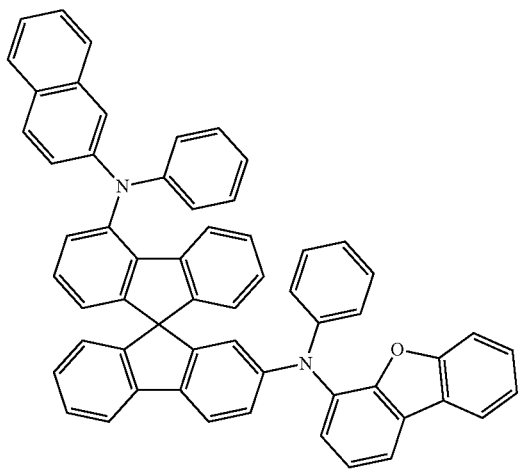
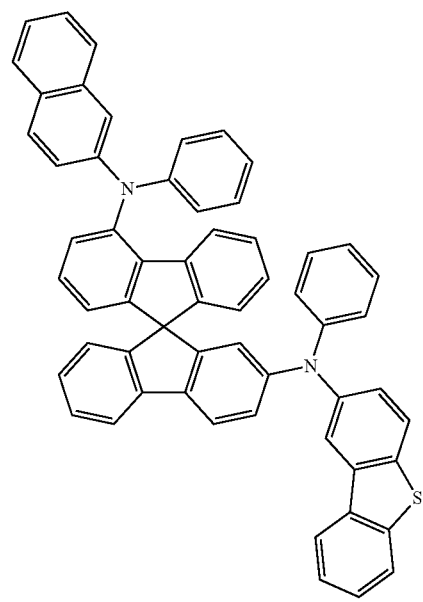
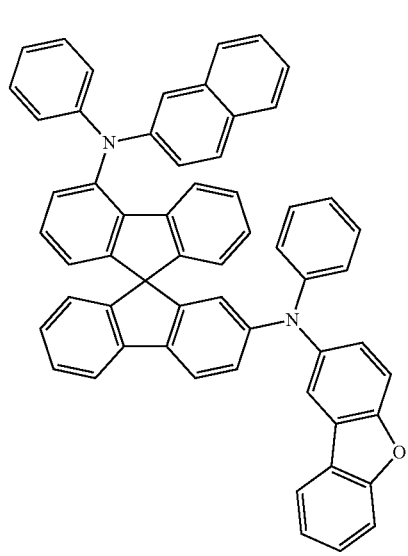
148
-continued
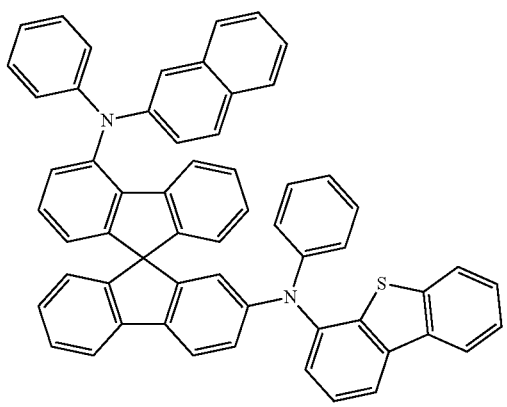
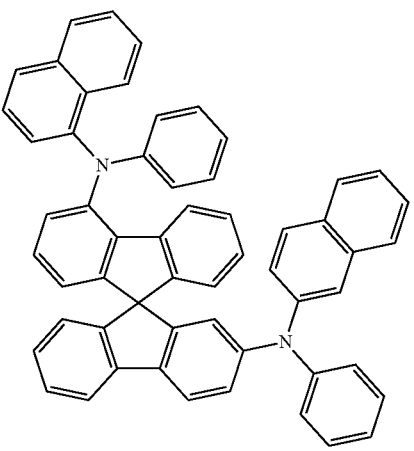
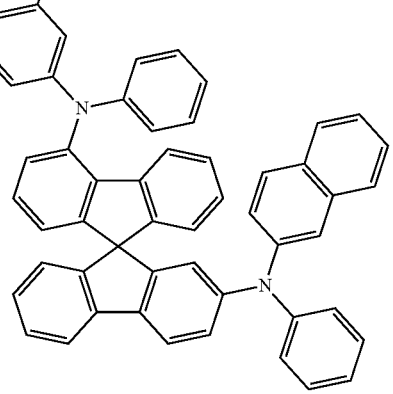

149
-continued
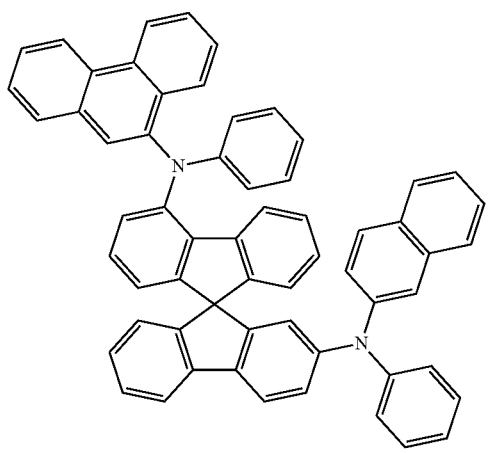
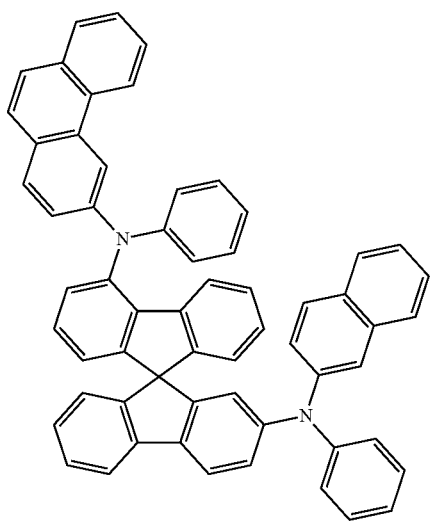
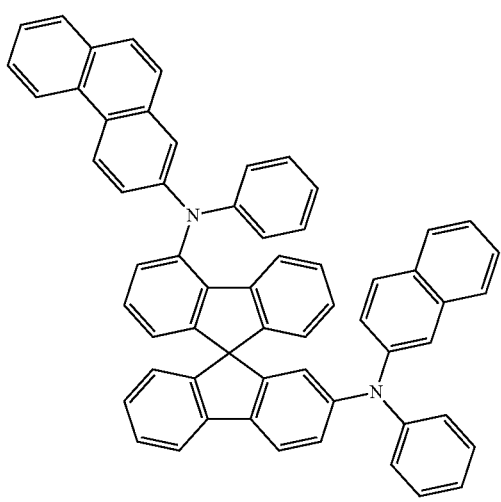
150
-continued
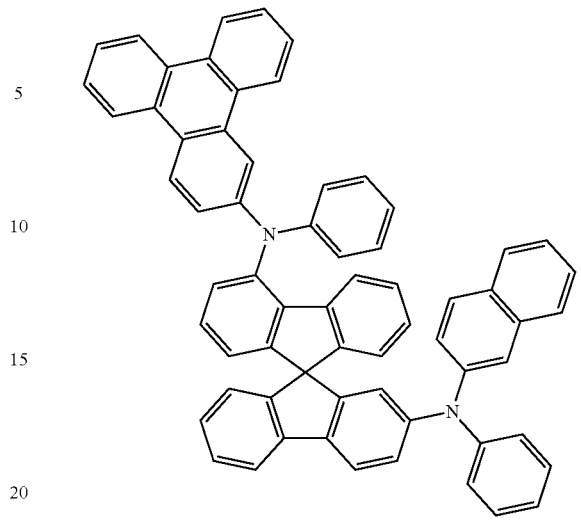
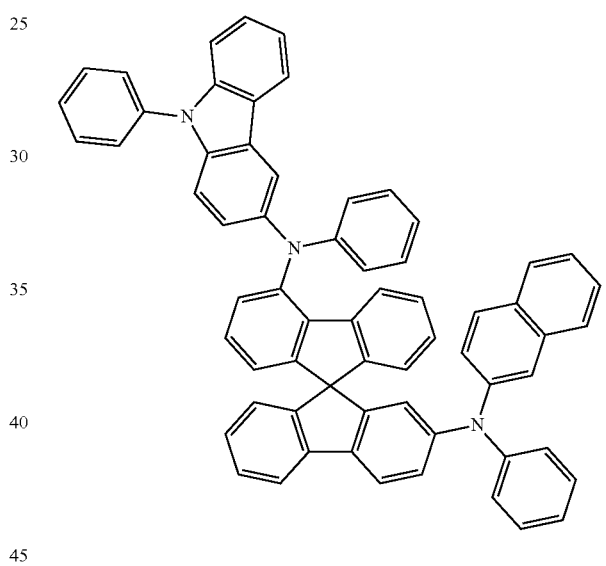
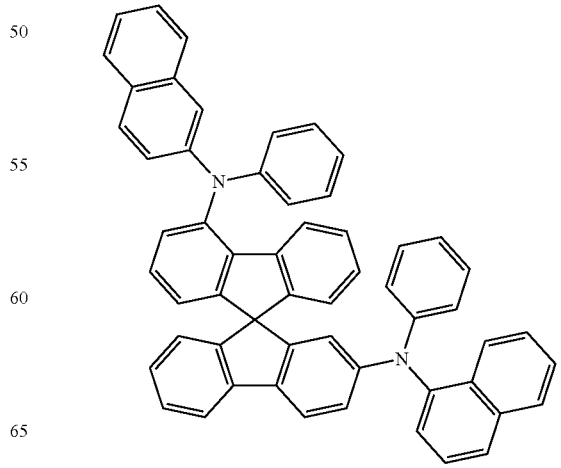

151
-continued
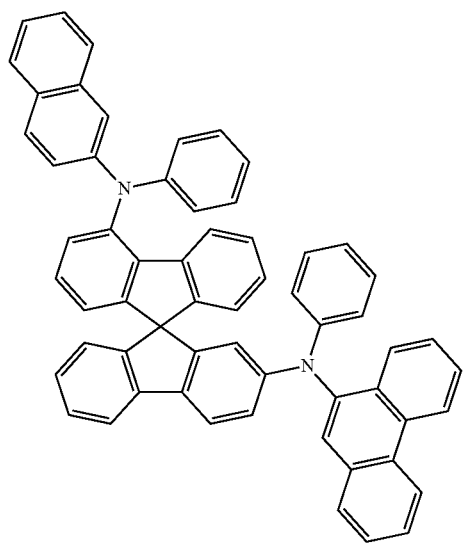
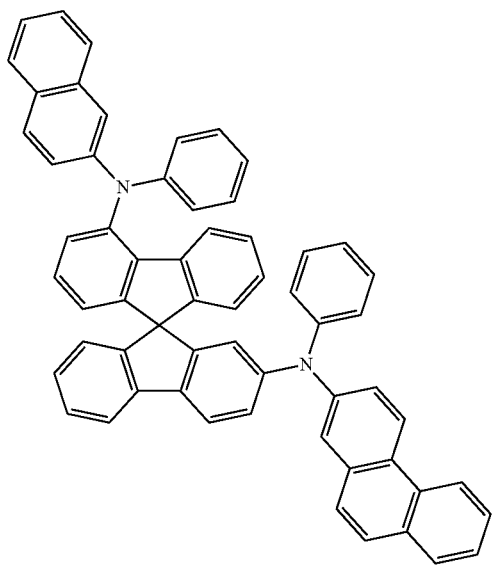
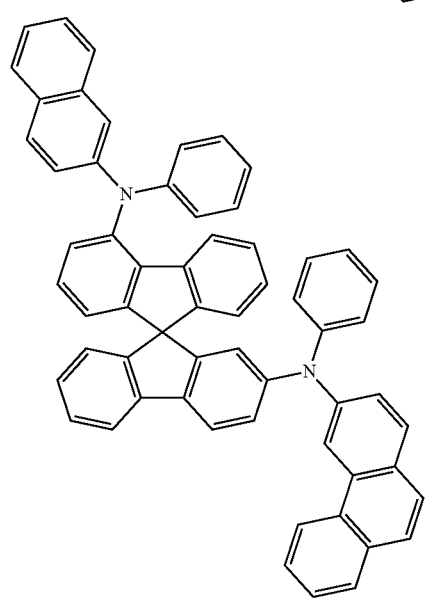
152
-continued
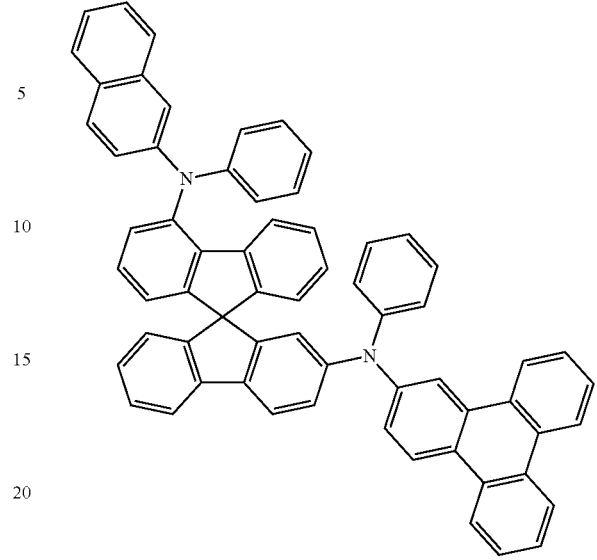

153
-continued
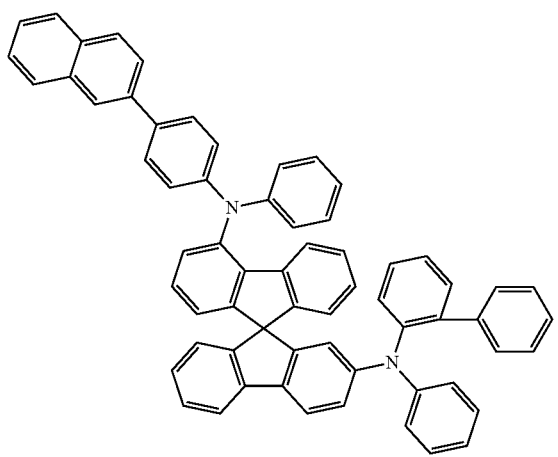
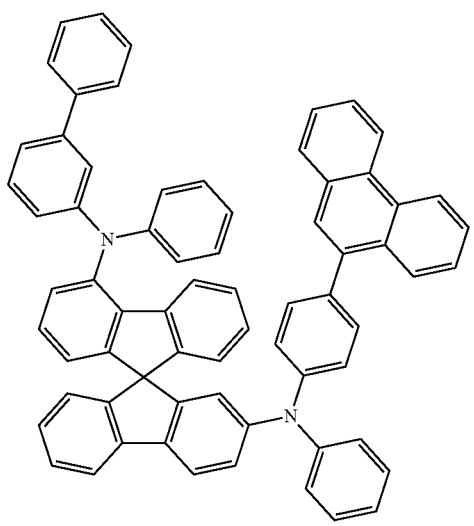
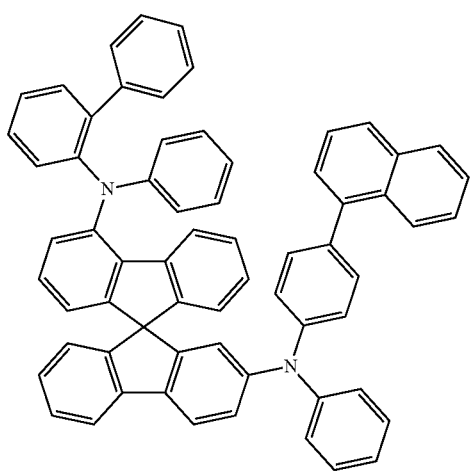
154
-continued
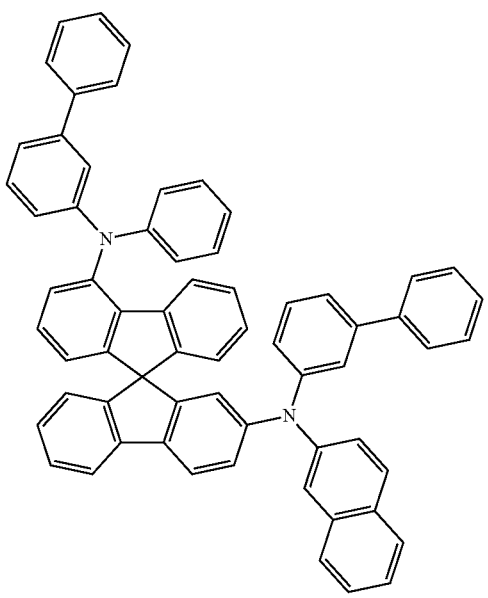
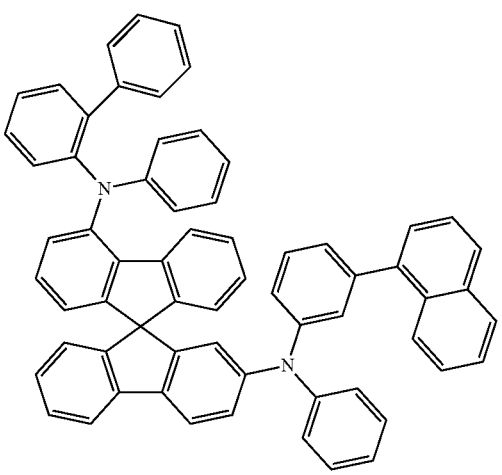

155
-continued
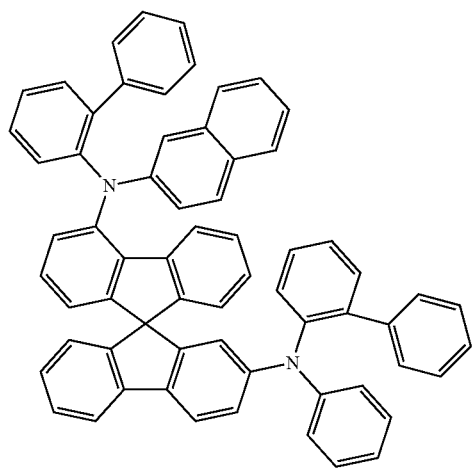
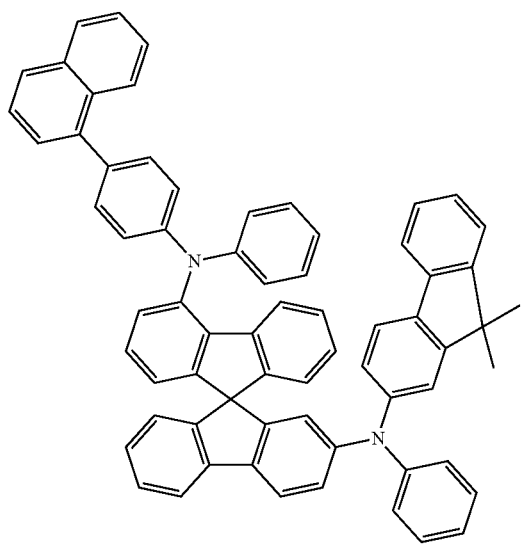
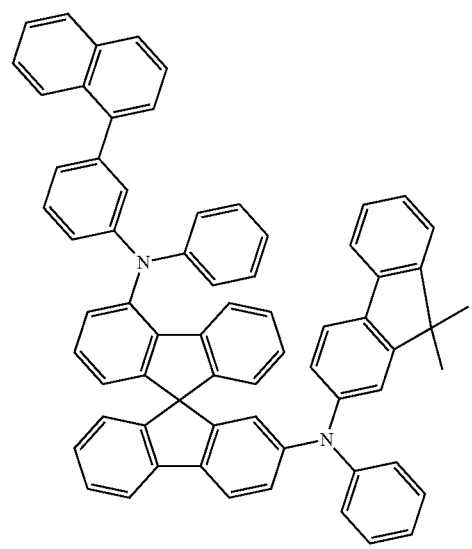
156
-continued
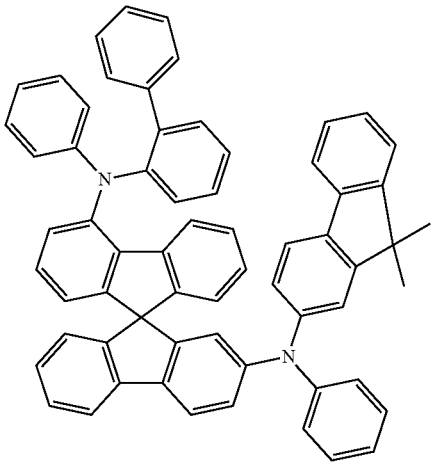
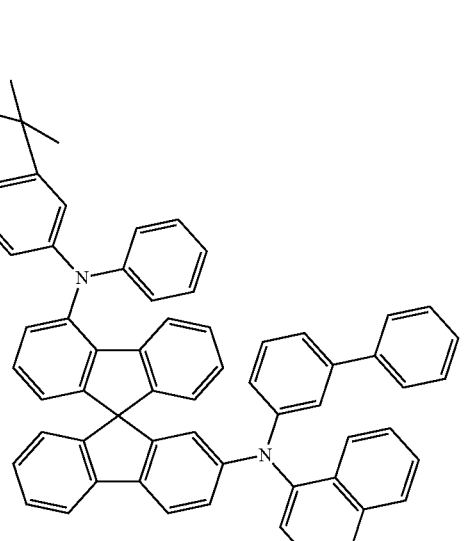

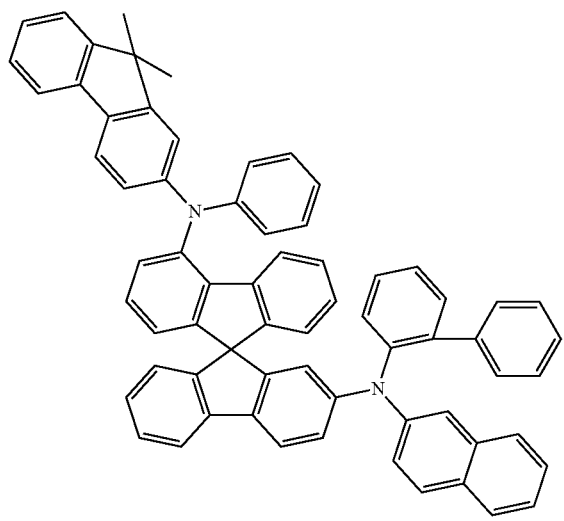
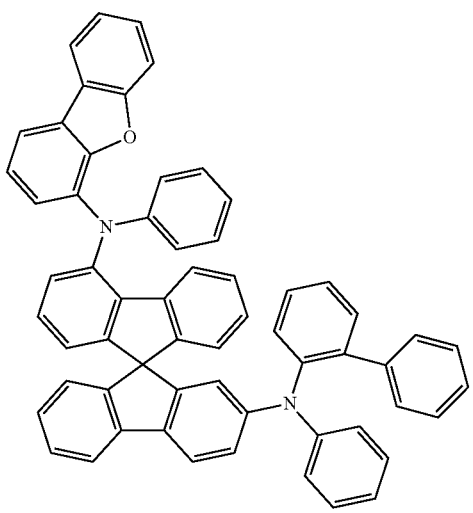
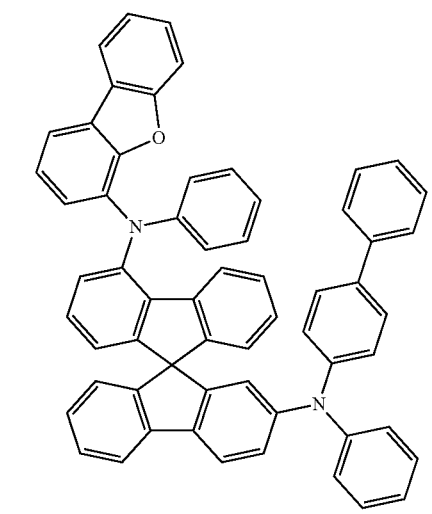
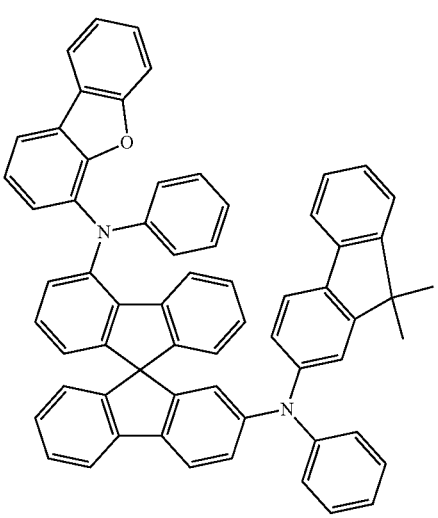
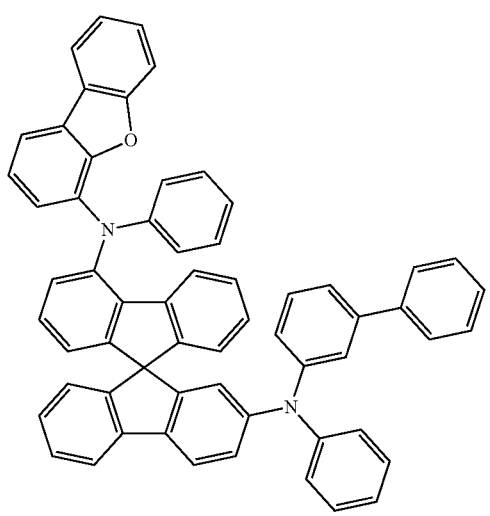
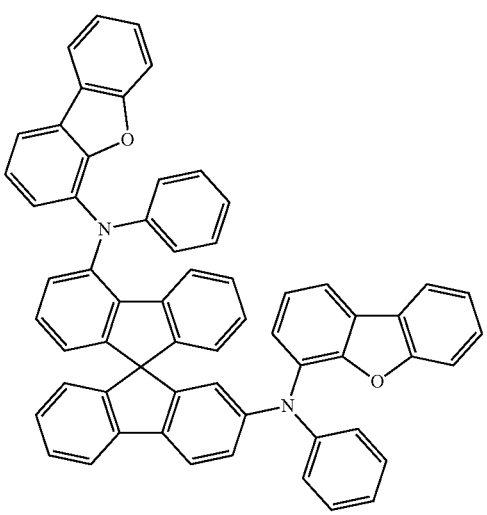

159
-continued
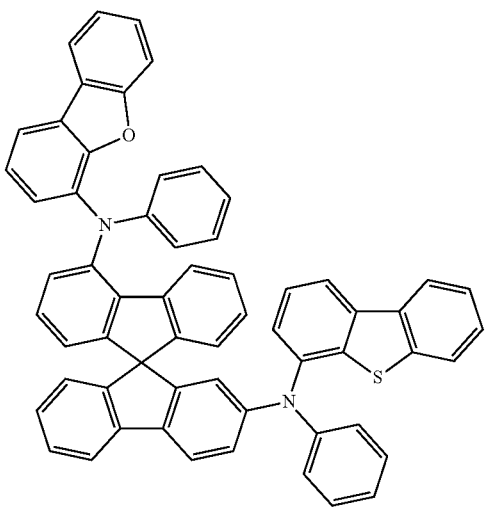
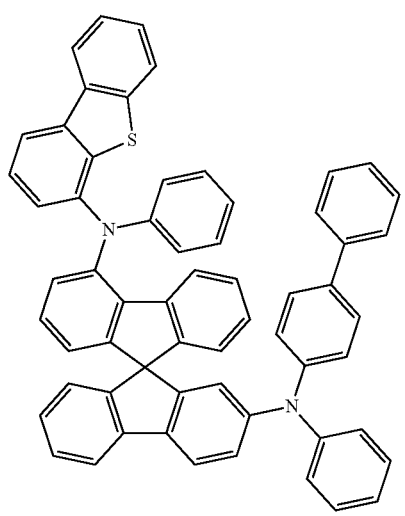
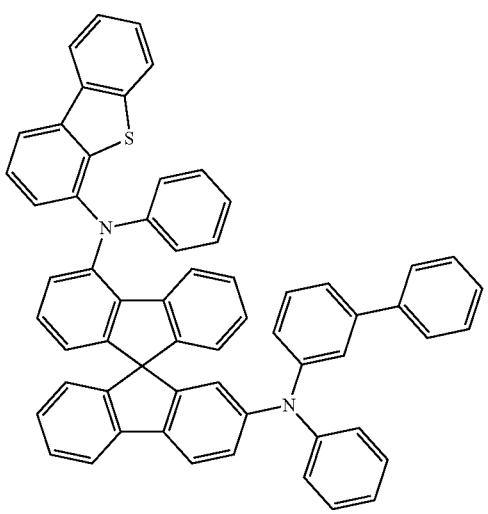
160
-continued
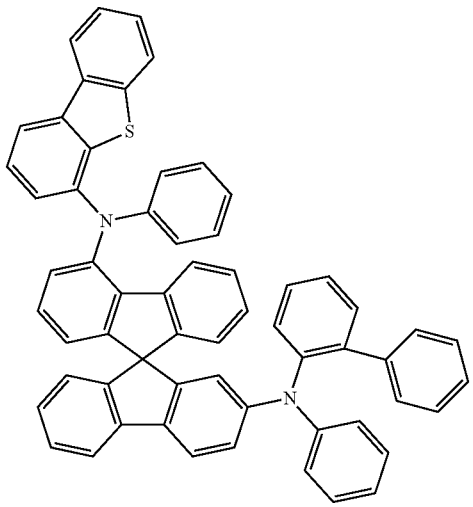
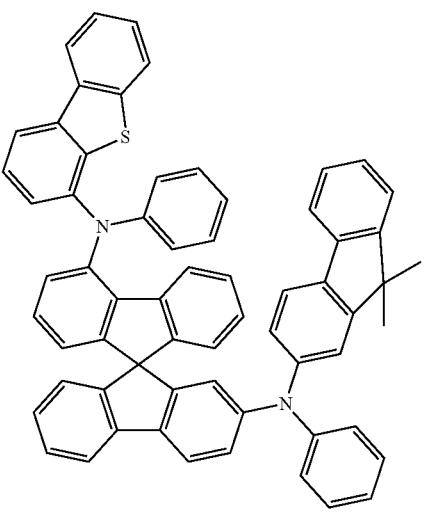
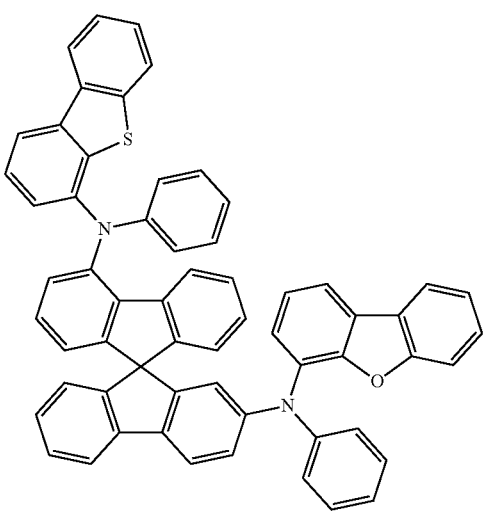

161
-continued
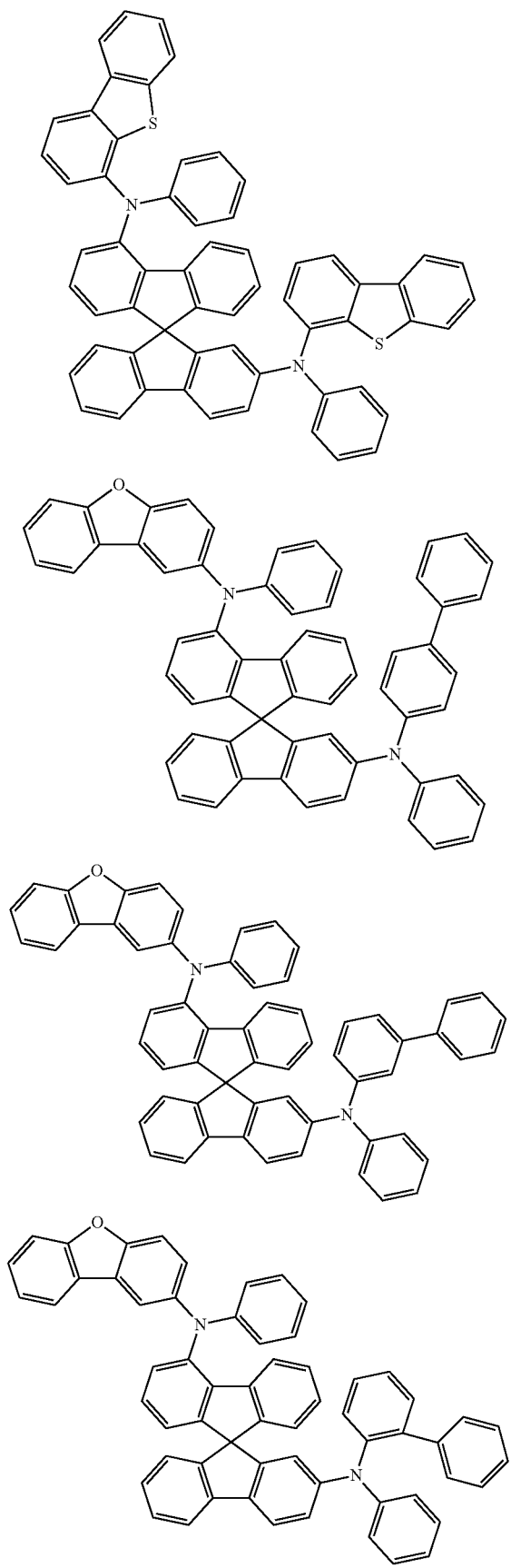
162
-continued
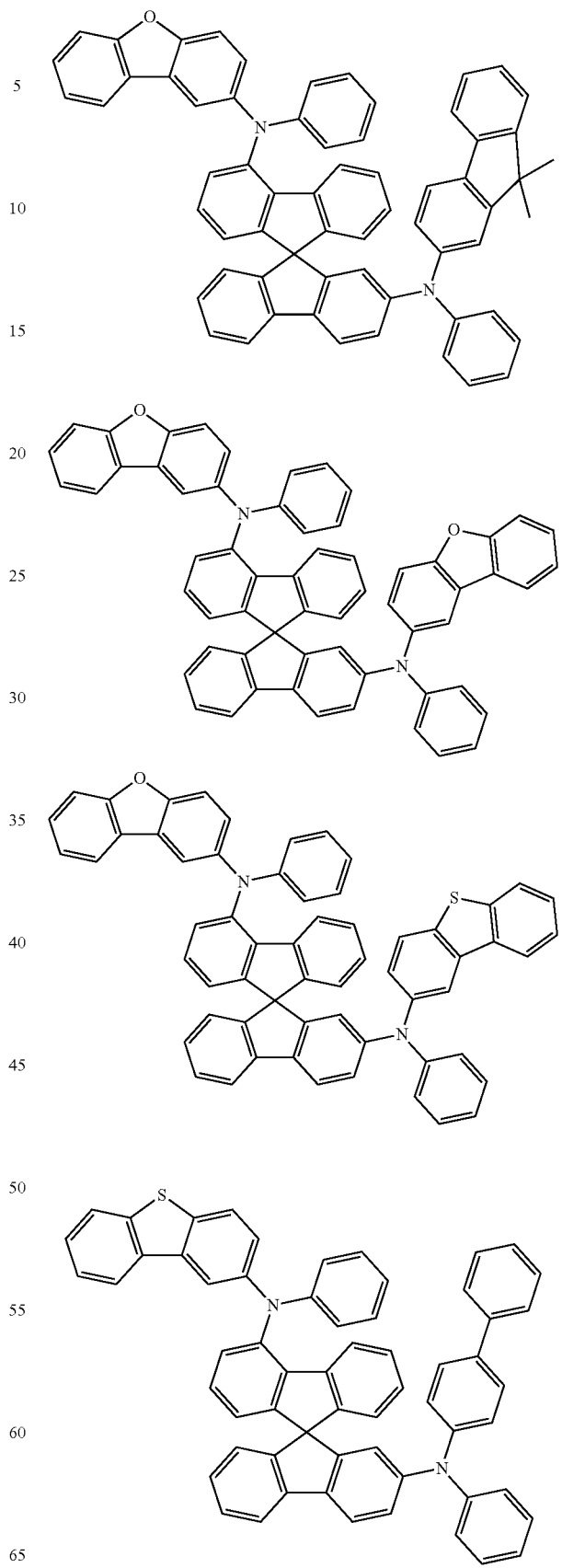

163
-continued
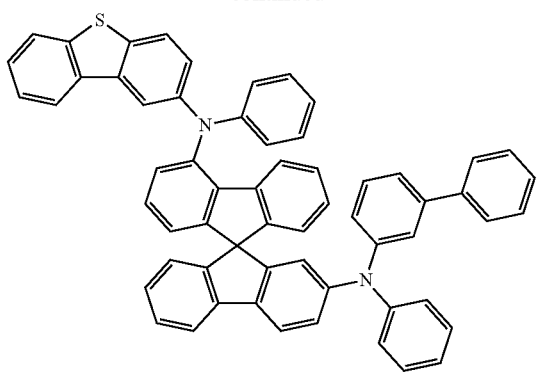
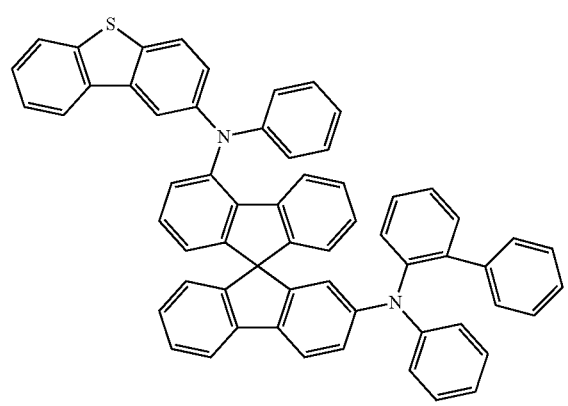
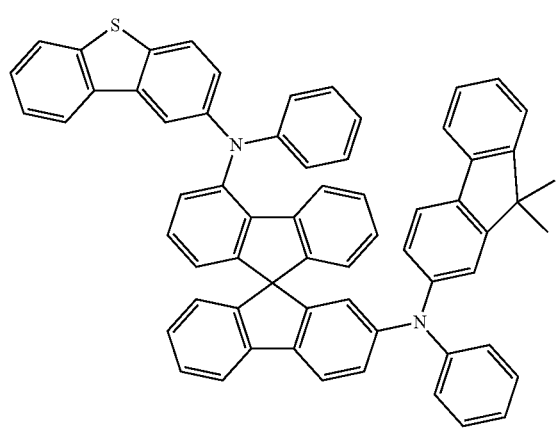
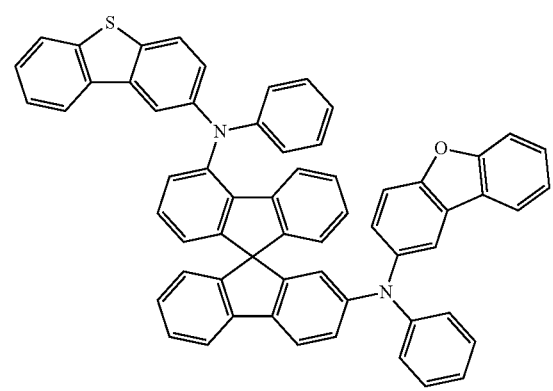
164
-continued
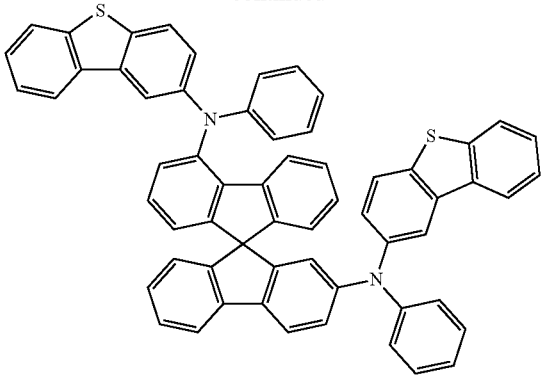
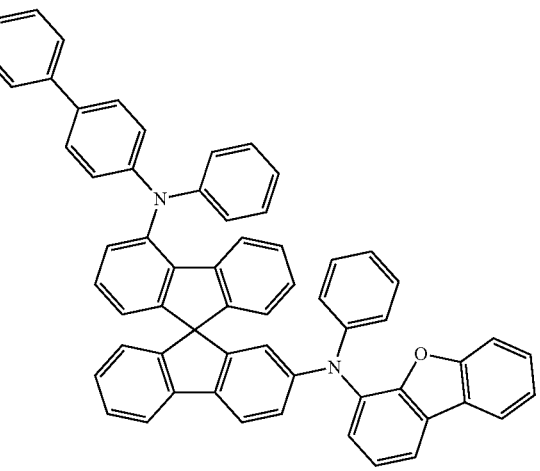
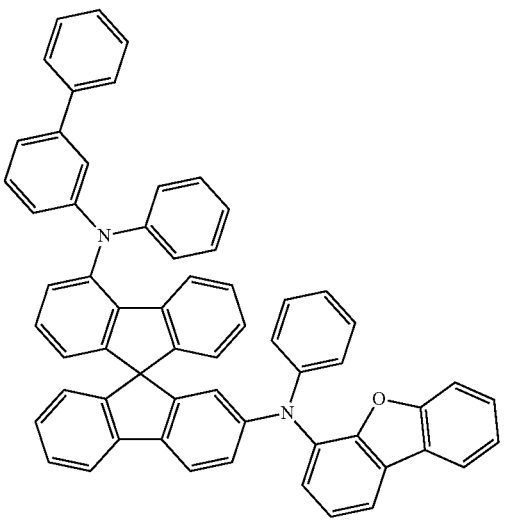

165
-continued
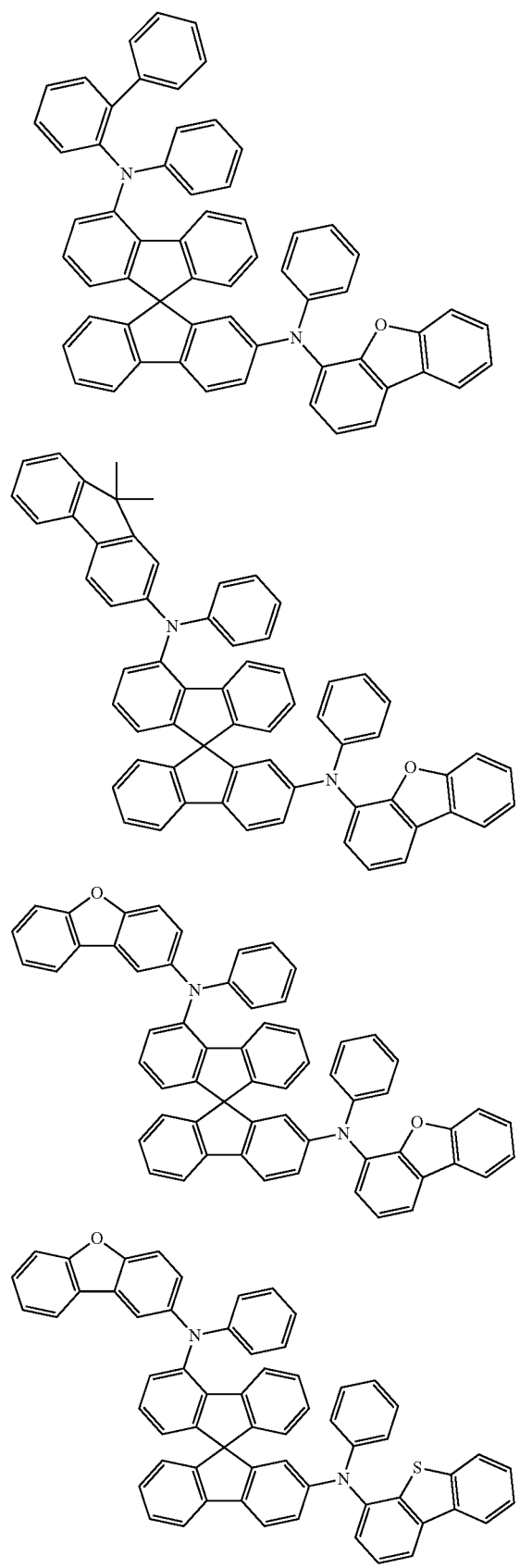
166
-continued
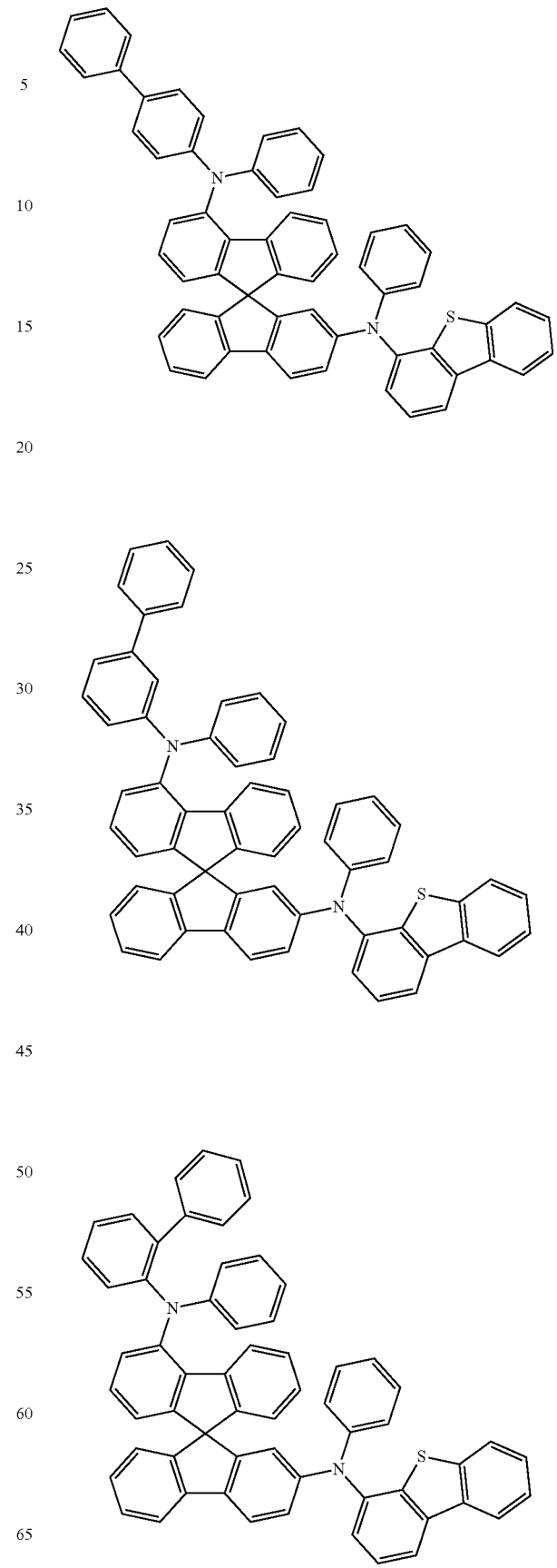

167
-continued
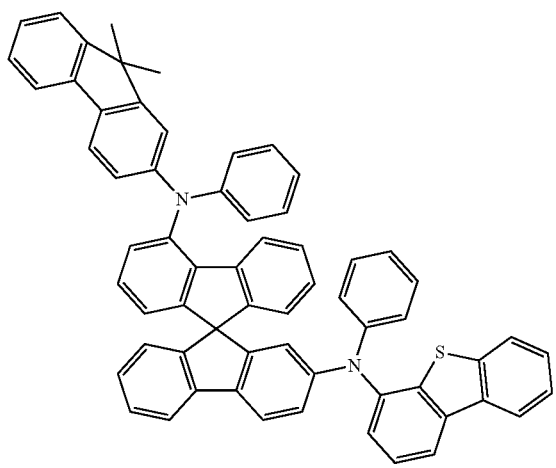
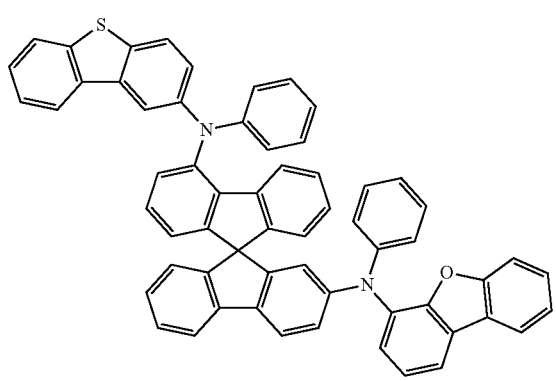
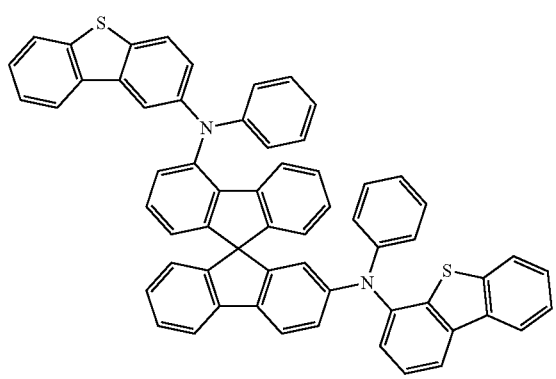
168
-continued
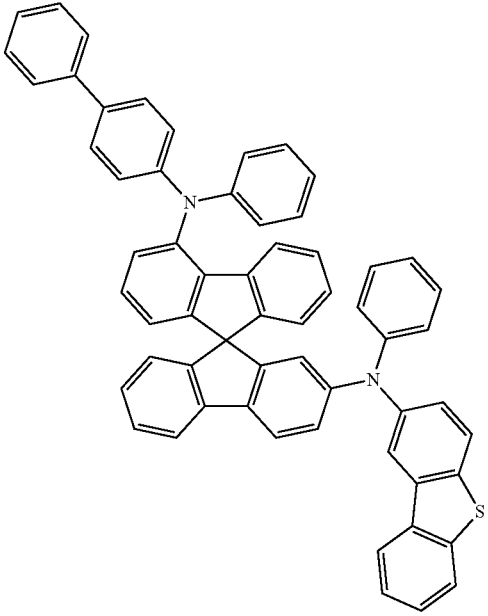
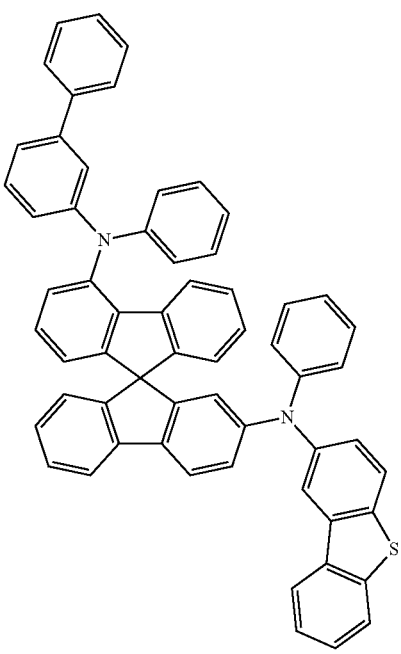

169
-continued
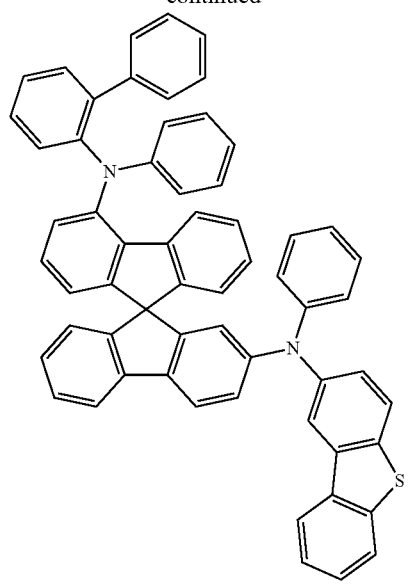
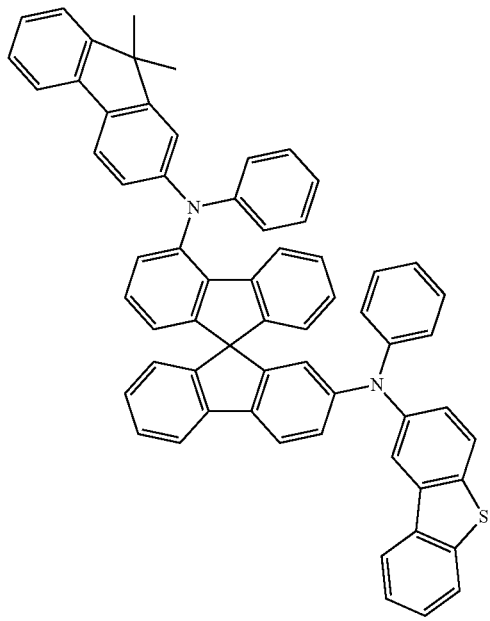
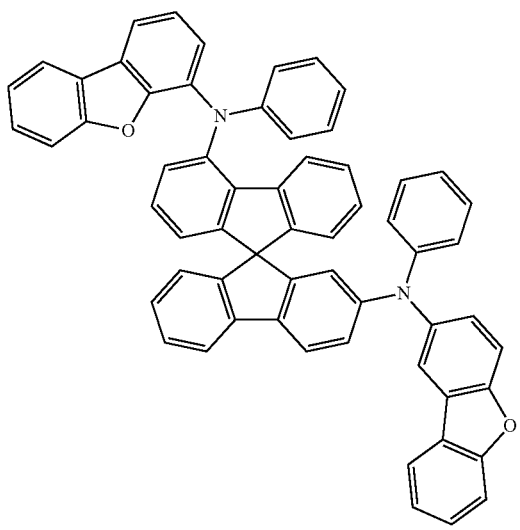
170
-continued
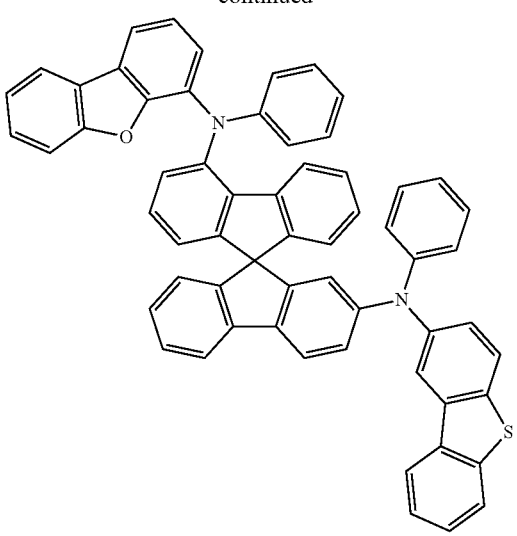
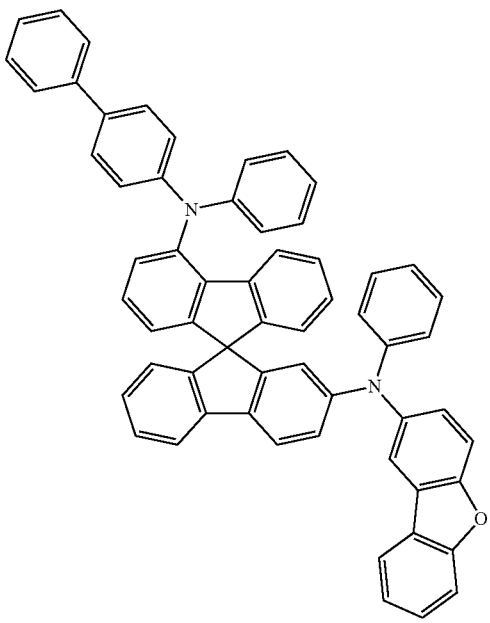

171
172
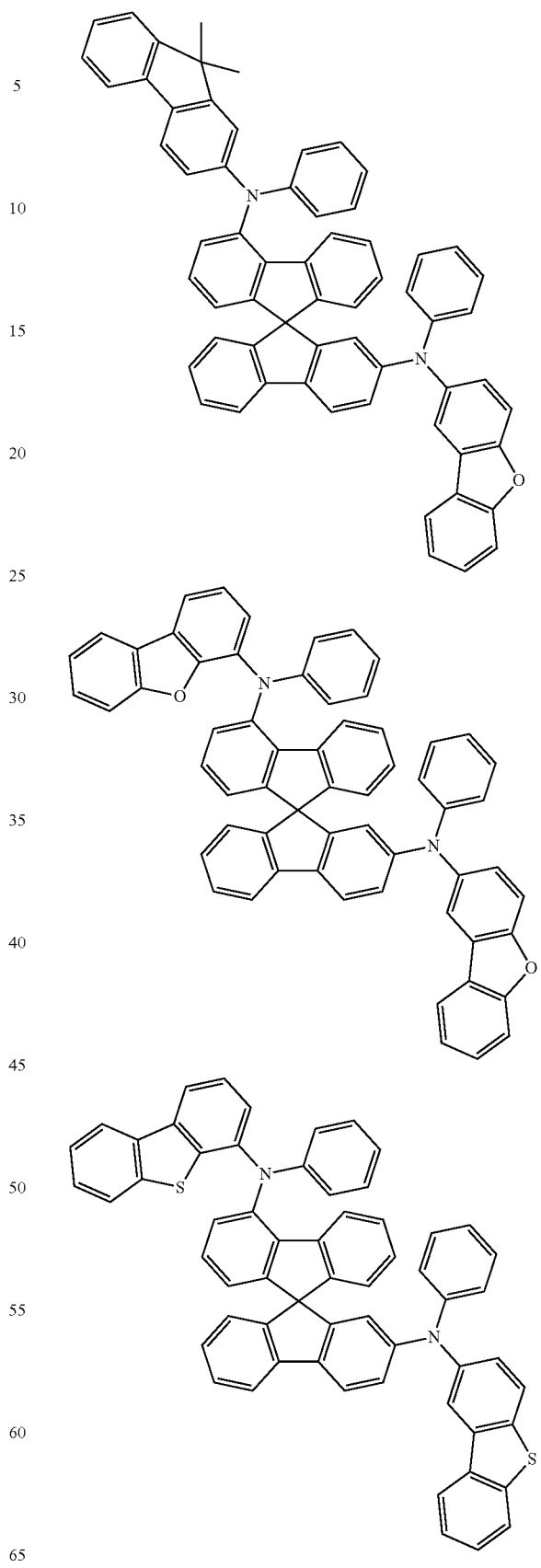

173
-continued
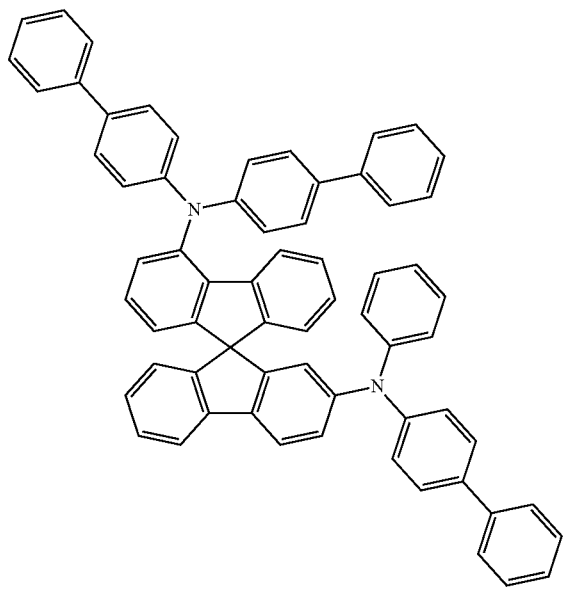
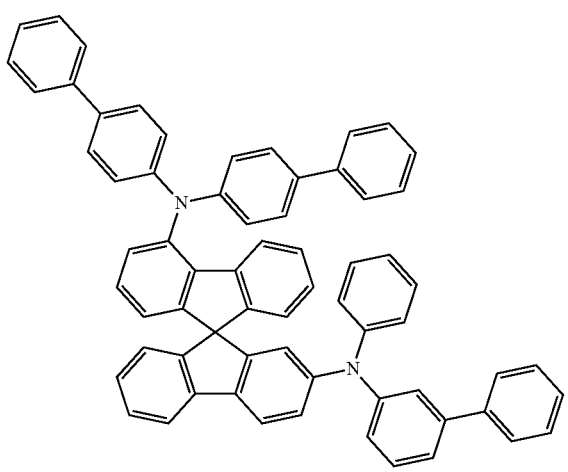
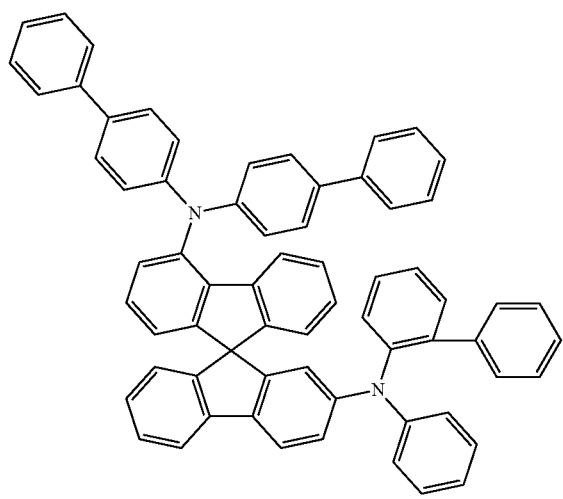
174
-continued
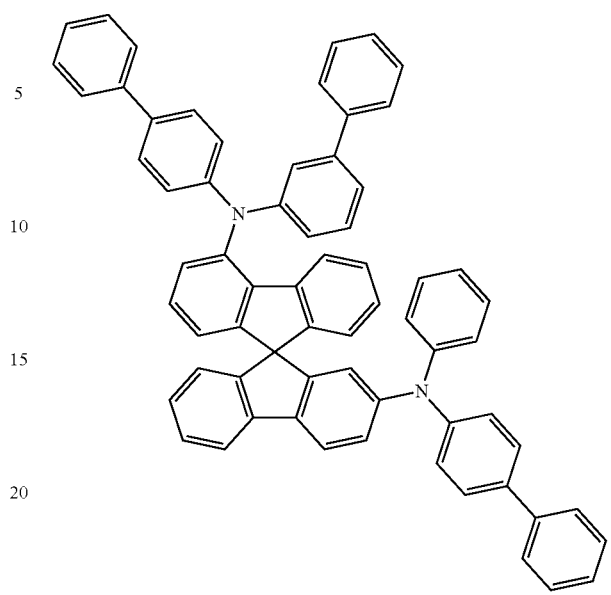
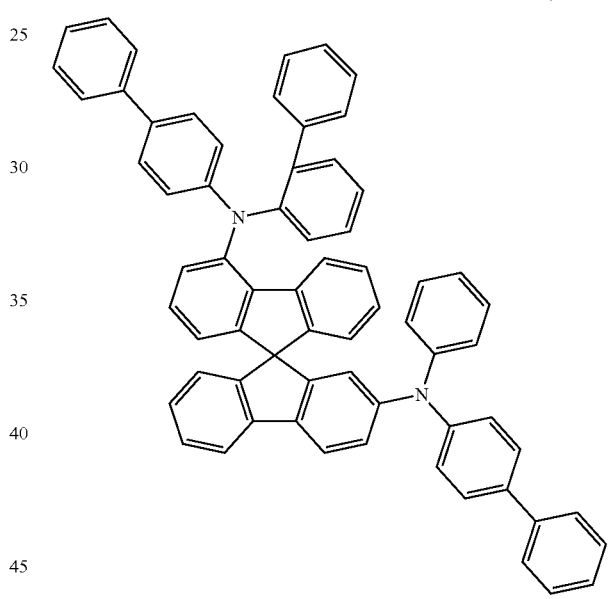
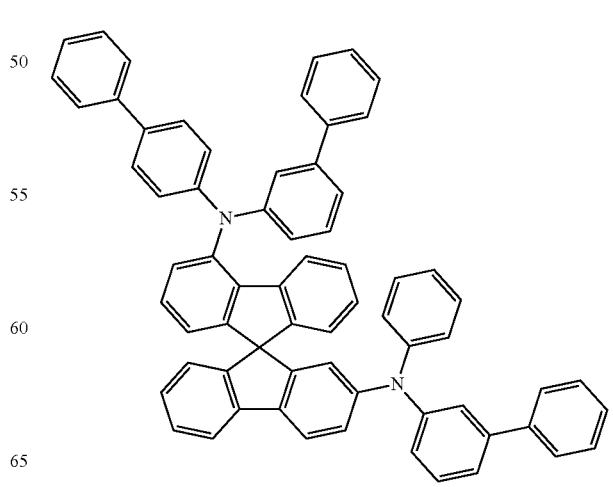

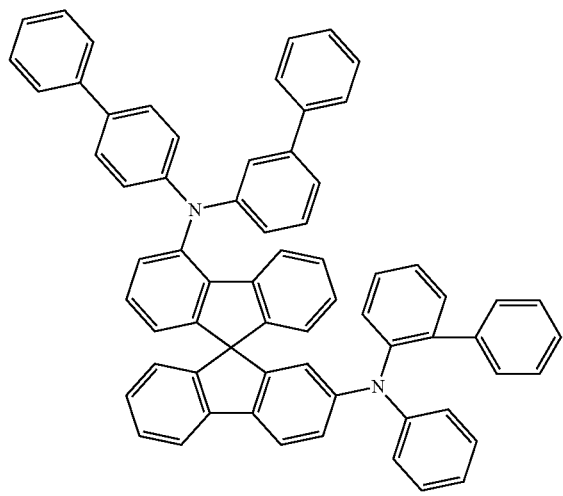
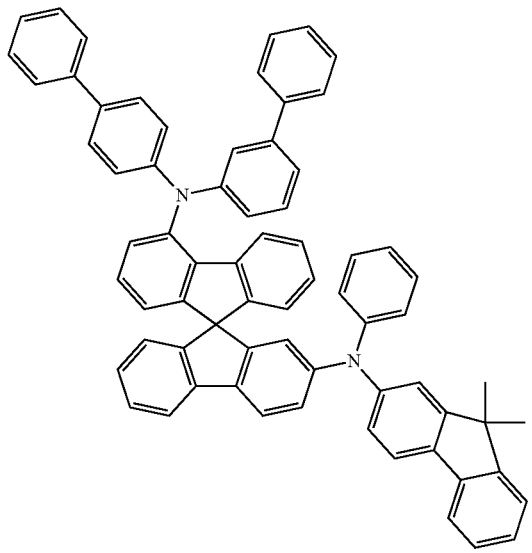
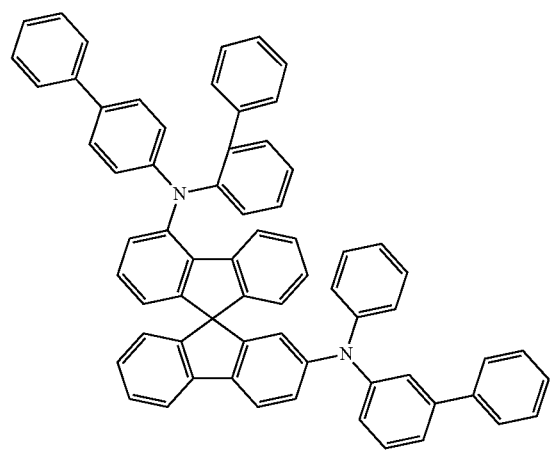
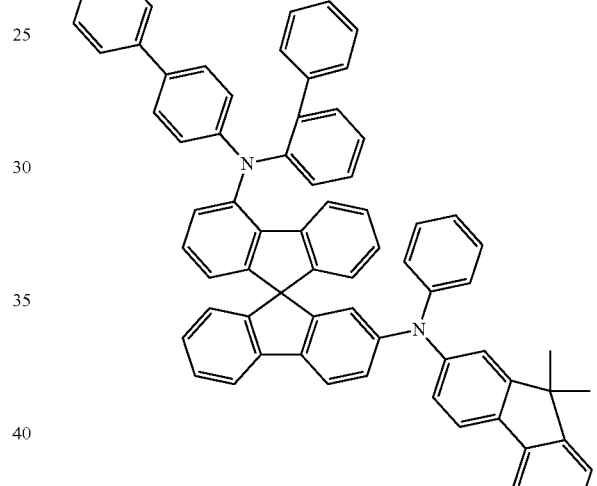
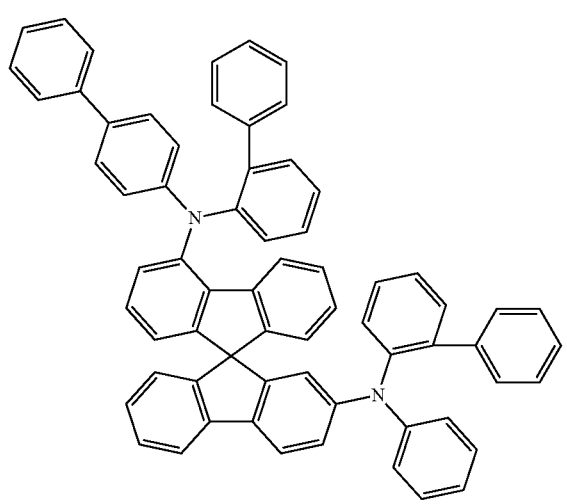
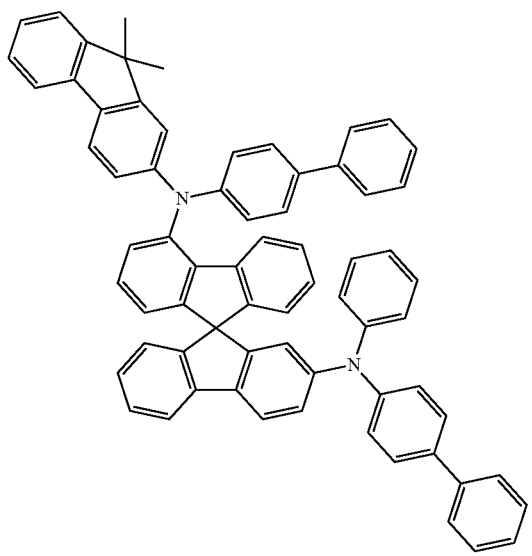

177
-continued
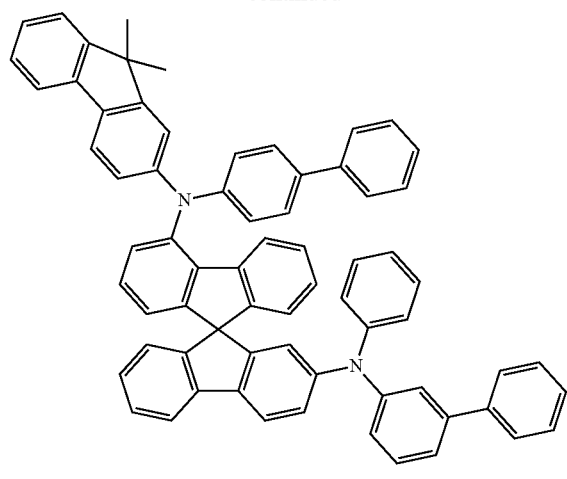
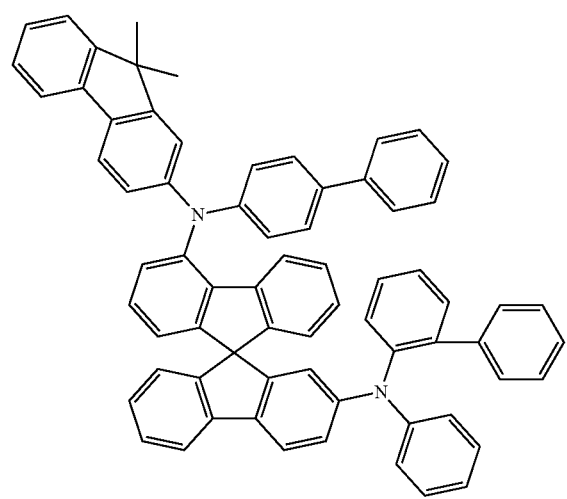
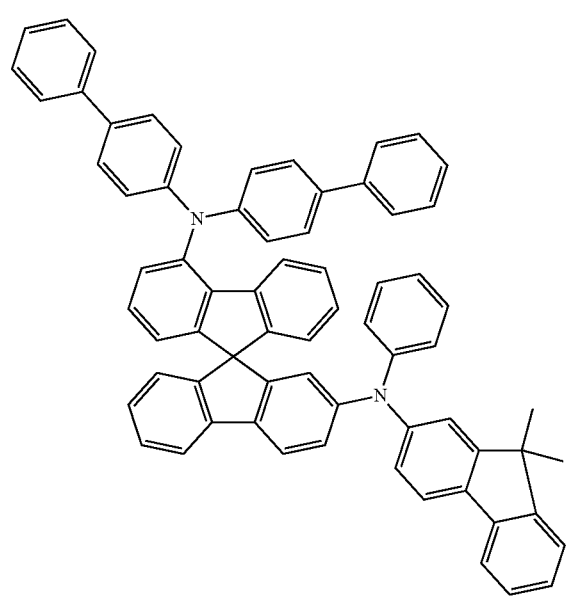
178
-continued
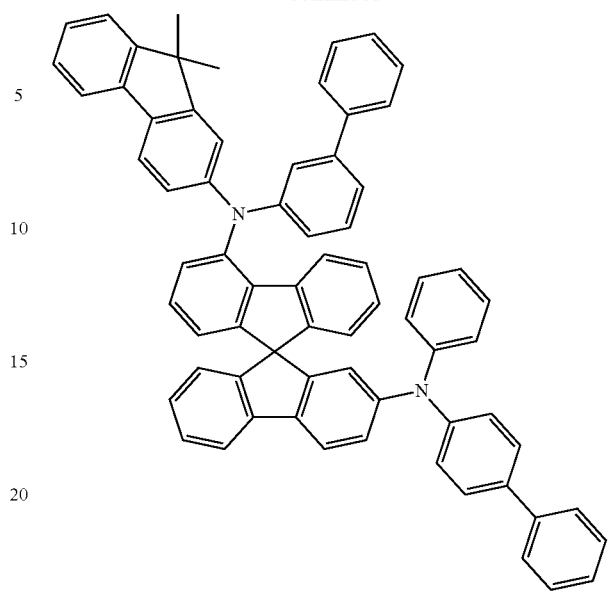
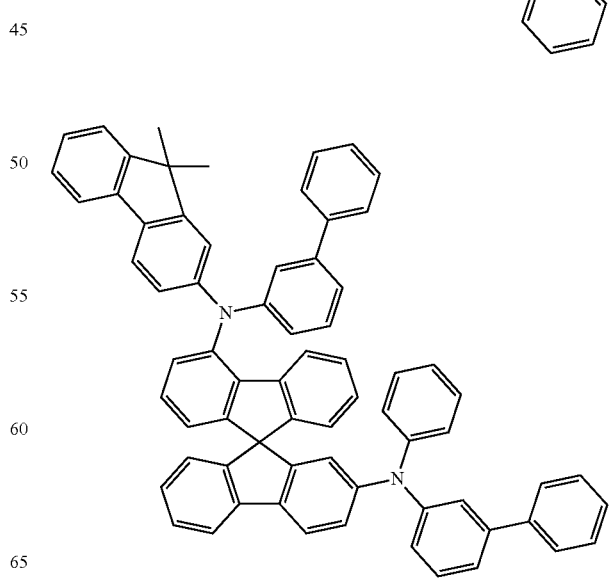

179
-continued
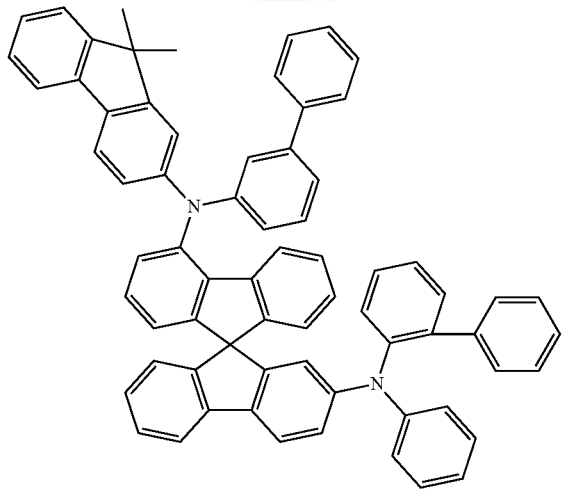
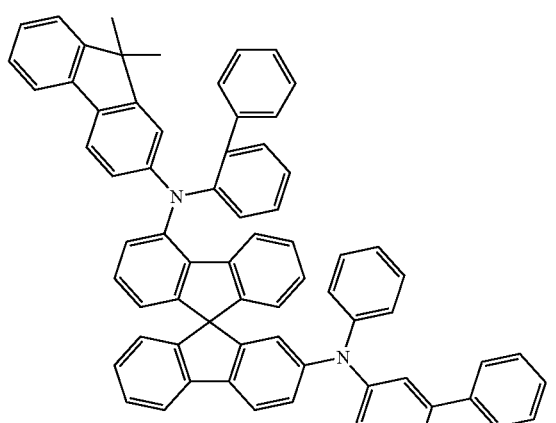
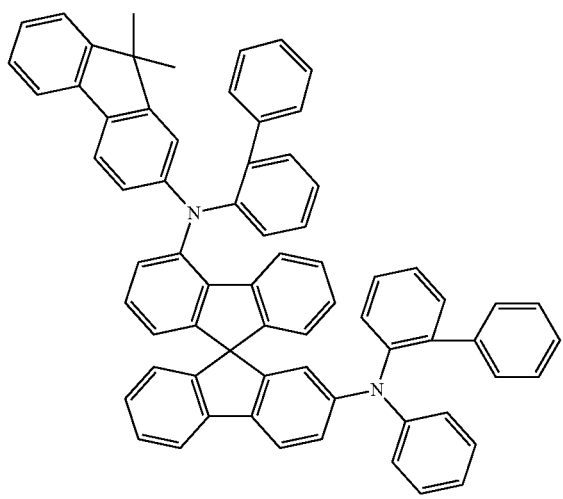
180
-continued
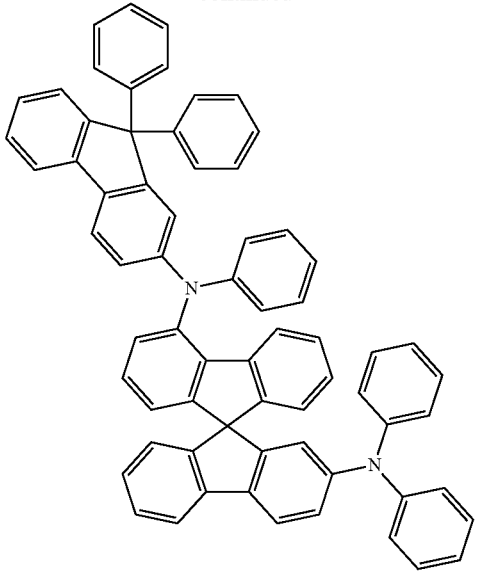
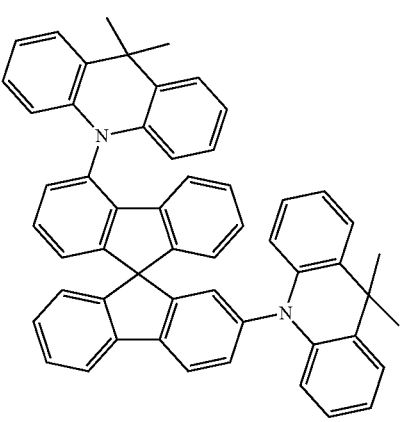
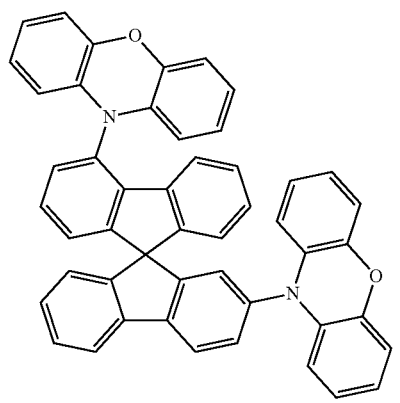

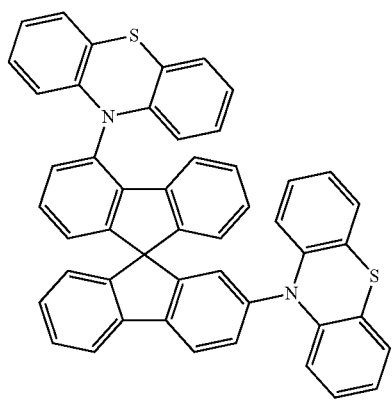
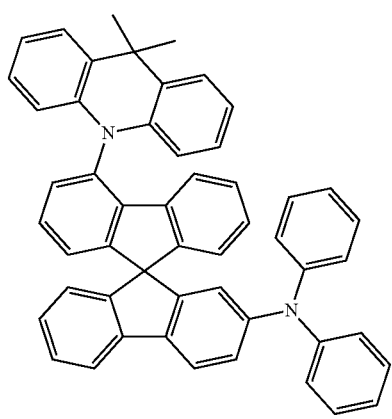
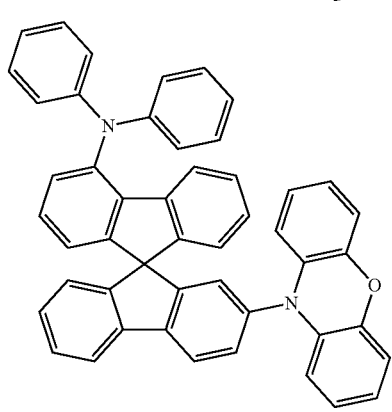
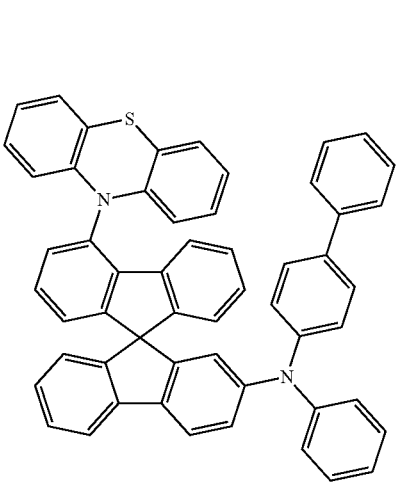
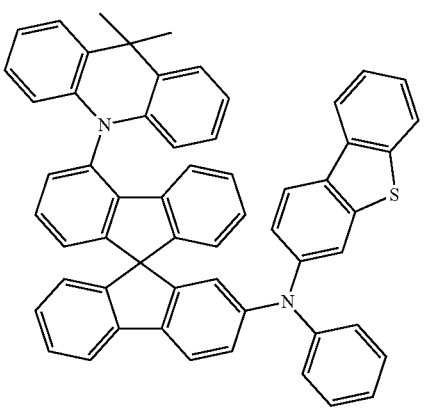

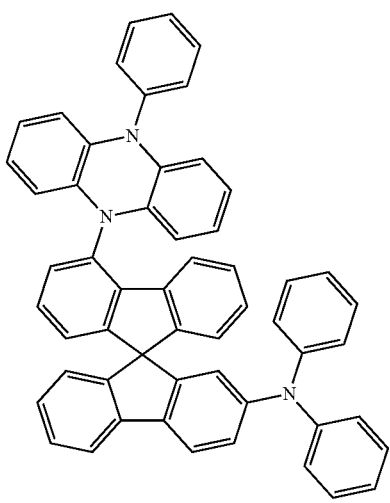
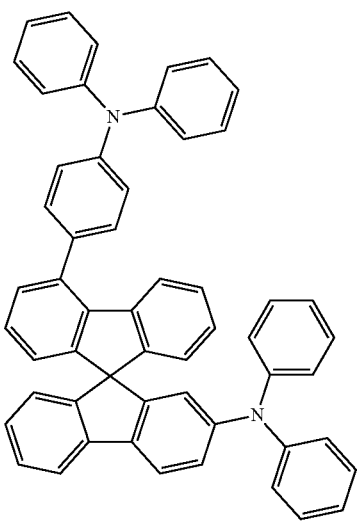
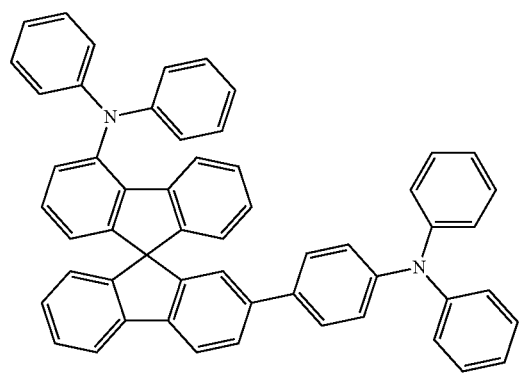
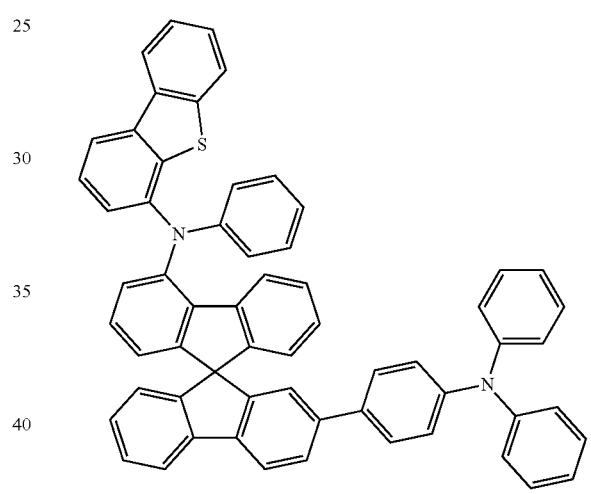
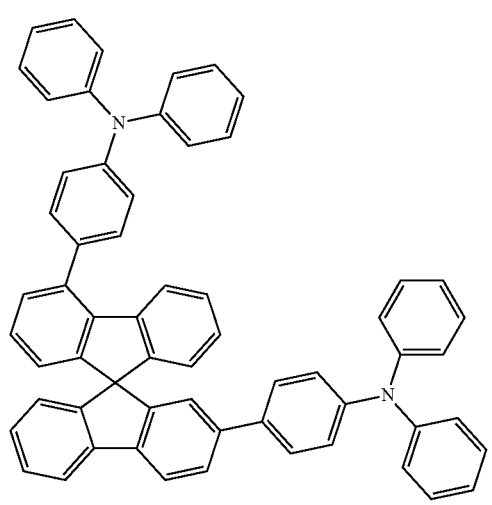
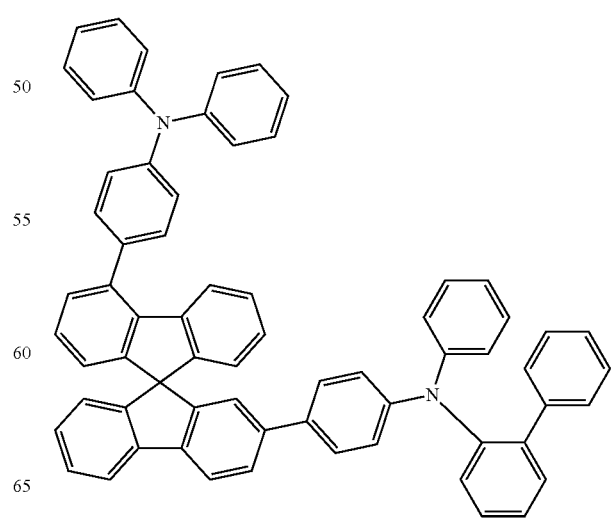

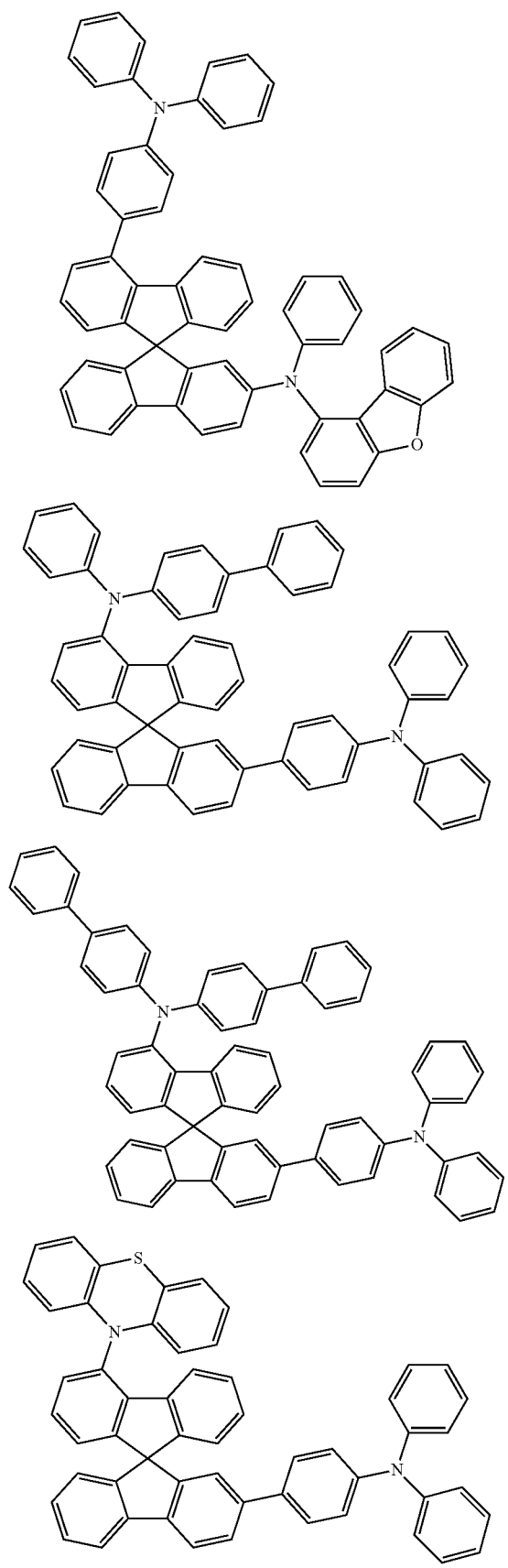
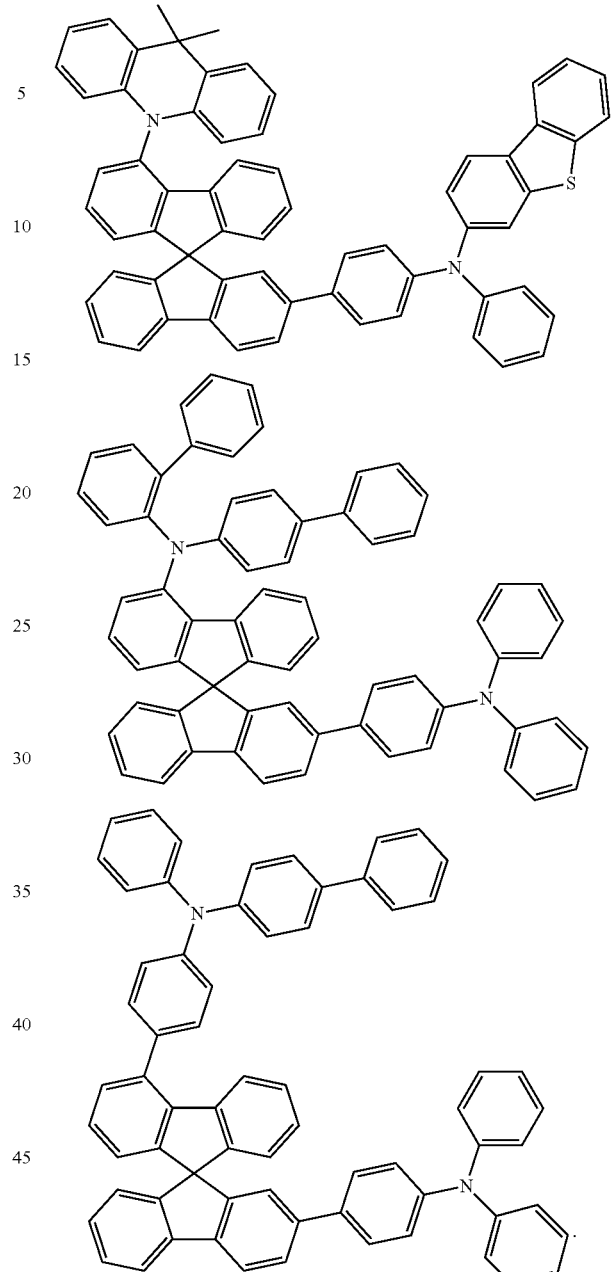

5. An organic light emitting device comprising:
a first electrode;
a second electrode provided to face the first electrode; and
one or more organic material layers provided between the first electrode and the second electrode,
wherein the one or more organic material layers comprise the compound of claim 1.

6. The organic light emitting device of claim 5, wherein the one or more organic material layers comprise a hole transport layer, and the hole transport layer comprises the compound.

7. The organic light emitting device of claim 5, wherein the one or more organic material layers comprise a hole injection layer, and the hole injection layer comprises the compound.

8. The organic light emitting device of claim 5, wherein the one or more organic material layers comprise a hole adjusting layer, and the hole adjusting layer comprises the compound.

9. The organic light emitting device of claim 5, wherein the one or more organic material layers comprise a layer which injects and transports holes simultaneously, and the layer which injects and transports holes simultaneously comprises the compound.

10. The organic light emitting device of claim 5, wherein the one or more organic material layers comprise a light emitting layer, and the light emitting layer comprises a compound represented by the following Chemical Formula A-1:

[Chemical Formula A-1]

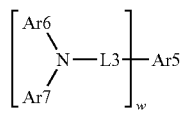

in Chemical Formula A-1,
w is an integer of 1 or more,
Ar5 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L3 is a direct bond; a substituted or unsubstituted arylene group; or a substituted or unsubstituted heteroarylene group,
Ar6 and Ar7 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and
when w is 2 or more, two or more structures in the parenthesis are the same as or different from each other.

11. The organic light emitting device of claim 10, wherein L3 is a direct bond, Ar5 is a divalent pyrene group, Ar6 and Ar7 are the same as or different from each other, and are each independently a phenyl group which is unsubstituted or substituted with a methyl group; a dibenzofuran group which is unsubstituted or substituted with a tert-butyl group, and w is 2.

12. The organic light emitting device of claim 5, wherein the one or more organic material layers comprise a light emitting layer, and the light emitting layer comprises a compound represented by the following Chemical Formula A-2:

[Chemical Formula A-2]

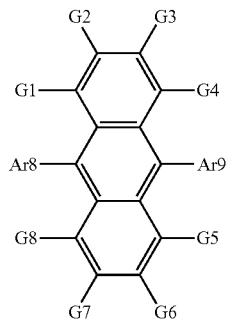

in Chemical Formula A-2,
Ar8 and Ar9 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

13. The organic light emitting device of claim 12, wherein Ar8 is a 1-naphthyl group, and Ar9 is a 2-naphthyl group.

14. The organic light emitting device of claim 10, wherein the one or more light emitting layers comprise a compound represented by the following Chemical Formula A-2:

[Chemical Formula A-2]

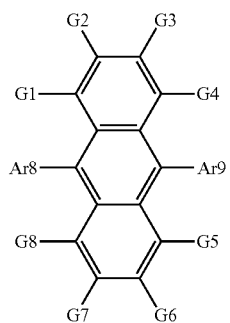

in Chemical Formula A-2,
Ar8 and Ar9 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

* * * * *